US012797463B2

(12) United States Patent
Zhuang et al.

(10) Patent No.: US 12,797,463 B2
(45) Date of Patent: Nov. 17, 2026

(54) PERSONALIZED TUMOR VACCINE

(71) Applicants: NE1 INC., New York, NY (US); NATIONAL INSTITUTE OF HEALTH, Bethesda, MD (US); UNIVERSITY OF SOUTH BOHEMIA IN CESKE BUDEJOVICE, Ceske Budejovice (CZ)

(72) Inventors: Zhengping Zhuang, Bethesda, MD (US); Rogelio Medina, Downey, CA (US); Herui Wang, Mclean, VA (US); Jan Ženka, Ceské Budejovice (CZ); Karel Pacak, Bethesda, MD (US); Winson Ho, Austin, TX (US)

(73) Assignees: NE1 Inc., New York, NY (US); The United States of America, as represented by The Secretary, Department of Health and Human Services, Bethesda, MD (US); University of South Bohemia, Geske Budejovice (CZ)

(*) Notice: Subject to any disclaimer, the term of this patent is extended or adjusted under 35 U.S.C. 154(b) by 1062 days.

(21) Appl. No.: 17/783,866

(22) PCT Filed: Dec. 11, 2020

(86) PCT No.: PCT/US2020/064412

§ 371 (c)(1),
(2) Date: Jun. 9, 2022

(87) PCT Pub. No.: WO2021/119376

PCT Pub. Date: Jun. 17, 2021

(65) Prior Publication Data

US 2023/0054318 A1 Feb. 23, 2023

Related U.S. Application Data

(60) Provisional application No. 62/946,934, filed on Dec. 11, 2019.

(51) Int. Cl.

| | |
|---|---|
| ***A61K 39/39*** | (2006.01) |
| ***A61K 39/00*** | (2006.01) |
| ***A61K 39/395*** | (2006.01) |
| ***A61P 35/00*** | (2006.01) |
| ***C07K 16/28*** | (2006.01) |

(52) U.S. Cl.

CPC .............. *A61K 39/39* (2013.01); *A61K 39/00* (2013.01); *A61K 39/0011* (2013.01); *A61K 39/3955* (2013.01); *A61P 35/00* (2018.01); *C07K 16/2878* (2013.01); *A61K 2039/5152* (2013.01); *A61K 2039/5154* (2013.01); *A61K 2039/55561* (2013.01); *A61K 2039/55572* (2013.01); *A61K 2039/55583* (2013.01)

(58) Field of Classification Search

CPC .... A61K 39/39; A61K 39/00; A61K 39/0011; A61K 2039/5152; A61P 35/00; C07K 16/2878

See application file for complete search history.

(56) References Cited

U.S. PATENT DOCUMENTS

2013/0202707 A1 8/2013 Ali et al.

OTHER PUBLICATIONS

Zhang, R., et al. Biomaterials for vaccine-based cancer immunotherapy, Journal of Controlled Release, Dec. 28, 2018, vol. 292; pp. 256-276; p. 260, 1st column, 2nd paragraph; p. 261, 1st column, 1st paragraph; p. 264, 1st column, 1st paragraph; p. 266, 1st column, 2nd paragraph to 2nd column, 1st paragraph; DOI: 10.1016/j.conrel.2018.10.008.

Hege, KM, et al., GM-CSF Gene-Modified Cancer Cell Immunotherapies: Of Mice and Men, International Reviews of Immunology, Sep.-Dec. 2006, vol. 25, Nos. 5-6; pp. 321-352; p. 329, 2nd-3rd paragraphs; Table 1; p. 336, 3rd paragraph; DOI: 10.1080/08830180600992498.

Wu, G., et al., Novel Mannan-PEG-PE Modified Bioadhesive PLGA Nanoparticles for Targeted Gene Delivery, Journal of Nanomaterials, 2012, vol. 2012, No. 981670; pp. 1-9; abstract; p. 1, 2nd column, 2nd paragraph to p. 2, 1st column, 1st paragraph; DOI: 10.1155/2012/981670.

Clappaert, EJ et al., Diamonds in the Rough: Harnessing Tumor-Associated Myeloid Cells for Cancer Therapy, Frontiers in Immunology, Oct. 8, 2018, vol. 9, No. 2250; pp. 1-20; p. 4, 2nd column, 1st-2nd paragraphs; p. 5, 1st column, 3rd paragraph; p. 6, 1st column, 2nd paragraph; DOI: 10.33879/fimmu.2018.02250.

Yang, R., et al., Cancer Cell Membrane-Coated Adjuvant Nanoparticles with Mannose Modification for Effective Anticancer Vaccination. ACS Nano, May 17, 2018, vol. 12, No. 6; pp. 5121-5129; DOI: 10.1021/acsnano.7b09041.

United States Patent & Trademark Office, The International Search Report and the Written Opinion issued in corresponding International application No. PCT/US2020/064412, dated Apr. 2, 2021, 10 pp.

Wang, H. et al., "IMMU-23. Targeting Metastatic and CNS Tumors via Mannan-BAM, TLR Ligands, and Anti-CD40 Antibody", Neuro-Oncology, Abstracts, Nov. 11, 2019, 2 pages.

Medina, R. et al., "Induction of Immune Response against Metastatic Tumors via Vaccination of Mannan-BAM, TLR Ligands, and Anti-CD40 Antibody (MBTA)", Advanced Therapeutics, vol. 3, No. 9, Jun. 9, 2020.

Extended European Search Report, European Patent Office, European Patent No. 20899103.4, Nov. 22, 2023, 7 pages.

Uher et al., "Coley's Immunotherapy revived: Innate immunity as a link in priming cancer cells for an attack by adaptive immunity", Sem Oncol, Oct. 2019, vol. 46, No. 4-5, pp. 385-392.

Wang et al., "rWTC-MBTA Vaccine Induces Potent Adaptive Immune Responses Against Glioblastomas via Dynamic Activation of Dendritic Cells", Adv Sci, Apr. 2024, vol. 11, No. 14, e2308280, 15 pages.

(Continued)

*Primary Examiner* — Elly-Gerald Stoica

(74) *Attorney, Agent, or Firm* — Taft Stettinius & Hollister LLP

(57) ABSTRACT

Disclosed herein is a personalized tumor vaccine comprising attenuated cancer cells and a method of using said personalized tumor vaccine to treat cancer.

10 Claims, 38 Drawing Sheets

(56) References Cited

OTHER PUBLICATIONS

Ye et al., "rWTC-MBTA: autologous vaccine prevents metastases via antitumor immune responses", J Exp Clin Cancer Res, Jul. 12, 2023, vol. 42, No. 163, 17 pages.

PERSONALIZED TUMOR VACCINE

CROSS REFERENCE

This application is a 371 National Phase Entry of International Application No. PCT/US2020/064412, filed Dec. 11, 2020, and claims the benefit of U.S. Provisional Application No. 62/946,934, filed on Dec. 11, 2019, the contents of each of which are hereby incorporated by reference in their entirety.

FEDERALLY SPONSORED RESEARCH AND DEVELOPMENT

This invention was made with Government support under project number ZIA BC 011773 by the National Institutes of Health, National Cancer Institute and the Eunice Kennedy Shriver National Institute of Child Health and Human Development. The Government has certain rights in the invention.

FIELD OF THE INVENTION

The present invention relates generally to the preparation and use of a personalized tumor vaccine for cancer immunotherapy.

BACKGROUND OF THE INVENTION

Immune checkpoint inhibitors (ICIs), such as anti-PD1/PD-L1 and anti-CTLA-4, have vastly improved outcome of various types of advanced cancers, including melanoma and non-small cell lung cancer (see Nat Rev Cancer. 2018; 18 (3): 139-147. doi:10.1038/nrc.2017.117). However, it has become clear that only a subset of patients achieves a durable response to ICIs. One of the strongest predictors of objective response to ICIs is the tumor mutation burden (see N Engl J Med. 2017; 377 (25): 2500-2501. doi:10.1056/NEJMc1713444). However, many tumors including glioblastoma are less likely to respond to single agent ICI therapy presumably due to the lack of neoantigens necessary to activate an adaptive immune response. These tumors are often found to be "immunologically cold" with low T-cell infiltration. An "immunologically hot" tumor with high T-cell infiltration suggests the presence of an active antitumor immune response and predicts a favorable response to ICIs. Hence, conversion of a "cold" to "hot" immunogenic phenotype is an important step to make a successful immunotherapy. Thus, there is an urgent need to identify novel treatments or immunotherapeutic agents capable of converting an "immunologically cold" tumor to an "immunologically hot" tumor.

On the other hand, often a promising immunotherapeutic agent shows potent antitumor responses only when applied or injected intratumorally (in situ). Due to its reliance on an anatomically accessible tumor, the in situ injection strategy severely limits potential applications for the immunotherapeutic agent, as primary tumors are commonly surgically debulked in clinical settings or may be located in poorly accessible anatomical locations.

The cancer immunotherapy field is still in its infancy and more immunotherapeutic drugs and their clinic outcomes are being explored. On the other hand, various forms of solid tumors, especially those from the nervous system, call for a delivery strategy unbound by the in situ requirement.

SUMMARY OF THE INVENTION

Disclosed herein, in some embodiments, are personalized tumor vaccines. In an aspect, a personalized tumor vaccine comprises: (a) a phagocytosis stimulating agent, (b) an immunostimulatory adjuvant, and (c) attenuated cancer cells, wherein the personalized tumor vaccine, when administered to an individual in need thereof, is effective to activate an immune response.

In some embodiments, the attenuated cancer cells are obtained from a tumor of the individual. In some embodiments, the tumor is a solid tumor. In some embodiments, the tumor is a liquid tumor.

In some embodiments, the attenuated cancer cells are prepared by (a) harvesting cancer cells from a biopsy of a site of tumor from the individual, (b) culturing the harvested cancer cells to a therapeutically relevant amount, and (c) irradiating the cultured cancer cells.

In some embodiments, the attenuated cancer cells are present in an amount from about 1.0×10ˆ3 to about 1.0×10ˆ7. In some embodiments, the phagocytosis stimulating agent comprises a mannan. In some embodiments, the mannan is present in an amount from about 2 mg/dose to about 200 mg/dose. In some embodiments, the phagocytosis stimulating agent is conjugated to a biocompatible anchor for cell membrane (BAM). In some embodiments, the BAM is present in an amount from about 0.2 mg/dose to about 20 mg/dose. In some embodiments, the BAM comprises Formula I

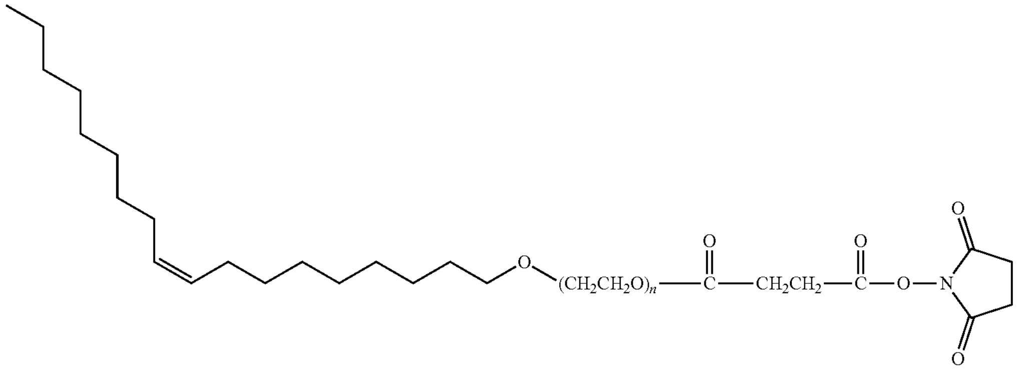

wherein n is the number of ethylene oxide (EO) unit repeats in the PEG chain.

In some embodiments, the immunostimulatory adjuvant comprises a Toll like receptor (TLR) agonist. In some embodiments, the TLR agonist comprises R-848, poly(I:C), lipoteichoic acid (LTA), or combinations thereof. In some embodiments, the TLR agonist comprises R-848. In some embodiments, the R-848 is present in an amount from about 0.05 mg/dose to about 5 mg/dose. In some embodiments, the TLR agonist comprises poly(I:C). In some embodiments, the poly(I:C) is present in an amount from about 0.05 mg/dose to about 5 mg/dose. In some embodiments, the TLR agonist comprises lipoteichoic acid (LTA). In some embodiments, the LTA is present in an amount from about 0.05 mg/dose to about 5 mg/dose. In some embodiments, the immunostimulatory adjuvant comprises an anti-CD40 antibody. In some embodiments, the anti-CD40 antibody is present in an amount from about 0.04 mg/dose to about 4 mg/dose. In some embodiments, the immune response comprises an adaptive immune response specific to the attenuated cancer cells.

Disclosed herein, in some embodiments, are personalized tumor vaccines. In an aspect, a personalized tumor vaccine comprises: (a) a mannan, wherein the mannan is conjugated to a BAM, (b) a R-848, a poly(I:C), and an LTA, (c) an anti-CD40 antibody, and (d) irradiated cancer cells, wherein the personalized tumor vaccine, when administered to an individual in need thereof, is effective to activate an immune response.

Disclosed herein, in some embodiments, are methods for treating cancer. In an aspect, a method for treating cancer comprises administering to an individual in need thereof an effective amount of pharmaceutical composition, wherein the pharmaceutical composition comprises: (a) a phagocytosis stimulating agent, (b) an immunostimulatory adjuvant, and (c) attenuated cancer cells.

In some embodiments, the attenuated cancer cells are obtained from a tumor of the individual. In some embodiments, the tumor is a solid tumor. In some embodiments, the tumor is a liquid tumor. In some embodiments, the attenuated cancer cells are prepared by (a) harvesting cancer cells from a biopsy of a site of tumor from the individual, (b) culturing the harvested cancer cells to a therapeutically relevant amount, and (c) irradiating the cultured cancer cells.

In some embodiments, the attenuated cancer cells are present in an amount from about 1.0×10ˆ3 to about 1.0×10ˆ7. In some embodiments, the phagocytosis stimulating agent comprises a mannan. In some embodiments, the mannan is present in an amount from about 2 mg/dose to about 200 mg/dose. In some embodiments, the phagocytosis stimulating agent is conjugated to a biocompatible anchor for cell membrane (BAM). In some embodiments, the BAM is present in an amount from about 0.2 mg/dose to about 20 mg/dose. In some embodiments, the BAM comprises Formula I

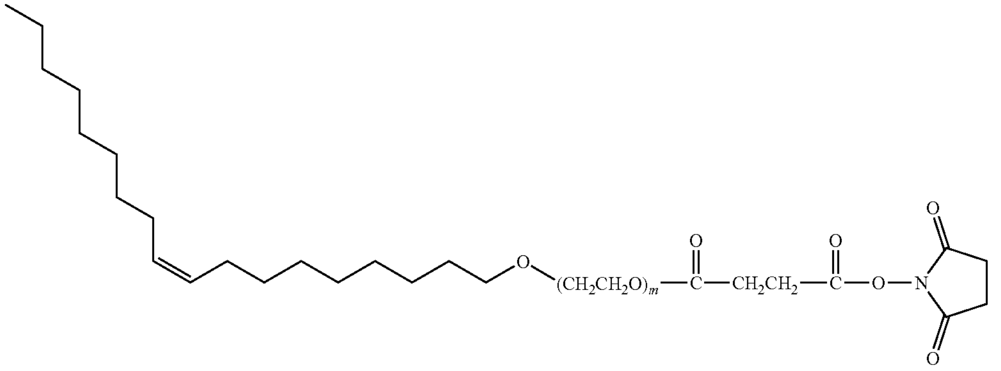

wherein n is the number of ethylene oxide (EO) unit repeats in the PEG chain.

In some embodiments, the immunostimulatory adjuvant comprises a Toll like receptor (TLR) agonist. In some embodiments, the TLR agonist comprises R-848, poly(I:C), lipoteichoic acid (LTA), or combinations thereof. In some embodiments, the TLR agonist comprises R-848. In some embodiments, the R-848 is present in an amount from about 0.05 mg/dose to about 5 mg/dose. In some embodiments, the TLR agonist comprises poly(I:C). In some embodiments, the poly(I:C) is present in an amount from about 0.05 mg/dose to about 5 mg/dose. In some embodiments, the TLR agonist comprises lipoteichoic acid (LTA). In some embodiments, the LTA is present in an amount from about 0.05 mg/dose to about 5 mg/dose. In some embodiments, the immunostimulatory adjuvant comprises an anti-CD40 antibody. In some embodiments, the anti-CD40 antibody is present in an amount from about 0.04 mg/dose to about 4 mg/dose. In some embodiments, the personalized tumor vaccine is administered subcutaneously. In some embodiments, the personalized tumor vaccine activates an immune response specific to the attenuated cancer cells. In some embodiments, the immune response comprises an adaptive immune response.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings ("FIGURE." or "FIGURES." herein), of which:

FIG. 1A depicts a cartoon schematic of a CT26 tumor-bearing mouse model of subcutaneous primary and metastatic distant tumors. The mouse is viewed from the dorsal side. A representative primary tumor and metastatic distant tumor is established at 101 on the right flank and 102 on the left flank, respectively.

FIG. 1B shows representative pictures of CT26 tumor-bearing mice 10 days after injection of saline.

FIG. 2A depicts a schematic timeline of the MBTA immunotherapy. FIG. 2B shows a schematic timeline of the MBTA immunotherapy. FIG. 2C shows representative pictures of CT26 tumor-bearing mice 10 days after the start of the MBTA immunotherapy. The locations of the representative primary and metastatic tumors are shown by arrows. The mouse is viewed from the dorsal side. FIG. 2D depicts line graphs showing the relationship of the primary tumor volume ($mm^3$) and time for the CT26 tumor-bearing mice with the primary tumor injected in situ with saline (n=7, left-panel) and MBTA (n=7, right panel). The primary tumors of most mice with the in situ MBTA injection did not grow, as compared to those of the control mice injected with saline. FIG. 2E depicts line graphs showing the relationship of the metastatic distant tumor volume ($mm^3$) and time for the mice with the primary tumor injected in situ with saline (n=7, left-panel) and MBTA (n=7, right panel). The metastatic distant tumors of most mice with the in situ MBTA injection did not grow, as compared to those of the control mice. FIG. 2F depicts the cumulative survival curves of the CT26 tumor-bearing mice with the in situ injection at the primary tumor. By 20 days, all mice received the saline control (n=7) died, while all mice received the MBTA treatment (n=7) survived. At least 25% of the MBTA treated mice survived 100 days after the treatment. * p=0.0002 by Log-rank (Mantel-Cox) test. FIG. 2G depicts 2-dimensional flow cytometry plots confirming $CD4^+$ (left panel) or $CD8^+$ T-cell depletion (middle panel) in the spleen of the CT26 tumor-bearing mice. A control plot without T-cell depletion is shown in the right panel. Target depletion depleted ~90% of the $CD4^+$ or $CD8^+$ cells. FIG. 2H depicts line graphs showing the relationship of the primary tumor volume ($mm^3$) and time for the CT26 tumor-bearing mice with the primary tumor injected in situ with saline (n=9, top left panel), MBTA without T-cell depletion (n=9, top right panel), MBTA plus $CD4^+$ cells depletion (n=5, bottom left panel), and MBTA plus $CD8^+$ cells depletion (n=5, bottom right panel). The primary tumors of most mice with the in situ MBTA injection did not grow, as compared to that of the control mice injected with saline. The primary tumors of most mice with in situ MBTA injection-whether non-T-cells, $CD4^+$ cells, or $CD8^+$ cells were depleted-did not grow, as compared to that of the control mice.

FIG. 3A depicts a schematic timeline of the MBTA immunotherapy and tumor immunophenotyping experiments (I.P.). FIG. 3B depicts a dot plot showing the percentage of $CD45^+$ cells in total live tumor dissociated cells. I.P. day 10 and I.P. day 16 analyses demonstrate that MBTA-treated mice had significantly higher immune cells within the primary tumor than saline-treated control mice did.  p<0.01 by Mann-Whitney U test. Data is shown as individual data points (dots) with median (line). FIG. 3C depicts a dot plot showing the percentage of $CD45^+$ cells in total live tumor dissociated cells from the primary tumors in the CT26 tumor-bearing mice. I.P. day 10 and I.P. day 16 analyses demonstrate that MBTA-treated mice had significantly higher immune cells within the metastatic distant tumor than saline-treated control mice did.  p<0.01 by Mann-Whitney U test. Data is shown as individual data points (dots) with median (line). FIG. 3D depicts a dot plot showing the percentage of innate immune cells in total live tumor dissociated cells from the primary tumors in the CT26 tumor-bearing mice. Innate immune cells found in the primary tumors corresponding to I.P. Day 10 and I.P. day 16 analyses are shown. * p<0.05,  p<0.01 by Mann-Whitney U test. Data is shown as individual data points (dots) with median (line). FIG. 3E depicts a dot plot showing the percentage of MHC II+ monocytes in total live tumor dissociated cells from the metastatic distant tumors in the CT26 tumor-bearing mice. I.P. day 10 and I.P. day 16 analyses demonstrate that MBTA-treated mice had more MHC II+ monocytes within the primary tumor than saline-treated control mice did.  p<0.01 by Mann-Whitney U test. Data is shown as individual data points (dots) with median (line). FIG. 3F depicts a dot plot showing the percentage of innate immune cells in total live tumor dissociated cells from the metastatic distant tumors in the CT26 tumor-bearing mice. I.P. day 16 analyses demonstrate that MBTA-treated mice had more dendritic cells, monocytes, and neutrophils within the metastatic distant tumor than saline-treated control did. * p<0.05,  p<0.01 by Mann-Whitney U test. Data is shown as individual data points (dots) with median (line). FIG. 3G depicts a dot plot showing the percentage of MHC II+ monocytes in total live tumor dissociated cells from the metastatic distant tumors in the CT26 tumor-bearing mice. I.P. day 10 and I.P. day 16 analyses demonstrate that MBTA-treated mice (pink) had more MHC II+ monocytes within the metastatic distant tumor than saline-treated control mice (black) did.  p<0.01 by Mann-Whitney U test. Data is shown as individual data points (dots) with median (line). FIG. 3H depicts a dot plot showing the percentage of alternatively activated macrophages in total live tumor dissociated cells from the primary tumors in the CT26 tumor-bearing mice. I.P. day 10 and I.P. day 16 analyses demonstrate that MBTA-treated mice (pink) had significantly fewer alternatively activated macrophages within the primary tumor than saline-treated control mice (black) did.  p<0.01 by Mann-Whitney U test. Data is shown as individual data points (dots) with median (line). FIG. 3I depicts a dot plot showing the percentage of alternatively activated macrophages in total live tumor dissociated cells from the metastatic distant tumors in the CT26 tumor-bearing mice. I.P. day 10 and I.P. day 16 analyses demonstrate that MBTA-treated mice had fewer alternatively activated macrophages within the distant tumor than saline-treated control mice did.  p<0.01 by Mann-Whitney U test. Data is shown as individual data points (dots) with median (line).

FIG. 4A depicts a dot plot showing the percentage of adaptive immune cells in total live tumor dissociated cells from the primary tumors in the CT26 tumor-bearing mice. I.P. day 10 and I.P. day 16 analyses demonstrate that the MBTA-treated mice had significantly more $CD8^+$ T-cells and B cells within the primary tumor in day 16 than the saline-treated control mice did. * $p<0.05$, ** $p<0.01$ by Mann-Whitney U test. Data is shown as individual data points (dots) with median (line). FIG. 4B depicts a dot plot showing the percentage of adaptive immune cells in total live tumor dissociated cells from the primary tumors in the CT26 tumor-bearing mice. I.P. day 10 and I.P. day 16 analyses demonstrate that the MBTA-treated mice had significantly more $CD8^+$ T-cells and B cells within the primary tumor in I.P. day 16 than the saline-treated control mice did. There were also more $CD8^+$ and fewer CD4+ T-cells in the distant tumor from the MBTA-treated mice than the control mice in I.P. day 10. * $p<0.05$, ** $p<0.01$ by Mann-Whitney U test. Data is shown as individual data points (dots) with median (line). FIG. 4C depicts a dot plot showing the percentage of IFN gamma or TNF alpha positive $CD4^+$ or $CD8^+$ T-cells per total $CD4^+$ or $CD8^+$ T-cells, respectively. Harvested left flank $CD4^+$ and $CD8^+$ T-cells corresponding to Day 10 and 16 analyses were stimulated for 5 h with PMA/Ionomycin ex-vivo and intracellular IFNγ and TNFα was determined by flow cytometry. The MBTA-treated mice had significantly more TNF alpha $CD8^+$ T-cells in I.P. day 16 and more IFN gamma $CD8^+$ T-cells in I.P. day 10 than saline-treated mice did. * $p<0.05$, ** $p<0.01$ by Mann-Whitney U test. Data is shown as individual data points (dots) with median (line). FIG. 4D depicts a dot plot showing the percentage of Granzyme B+ $CD8^+$ T-cells per total $CD8^+$ T-cells in the distant tumor from the CT26 tumor-bearing mice. The MBTA-treated mice had significantly more Granzyme B+$CD8^+$ T-cells in I.P. day 10 and 16 than the saline-treated mice did. FIG. 4E depicts a dot plot showing the percentage of AH-1-specific $CD8^+$ T-cells extracted from whole blood of the CT26 tumor-bearing mice. MBTA-treated mice had significantly more AH-1-specific (AH-1/H-2Ld-tetramer reactive) $CD8^+$ T-cells in the blood than the saline-treated mice did. Data is shown as individual plots with median. * $p<0.05$ by Mann-Whitney U test. FIG. 4F depicts a dot plot showing the percentage of AH-1-specific $CD8^+$ T-cells extracted from the metastatic distant tumors in the CT26 tumor-bearing mice. Four mice were in the saline treatment arm and five mice were in the MBTA treatment arm. MBTA-treated mice had more AH-1-specific (AH-1/H-2Ld-tetramer reactive) $CD8^+$ T-cells in the distant tumor than the saline-treated mice did. Data is shown as individual plots with median. $p=0.06$ by Mann-Whitney U test.

FIG. 5A depicts a cartoon schematic of the development of the rCT26-MBTA vaccine. FIG. 5B depicts a bar graph showing the percentage of apoptotic CT26 cells after irradiation. CT26 cell s were irradiated with 50 Gy. Three days after irradiation, >20% of irradiated CT26 cells were in an early stage of apoptosis (PI−/Annexin V+). Ten days after irradiation, >70% of irradiated CT26 cells had entered a late stage of apoptosis (PI+/Annexin V+). Data are shown as mean±SEM. FIG. 5C depicts a schematic timeline of the rCT26-MBTA vaccination. FIG. 5D depicts tumor growth curves in the CT26 tumor-bearing mice injected with saline (left), the rCT26 vaccine (middle), or the combination of the rCT26 vaccine and MBTA (right). The tumors in the mice vaccinated with the rCT26 and MBTA combination grew significantly slower than those in saline-treated or rCT26-vaccinated mice. FIG. 5E depicts cumulative survival curves of the mice in FIG. 5D. By day 30, all saline-treated and rCT26-vaccinated mice died by day 30, while only 25% of mice vaccinated with the rCT26 and MBTA combination died. At least 10% survived 100 days post vaccination. By Log-rank (Mantel-Cox) test with Tukey-Kramer post hoc test: Saline versus rCT26-MBTA treatment ( $p=0.0071$); rCT26 versus rCT26-MBTA treatment ( $p=0.0034$); saline versus rCT26 treatment ($p=0.9846$). FIG. 5F depicts a dot plot showing the percentage of AH-1-specific $CD8^+$ T-cells extracted from whole blood of the CT26 tumor-bearing mice with saline treatment, rCT26 vaccination, and rCT26-MBTA vaccination. rCT26-MBTA-treated mice had significantly more AH-1-specific (AH-1/H-2Ld-tetramer reactive) $CD8^+$ T-cells in the blood than the saline or rCT26 treated mice did. Data is shown as individual plots with median. ** $p<0.01$ by Kruskal-Wallis test.

FIG. 6A shows tumor growth curves of naïve mice (n=4, left) and mice cured of CT26 carcinoma (n=4, right) when challenged with CT26 tumor cells. The latter mice did not show any significant growth of CT26 tumors. FIG. 6B shows cumulative survival curves of mice in FIG. 6A. By 35 days post tumor inoculation, all naïve mice died, while all mice previously cured of CT26 carcinoma survived 100 days post tumor inoculation. ** $p=0.0069$ by Log-rank (Mantel-Cox) test. FIG. 6C shows presentative bioluminescence images of intracranially re-challenged mice. Mice cured of CT26 colon carcinoma were also re-challenged intracranially with 1×10^4 CT26-Luc cells in the right frontal lobe (1 mm rostral of the bregma, 2 mm right of midline and 2 mm deep from the skull surface). MBTA-Pre-treated (left, n=4) and Naïve (right, n=4). FIG. 6D shows cumulative survival curves of intracranially re-challenged mice over time. By 35 days post tumor inoculation, all naïve mice died, while all mice previously cured of CT26 carcinoma survived 100 days post tumor inoculation. Naïve versus MBTA pre-treated mice: * $p=0.0100$ by Log-rank (Mantel-Cox) test.

DETAILED DESCRIPTION OF THE INVENTION

Figure 1A:
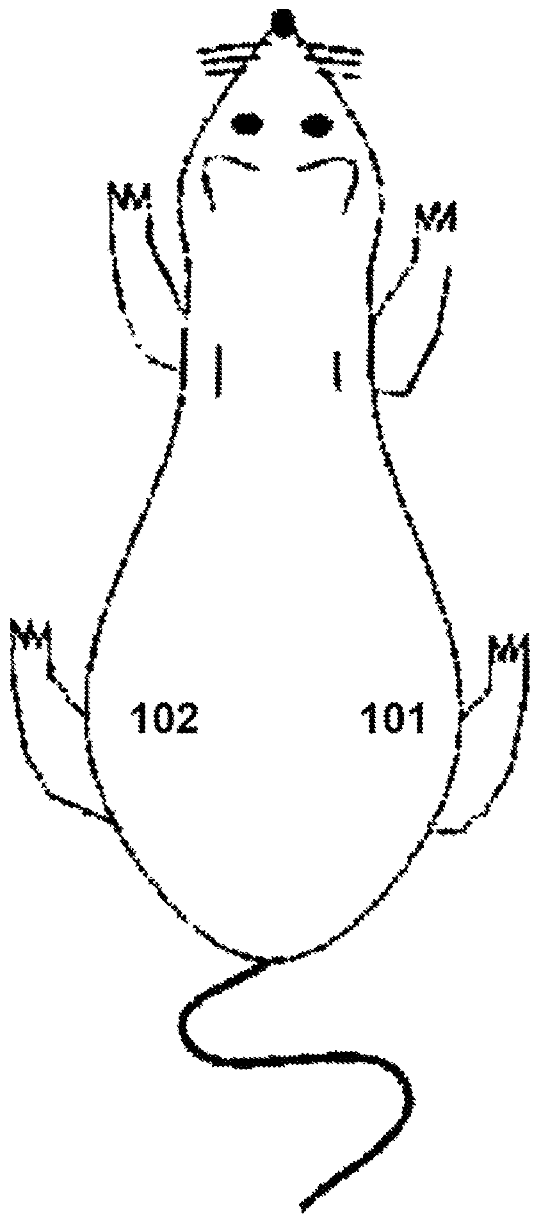
FIGS. 1A-B show a mouse model of subcutaneous primary and metastatic distant tumors.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

DEFINITIONS

The terms "cell," "cells," and "cell population," as used interchangeably, refer to one or more mammalian cells. The term includes progeny of a cell or cell population. Those skilled in the art will recognize that "cells" include progeny of a single cell, and there are variations between the progeny and its original parent cell due to natural, accidental, or deliberate mutation and/or change.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell," and encompasses cancer cells of a solid tumor and a liquid tumor.

"Immunotherapy" as used herein refers to treatment of a disease (e.g., cancer) by modulating an immune response. In the context of the present application, immunotherapy refers to providing an anti-cancer immune response in a subject by administration of a personalized tumor vaccine that elicits an anti-tumor immune response in the subject.

An "effective amount" is an amount sufficient to effect beneficial or desired clinical results. An effective amount can be administered in one or more administrations. For purposes of this application, an effective amount of reagent antibodies is an amount that is sufficient to diagnose, palliate, ameliorate, stabilize, reverse, slow or delay the progression of the disease state.

A "TLR" refers to a toll-like receptor of any species origin, e.g., human and rodent. Examples of TLR thereof include TLR1, TLR2, TLR3, TLR4, TLR5, TLR6, TLR7, TLR8, TLR9, TLR 10 and TLR11.

A "TLR agonist" refers to a molecule that acts as an agonist of at least one TLR.

A "CD40 agonist" herein refers to a molecule that functions as a CD40 agonist signal such as a CD40 agonistic antibody (e.g., an anti-CD40 monoclonal antibody). It can also refer to a CD40L polypeptide, fragment, or conjugate thereof. In general, ligands that bind CD40 may act as a CD40 agonist. Also, CD40 agonists according to the invention may include aptamers that bind CD40.

The term "pathogen associated molecular pattern" or "PAMP," as used herein, refers to any component of a microorganism that directs the targeted host cell to distinguish "self" from "non-self", e.g., infected pathogen, and promotes signals associated with innate immunity.

The term "damage/danger associated molecular pattern" or "DAMP," as used herein, refers to any molecule from damaged or dying cells that activates the innate immune system to target these damaged cells from undamaged cells.

The term "solid tumor" or "solid cancer" as used herein refers to tumors that usually do not contain cysts or liquid areas. Solid tumors can include brain and other central nervous system tumors (including but not limited to tumors of the meninges, brain, spinal cord, cranial nerves and other parts of central nervous system, e.g. glioblastomas or medulla blastomas); head and/or neck cancer; breast tumors; circulatory system tumors (including but not limited to heart, mediastinum and pleura, and other intrathoracic organs, vascular tumors and tumor-associated vascular tissue); excretory system tumors (including but not limited to tumors of kidney, renal pelvis, ureter, bladder, other and unspecified urinary organs); gastrointestinal tract tumors (including but not limited to tumors of esophagus, stomach, small intestine, colon, colorectal, rectosigmoid junction, rectum, anus and anal canal, tumors involving the liver and intrahepatic bile ducts, gall bladder, other and unspecified parts of biliary tract, pancreas, other and digestive organs); oral cavity tumors (including but not limited to tumors of lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (including but not limited to tumors of vulva, vagina, Cervix uteri, Corpus uteri, uterus, ovary, and other sites associated with female genital organs, placenta, penis, prostate, testis, and other sites associated with male genital organs); respiratory tract tumors (including but not limited to tumors of nasal cavity and middle ear, accessory sinuses, larynx, trachea, bronchus and lung, e.g. small cell lung cancer or non-small cell lung cancer); skeletal system tumors (including but not limited to tumors of bone and articular cartilage of limbs, bone articular cartilage and other sites); skin tumors (including but not limited to malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

The term "liquid cancer" or "liquid tumor" as used herein refers to cancer cells that are present in body fluids, such as blood, lymph and bone marrow. Liquid cancers include leukemia, myeloma, myelodysplastic syndrome (MDS), and liquid lymphomas. Liquid lymphomas include lymphomas that contain cysts or liquid areas. Liquid cancers as used herein do not include solid tumors, such as sarcomas and carcinomas or solid lymphomas that do not contain cysts or liquid areas.

An "attenuated" cell as used herein refers to a cell that is alive but replication deficient. The attenuated cell may be alive but unable to complete its cell-cycle. The attenuated cell may have a limited capacity to replicate, express proteins, and to develop through some life cycle stages, for example, an attenuated cell may be arrested at a particular life cycle stage and is unable to developmentally progress beyond that stage.

The term "attenuated cancer cell" as used herein refers to a cancer cell that is attenuated and with reduced oncogenicity. The attenuated cancer cell may be unable to cause or give rise to a tumor. The attenuated cancer cell may also be unable to metastasize or increase a tumor burden of a subject with the tumor. The attenuated cancer cell may comprise damages in their DNA. The attenuated cancer cell can be obtained by various means, for example, by physical and chemical treatments. The attenuated cancer cell can be obtained by irradiation treatments.

The term "personalized tumor vaccine" as used herein refers to a tumor vaccine that can direct a subject-specific immune response to a tumor of a subject. Such a response may be specific to a specific type of tumor from a specific subject. The personalized tumor vaccine as used herein comprises attenuated cancer cells. The personalized tumor vaccine may elicit an adaptive immune response to a tumor or tumor cells of a subject.

Personalized Tumor Vaccine Formulations and Compositions

The immunotherapeutic strategy, introduced in this invention, leverages the use of phagocytosis stimulating agents and immunostimulatory adjuvants for directing an immune response against a subject-specific cancer or cancer cells. The personalized tumor vaccine described here having immunotherapeutic potential delivered as part of a whole attenuated cancer cell vaccine generates a potent adaptive immune response capable of preventing or controlling tumor growth and inducing tumor regression in a subject-specific subset of primary or metastatic tumors. Personalized tumor vaccines are used to train the immune system to find and destroy, attack, kill, or inhibit subject-specific cancer cells.

In some instances, a personalized tumor vaccine can direct the immune system of a subject to target subject-specific cancer cells. In some cases, a personalized tumor vaccine can direct the immune system of a subject to discriminate subject-specific cancer cells from other cancer cells not of the same subject. In some cases, a personalized tumor vaccine can direct the immune system of a subject to discriminate subject-specific cancer cells from cancer cells of other subjects. Such vaccine can make use of a phagocytosis stimulating agent or agents specific to the subject-specific cancer cells. A phagocytosis stimulating agent or agents can allow the immune system to discriminate the subject-specific cancer cells from the non-cancer cells, cancer cells from other tumors, or cancer cells from other subjects. When an immune system is presented with a phagocytosis stimulating agent or agents specific of a subject-specific cancer, the immune system will be activated to target the cancer cells sharing the same subject-specificity, even if a cancer is not present. Such activation of the immune system will create long lasting subject-specific immune memory. When the immune system encounters a cancer with the same or similar subject-specificity in the future, it will immediately activate a subject-specific immune response against the cancer cell.

A personalized tumor vaccine can be a prophylactic or preventative vaccine. A personalized tumor vaccine can be a therapeutic or treatment vaccine. In some embodiments, a personalized tumor vaccine can be administered to a subject in need thereof before the subject is diagnosed with a cancer. In some embodiments, a personalized tumor vaccine can be administered to a subject in need thereof after the subject is diagnosed with a cancer.

A personalized tumor vaccine can comprise a phagocytosis stimulating agent or derivative herein and thereof; an immunostimulatory adjuvant or derivative herein and thereof; and an attenuated cancer cell, cell population or derivative herein and thereof.

In some instances, a personalized tumor vaccine can comprise a phagocytosis stimulating agent or derivative herein and thereof; an immunostimulatory adjuvant or derivative herein and thereof; and from about 1.0×10^3 to about 1.0×10^7 attenuated cancer cells. In some instances, a personalized tumor vaccine can comprise a mannan; an immunostimulatory adjuvant or derivative herein and thereof; and an attenuated cancer cell, cell population or derivative herein and thereof. In some instances, a personalized tumor vaccine can comprise about 2 mg/dose to about 200 mg/dose mannan; an immunostimulatory adjuvant or derivative herein and thereof; and an attenuated cancer cell, cell population or derivative herein and thereof. In some cases, a personalized tumor vaccine can comprise a phagocytosis stimulating agent or derivative herein and thereof conjugated to biocompatible anchor for cell membrane (BAM); an immunostimulatory adjuvant or derivative herein and thereof; and an attenuated cancer cell, cell population or derivative herein and thereof. In some cases, a personalized tumor vaccine can comprise a mannan conjugated to BAM an immunostimulatory adjuvant or derivative herein and thereof; and an attenuated cancer cell, cell population or derivative herein and thereof. In some cases, a personalized tumor vaccine can comprise a mannan conjugated to from about 0.2 mg/dose to about 20 mg/dose BAM; an immunostimulatory adjuvant or derivative herein and thereof; and an attenuated cancer cell, cell population or derivative herein and thereof. In some cases, a personalized tumor vaccine can comprise a mannan conjugated to BAM comprising Formula I described herein and thereof; an immunostimulatory adjuvant or derivative herein and thereof; and an attenuated cancer cell, cell population or derivative herein and thereof.

In some instances, a personalized tumor vaccine can comprise a phagocytosis stimulating agent or derivative herein and thereof; a Toll like receptor (TLR) agonist; and an attenuated cancer cell, cell population or derivative herein and thereof. In some cases, a personalized tumor vaccine can comprise a phagocytosis stimulating agent or derivative herein and thereof; R-848, poly(I:C), lipoteichoic acid (LTA), or combinations thereof; and an attenuated cancer cell, cell population or derivative herein and thereof. In some cases, a personalized tumor vaccine can comprise a phagocytosis stimulating agent or derivative herein and thereof; from about 0.05 mg/dose to about 5 mg/dose R-848, poly(I:C), lipoteichoic acid (LTA), or combinations thereof; and an attenuated cancer cell, cell population or derivative herein and thereof. In some cases, a personalized tumor vaccine can comprise a phagocytosis stimulating agent or derivative herein and thereof; R-848, from about 0.05 mg/dose to about 5 mg/dose poly(I:C), lipoteichoic acid (LTA), or combinations thereof; and an attenuated cancer cell, cell population or derivative herein and thereof. In some cases, a personalized tumor vaccine can comprise a phagocytosis stimulating agent or derivative herein and thereof; R-848, poly(I:C), from about 0.05 mg/dose to about 5 mg/dose lipoteichoic acid (LTA), or combinations thereof; and an attenuated cancer cell, cell population or derivative herein and thereof.

In some instances, a personalized tumor vaccine can comprise a phagocytosis stimulating agent or derivative herein and thereof; an anti-CD40 antibody; and an attenuated cancer cell, cell population or derivative herein and thereof. In some instances, a personalized tumor vaccine can comprise a phagocytosis stimulating agent or derivative herein and thereof; from about 0.04 mg/dose to about 4 mg/dose anti-CD40 antibody; and an attenuated cancer cell, cell population or derivative herein and thereof.

In some instances, a personalized tumor vaccine can comprise a mannan attached to BAM, a R-848, a poly(I:C), an LTA, an anti-CD40 antibody, and irradiated cancer cells. In some instances, a personalized tumor vaccine can comprise from about 0.05 mg/dose to about 5 mg/dose mannan attached to from about 0.05 mg/dose to about 5 mg/dose BAM, from about 0.05 mg/dose to about 5 mg/dose R-848, from about 0.05 mg/dose to about 5 mg/dose poly(I:C), from about 0.05 mg/dose to about 5 mg/dose LTA, from about 0.04 mg/dose to about 4 mg/dose anti-CD40 antibody, and from about 1.0×10^3 to about 1.0×10^7 irradiated cancer cells.

Phagocytosis Stimulating Agents

A personalized tumor vaccine described herein and thereof can comprise one phagocytosis stimulating agent. In some instances, a phagocytosis stimulating agent can comprise a nucleic acid, amino acid, nucleotide, carbohydrate, lipid, small molecule, ion, compound, any derivatives herein and thereof, or any combinations herein and thereof. In some embodiments, a phagocytosis stimulating agent may not be expressed by a cancer cell. In some cases, a phagocytosis stimulating agent can be exogenous to a cancer cell. In some instances, a phagocytosis stimulating agent can be specific to a cancer cell. In some instances, a phagocytosis stimulating agent may not be specific to a cancer cell.

In some instances, a phagocytosis stimulating agent can be linked to an attenuated cancer cell. In some instances, a phagocytosis stimulating agent can be attached to an attenuated cancer cell. In some instances, a phagocytosis stimulating agent can comprise a PAMP or DAMP described herein or thereof.

The innate immune response, including phagocytosis, relies on recognition of pathogen-associated molecular patterns (PAMPs), a group of evolutionarily conserved structures on pathogens. PAMPs can comprise secretory molecules, extracellular molecules, or intracellular molecules. PAMPs can activate pattern-recognition receptors, such as Toll-like receptors (TLRs), to trigger antimicrobial and proinflammatory response against the pathogens. Such responses include differential gene expression, production of cytokines, chemokines, and/or phagocytosis. In some instances, another type of innate immune response-stimulatory agents comprise Danger-Associated Molecular Patterns (DAMP), molecular patterns, structures, or entities associated with stressed, injured, infected, or transformed cells not found in normal cells. A phagocytosis stimulating agent can comprise a PAMP or DAMP molecule that, when recognized by an immune system, triggers a phagocytosis response against the phagocytosis stimulating agent or any molecule or cell linked to the phagocytosis stimulating agent.

A phagocytosis stimulating agent can have an origin in viruses, gram-positive bacteria, gram-negative bacteria, fungi, protozoa, protists, nematodes, plant cells, animal cells, any derivatives herein and thereof, or any combinations herein and thereof. A phagocytosis stimulating agent can also be synthesized in vitro, such as but not limited to organic synthesis. A phagocytosis stimulating agent can be an intracellular, extracellular, lysosomal, endosomal, nuclear, cytoplasmic, mitochondrial, ER-bound, Golgi-bound, membrane-associated, or integrated membrane component. In some cases, a phagocytosis stimulating agent can also comprise triacyl lipopeptide, diacyl lipopeptide, lipoteichoic acid, lipoprotein, peptidoglycan, lipoarabinomannan, porin, envelope glycoprotein, GPI-mucin, phospholipomannan, zymosan, beta-glycan double-stranded (ds) RNA, double-stranded DNA, single-stranded (ss) RNA, single-stranded DNA, lipopolysaccharide, arabinogalactan, glycoinositolphospholipid, heat shock proteins (HSPs), flagellin, CpG DNA, methylated DNA, 5'-triphosphate RNA, diaminopimelic acid, triacyl lipopeptides, muramyl dipeptide (MDP), surface glycoprotein (GP), membrane components, lipoteichoic acid (LTA), phosphorylcholine (PC), PE, PI, mycolic acid, adenosine triphosphate (ATP), adenosine diphosphate (ADP) adenosine monophosphate (AMP), guanosine triphosphate (GTP), uridine triphosphate (UTP), thymidine triphosphate (TTP), cytidine triphosphate (CTP), GDP, UDP, TDP, CDP, GMP, UMP, CMP, uric acid crystals, phosphatidyinositol mannosides (PIM), endotoxin, wall teichoic acid (WTA), LTA, N-formylmethionine, carbohydrates, glucan, chitin, hamagglutinin, F-protein, phenol-soluble modulin, hemozoin, any derivatives herein and thereof, or any combinations herein and thereof. A dsDNA can be long or short. CpG DNA can comprise methylated or unmethylated CpG DNA. Arabinogalactan can comprise D-arabinose or D-galactose. A phagocytosis stimulating agent can comprise glucan or mannan. As provided herein, a phagocytosis stimulating agent can comprise mannan or its derivatives.

Mannan

Mannan is often found on the yeast cell wall. It can comprise a series of mannose units linked by alpha (1-6) linkages. Mannan can also have alpha (1-2) and alpha (1-3) branched linkages. Detection of mannan leads to cell lysis or phagocytosis in the mannan-binding lectin (MBL) pathway. Mannans can also be found in plants, algae, fungus, or bacteria. They are synthesized from activated nucleotide sugars such as GDP-mannose, GDP-glucose, and UDP-galactose. Glycosyltransferases, localized in Golgi, utilize the activated nucleotide sugars to synthesize the polymer by facilitating the linkage between mannose monomers.

Mannan can comprise the polysaccharide moiety of glycoproteins. Mannan can comprise a linear, branched, or a linear and branched polymer of linked mannose resides or molecules. In some cases, mannan can have beta (1-4) linkages.

Mannan can be cytoplasmic or extracellular. Mannan can have a molecular weight of 666.6 g/mol. In some embodiments, mannan can have 14 hydrogen bond donors and 21 acceptors. In other cases, mannan can have 10 rotatable bonds. In some instances, mannan can have a monoisotopic mass of 666.221858 g/mol. In other cases, mannan can have a topological polar surface area of 348 Å2. In some cases, mannan can have 45 heavy atoms and 0 formal charge. In some embodiments, mannan can be (2S,3S,4S,5S,6R)-2-[(2R,3S,4R,5R,6S)-6-[(2R,3S,4R,5S,6S)-4,5-dihydroxy-2-(hydroxymethyl)-6-[(2R,3R,4R,5S,6R)-4,5,6-trihydroxy-2-(hydroxymethyl) oxan-3-yl]oxyoxan-3-yl]oxy-4,5-dihydroxy-2-(hydroxymethyl) oxan-3-yl]oxy-6-(hydroxymethyl) oxane-3,4,5-triol. In some cases, mannan can be $C_{24}H_{42}O_{21}$.

Manan can comprise a backbone of alpha (1-6) linked mannose unites with alpha (1-2) and alpha (1-3) linked side chains. The side chains can have 0, 1, 2, 3, 4, 5, 6, 7, 8, 9, 10, or more sugar units in length. In some embodiments, a side chain can comprise a mannan-oligosaccharide (MOS). A mannose can be a D-mannose or L-mannose. A mannose can have a molecular formula of $C_6H_{12}O_6$. In some embodiments, a mannose can have a molecular weight of 180.16 g/mol. In other cases, a mannose can comprise a D-mannohexopyranose. A mannose can also be (3S,4S,5S,6R)-6-(hydroxymethyl) oxane-2,3,4,5-tetrol. A mannose can comprise two different-sized rings, a six-membered pyranose form and a five-membered furanose form. In some instances, a ring can have an alpha or beta configuration at the anomeric position.

Mannan can be synthesized by yeast. Mannan-producing yeasts can comprise *Hansenula holstii, Rhodotorula acheniorum, Sporobolomyces salmonicolor, Saccharomyces cerevisiae, Candida albicans, Schizosaccharomyces pombe, Meyerozyma guilliermondii*, Brewers dried yeast, or *Candida utilis*. Mannan can be synthesized by plants. Mannan-producing plants can comprise the Ebenaceae family, *Arabidopsis thaliana*, the Leguminoseae family, *Caesalpinia spinosa* Kuntze, the Annonaceae family, *Amorphophallus konjac, Ceratonia siliqua*, the Convolvulaceae family, *Cyamopsis tetragonoloba*, the Loganiaceae family, *Senna tora, Trigonella foenum-graecum* L., the Palmae family, *Picea abies, Cercis siliquastrum*, or *Nicotiana plumbaginifolia*. Other mannan-producing organisms can comprise *Porphyra umbilicalis, Acetabularia acetabulum, Charophyceae, Dactylium dendroides, Pseudocyphellaria clathrata, Pseudomonas mutabilis, Pseudomonas syringae* pv. *ciccaronei, Edwardsiella tarda, Pseudomonas aeruginosa*, or *Brevibacillus thermoruber*.

Biocompatible Anchors for Membrane (BAMs)

A phagocytosis stimulating agent can comprise a linker that link the phagocytosis stimulating agent to an attenuated cancer cell by a linker. A linker can comprise a chemical linkage, physical linkage, association, attachment, connection, junction, placement, fusion, interaction, ligation, chemical bond, physical bond, crosslink, joint, coupling, clamping, tie, or any derivatives herein and thereof, or any combinations herein and thereof. A linker can comprise a chemical or physical linker. A chemical linker can comprise a membrane linker. A membrane linker can comprise a myristate, palmitate, farnesyl, geranylgeranyl, oleate, isoprenoid, fatty acid, diacylglycerol, long-chain acyl group, long-chain prenyl group, cholesterol, stearyl, phosphatidylethanolamine (PE), phosphatidylinositol (PI), glycosyl phosphatidyl inositol (GPI) anchor, chelator lipid anchor, polypeptide, derivatives herein and thereof, or any combinations herein and thereof. A chelator lipid anchor can comprise nitrilotriacetic acid ditetradecylamine (NTA-DTDA).

A linker can also comprise Biocompatible Anchors for Membrane (BAM). A BAM can comprise a lipid anchor. A lipid anchor can comprise any lipid anchors described herein and thereof. BAM can comprise a lipid anchor and a Polyethylene glycol (PEG) chain. BAM can be used to link a chemical, molecule, polypeptide, nucleic acid, lipid, carbohydrate, any moieties described herein and thereof, any derivatives herein and thereof, any combinations herein and thereof to a cell.

In some cases, BAM can comprise an NHS reactive ester group. In other cases, a PEG chain can be hydrophilic. In some embodiments, BAM can comprise a succinylated poly(ethylene glycol). oleyl ether at the hydroxyl end of a PEG chain. In other cases, BAM can comprise a N-hydroxysuccinimide (NHS) at the succinyl PEG end. In some cases, BAM comprising an NHS end can bind most proteins. In some cases, a BAM can comprise a Oleyl-O-poly(ethylene glycol)-succinyl-N-hydroxy-succinimidyl esters. In some cases, BAM can comprise Formula I (Oleyl-O$(CH_2CH_2)_n$ CO—$CH_2CH_2$—COO—NHS):

Formula I

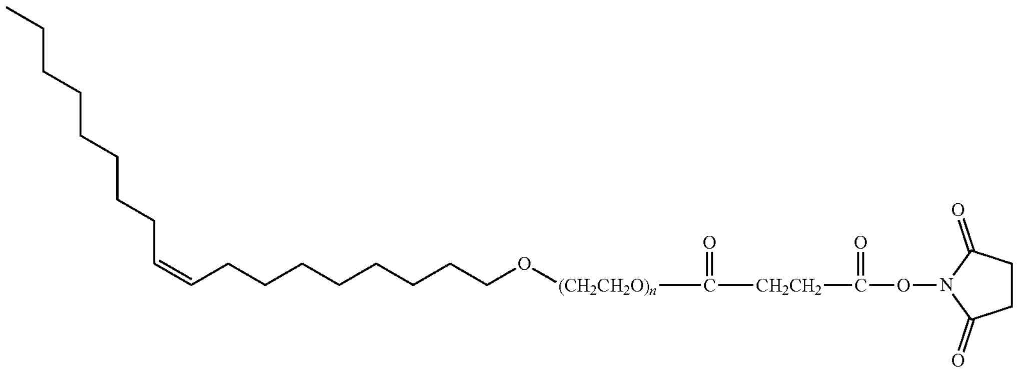

Wherein n can comprise the number of ethylene oxide (EO) unit repeats in the PEG moiety.

In some embodiments, n can be from 1-500, In some cases, the number of EO unit repeats in the PEG moiety can be from 0 to 9, from 1 to 10, from 2 to 11, from 3 to 12, from 4 to 13, from 5 to 14, from 6 to 15, from 7 to 16, from 8 to 17, from 9 to 18, from 10 to 19, from 11 to 20, from 12 to 21, from 13 to 22, from 14 to 23, from 15 to 24, from 16 to 25, from 17 to 26, from 18 to 27, from 19 to 28, from 20 to 29, from 21 to 30, from 22 to 31, from 23 to 32, from 24 to 33, from 25 to 34, from 26 to 35, from 27 to 36, from 28 to 37, from 29 to 38, from 30 to 39, from 31 to 40, from 32 to 41, from 33 to 42, from 34 to 43, from 35 to 44, from 36 to 45, from 37 to 46, from 38 to 47, from 39 to 48, from 40 to 49, from 41 to 50, from 42 to 51, from 43 to 52, from 44 to 53, from 45 to 54, from 46 to 55, from 47 to 56, from 48 to 57, from 49 to 58, from 50 to 59, from 51 to 60, from 52 to 61, from 53 to 62, from 54 to 63, from 55 to 64, from 56 to 65, from 57 to 66, from 58 to 67, from 59 to 68, from 60 to 69, from 61 to 70, from 62 to 71, from 63 to 72, from 64 to 73, from 65 to 74, from 66 to 75, from 67 to 76, from 68 to 77, from 69 to 78, from 70 to 79, from 71 to 80, from 72 to 81, from 73 to 82, from 74 to 83, from 75 to 84, from 76 to 85, from 77 to 86, from 78 to 87, from 79 to 88, from 80 to 89, from 81 to 90, from 82 to 91, from 83 to 92, from 84 to 93, from 85 to 94, from 86 to 95, from 87 to 96, from 88 to 97, from 89 to 98, from 90 to 99, from 91 to 100, from 92 to 101, from 93 to 102, from 94 to 103, from 95 to 104, from 96 to 105, from 97 to 106, from 98 to 107, from 99 to 108, from 100 to 109, from 101 to 110, from 102 to 111, from 103 to 112, from 104 to 113, from 105 to 114, from 106 to 115, from 107 to 116, from 108 to 117, from 109 to 118, from 110 to 119, from 111 to 120, from 112 to 121, from 113 to 122, from 114 to 123, from 115 to 124, from 116 to 125, from 117 to 126, from 118 to 127, from 119 to 128, from 120 to 129, from 121 to 130, from 122 to 131, from 123 to 132, from 124 to 133, from 125 to 134, from 126 to 135, from 127 to 136, from 128 to 137, from 129 to 138, from 130 to 139, from 131 to 140, from 132 to 141, from 133 to 142, from 134 to 143, from 135 to 144, from 136 to 145, from 137 to 146, from 138 to 147, from 139 to 148, from 140 to 149, from 141 to 150, from 142 to 151, from 143 to 152, from 144 to 153, from 145 to 154, from 146 to 155, from 147 to 156, from 148 to 157, from 149 to 158, from 150 to 159, from 151 to 160, from 152 to 161, from 153 to 162, from 154 to 163, from 155 to 164, from 156 to 165, from 157 to 166, from 158 to 167, from 159 to 168, from 160 to 169, from 161 to 170, from 162 to 171, from 163 to 172, from 164 to 173, from 165 to 174, from 166 to 175, from 167 to 176, from 168 to 177, from 169 to 178, from 170 to 179, from 171 to 180, from 172 to 181, from 173 to 182, from 174 to 183, from 175 to 184, from 176 to 185, from 177 to 186, from 178 to 187, from 179 to 188, from 180 to 189, from 181 to 190, from 182 to 191, from 183 to 192, from 184 to 193, from 185 to 194, from 186 to 195, from 187 to 196, from 188 to 197, from 189 to 198, from 190 to 199, from 191 to 200, from 192 to 201, from 193 to 202, from 194 to 203, from 195 to 204, from 196 to 205, from 197 to 206, from 198 to 207, from 199 to 208, from 200 to 209, from 201 to 210, from 202 to 211, from 203 to 212, from 204 to 213, from 205 to 214, from 206 to 215, from 207 to 216, from 208 to 217, from 209 to 218, from 210 to 219, from 211 to 220, from 212 to 221, from 213 to 222, from 214 to 223, from 215 to 224, from 216 to 225, from 217 to 226, from 218 to 227, from 219 to 228, from 220 to 229, from 221 to 230, from 222 to 231, from 223 to 232, from 224 to 233, from 225 to 234, from 226 to 235, from 227 to 236, from 228 to 237, from 229 to 238, from 230 to 239, from 231 to 240, from 232 to 241, from 233 to 242, from 234 to 243, from 235 to 244, from 236 to 245, from 237 to 246, from 238 to 247, from 239 to 248, from 240 to 249, from 241 to 250, from 242 to 251, from 243 to 252, from 244 to 253, from 245 to 254, from 246 to 255, from 247 to 256, from 248 to 257, from 249 to 258, from 250 to 259, from 251 to 260, from 252 to 261, from 253 to 262, from 254 to 263, from 255 to 264, from 256 to 265, from 257 to 266, from 258 to 267, from 259 to 268, from 260 to 269, from 261 to 270, from 262 to 271, from 263 to 272, from 264 to 273, from 265 to 274, from 266 to 275, from 267 to 276, from 268 to 277, from 269 to 278, from 270 to 279, from 271 to 280, from 272 to 281, from 273 to 282, from 274 to 283, from 275 to 284, from 276 to 285, from 277 to 286, from 278 to 287, from 279 to 288, from 280 to 289, from 281 to 290, from 282 to 291, from 283 to 292, from 284 to 293, from 285 to 294, from 286 to 295, from 287 to 296, from 288 to 297, from 289 to 298, from 290 to 299, from 291 to 300, from 292 to 301, from 293 to 302, from 294 to 303, from 295 to 304, from 296 to 305, from 297 to 306, from 298 to 307, from 299 to 308, from 300 to 309, from 301 to 310, from 302 to 311, from 303 to 312, from 304 to 313, from 305 to 314, from 306 to 315, from 307 to 316, from 308 to 317, from 309 to 318, from 310 to 319, from 311 to 320, from 312 to 321, from 313 to 322, from 314 to 323, from 315 to 324, from 316 to 325, from 317 to 326, from 318 to 327, from 319 to 328, from 320 to 329, from 321 to 330, from 322 to 331, from 323 to 332, from 324 to 333, from 325 to 334, from 326 to 335, from 327 to 336, from 328 to 337, from 329 to 338, from 330 to 339, from 331 to 340, from 332 to 341, from 333 to 342, from 334 to 343, from 335 to 344, from 336 to 345, from 337 to 346, from 338 to 347, from 339 to 348, from 340 to 349, from 341 to 350, from 342 to 351, from 343 to 352, from 344 to 353, from 345 to 354, from 346 to 355, from 347 to 356, from 348 to 357, from 349 to 358, from 350 to 359, from 351 to 360, from 352 to 361, from 353 to 362, from 354 to 363, from 355 to 364, from 356 to 365, from 357 to 366, from 358 to 367, from 359 to 368, from 360 to 369, from 361 to 370, from 362 to 371, from 363 to 372, from 364 to 373, from 365 to 374, from 366 to 375, from 367 to 376, from 368 to 377, from 369 to 378, from 370 to 379, from 371 to 380, from 372 to 381, from 373 to 382, from 374 to 383, from 375 to 384, from 376 to 385, from 377 to 386, from 378 to 387, from 379 to 388, from 380 to 389, from 381 to 390, from 382 to 391, from 383 to 392, from 384 to 393, from 385 to 394, from 386 to 395, from 387 to 396, from 388 to 397, from 389 to 398, from 390 to 399, from 391 to 400, from 392 to 401, from 393 to 402, from 394 to 403, from 395 to 404, from 396 to 405, from 397 to 406, from 398 to 407, from 399 to 408, from 400 to 409, from 401 to 410, from 402 to 411, from 403 to 412, from 404 to 413, from 405 to 414, from 406 to 415, from 407 to 416, from 408 to 417, from 409 to 418, from 410 to 419, from 411 to 420, from 412 to 421, from 413 to 422, from 414 to 423, from 415 to 424, from 416 to 425, from 417 to 426, from 418 to 427, from 419 to 428, from 420 to 429, from 421 to 430, from 422 to 431, from 423 to 432, from 424 to 433, from 425 to 434, from 426 to 435, from 427 to 436, from 428 to 437, from 429 to 438, from 430 to 439, from 431 to 440, from 432 to 441, from 433 to 442, from 434 to 443, from 435 to 444, from 436 to 445, from 437 to 446, from 438 to 447, from 439 to 448, from 440 to 449, from 441 to 450, from 442 to 451, from 443 to 452, from 444 to 453, from 445 to 454, from 446 to 455, from 447 to 456, from 448 to 457, from 449 to 458, from 450 to 459, from 451 to 460, from 452 to 461, from 453 to 462, from 454 to 463, from 455 to 464, from 456 to 465, from 457 to 466, from 458 to 467, from 459 to 468, from 460 to 469, from 461 to 470, from 462 to 471, from 463 to 472, from 464 to 473, from 465 to 474, from 466 to 475, from 467 to 476, from 468 to 477, from 469 to 478, from 470 to 479, from 471 to 480, from 472 to 481, from 473 to 482, from 474 to 483, from 475 to 484, from 476 to 485, from 477 to 486, from 478 to 487, from 479 to 488, from 480 to 489, from 481 to 490, from 482 to 491, from 483 to 492, from 484 to 493, from 485 to 494, from 486 to 495, from 487 to 496, from 488 to 497, from 489 to 498, from 490 to 499, or from 491 to 500. In some embodiments, the numbers of EO unit repeats in the PEG moiety can be 40. In some embodiments, the numbers of EO unit repeats in the PEG moiety can be 80. In some embodiments, the numbers of EO unit repeats in the PEG moiety can be 90. In some embodiments, the numbers of EO unit repeats in the PEG moiety can be 110.

BAM can comprise a single lipid anchor. BAM can comprise more than one lipid anchors. In some cases, BAM can comprise two lipid anchors. In some embodiments, BAM can comprise 0, 1, 2, 3, 4, 5, 6, 7, 8, 9, 10, 11, 12, 13, 14, 15, 16, 17, 18, 19, or 20 lipid anchors. In some cases, a lipid anchor can comprise a myristate, palmitate, farnesyl, geranylgeranyl, oleate, isoprenoid, fatty acid, diacylglycerol, long-chain acyl group, long-chain prenyl group, cholesterol, stearyl, phosphatidyl-ethanolamine (PE), phosphatidylinositol (PI), glycosyl phosphatidyl inositol (GPI) anchor, chelator lipid anchor, polypeptide, derivatives herein and thereof, or any combinations herein and thereof. A chelator lipid anchor can comprise nitrilotriacetic acid ditetradecylamine (NTA-DTDA). In some embodiments, a lipid anchor can comprise methoxy-poly(ethylene glycol)-succinyl-N-hydroxy-succinimidyl ester. In some cases, a lipid anchor can comprise an oleyl chain. In other cases, a lipid anchor can comprise dioleylphosphatidylethanolamine (DOPE). A DOPE-PEG Bam can be pegylated and succinylated at the hydroxyl end of PEG and modified with N-hydroxysuccinimide (NHS) at the succinyl PEG end.

In some cases, BAM can comprise Formula II.

Formula II

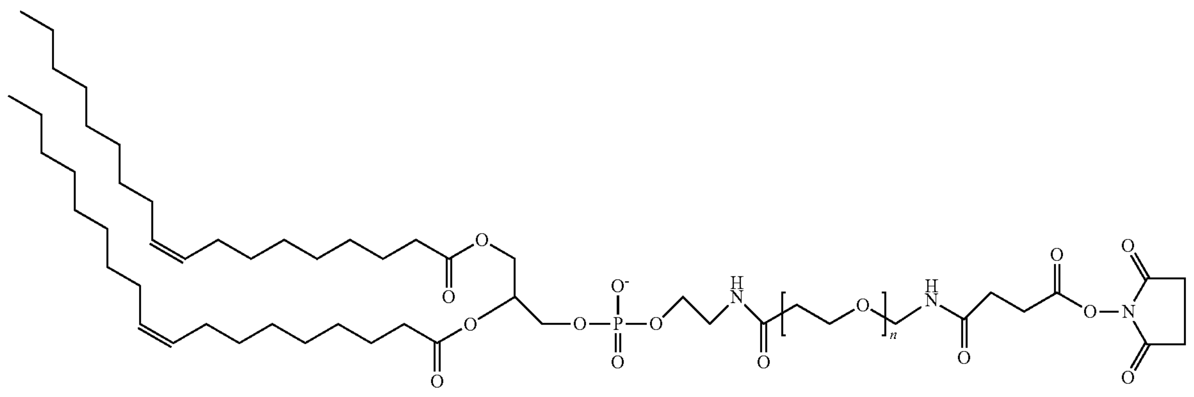

DOPE PEG NHS

Wherein n can comprise the number of ethylene oxide (EO) unit repeats in the PEG moiety.

In some embodiments, BAM can have a concentration of 100 M, 10 M, 1 M, 1x10^-1 M, 1x10^-2 M, 1x10^-3 M, 1x10^-4M, 1x10^-5 M, 1x10^-6 M, 1x10^-7M, 1x10^-8M, 1x10^-9 M, 1x10^-10 M, 1x10^-11 M, 1x10^-12 M, 1x10^-13 M, 1x10^-14 M, 1x10^-15 M, 1x10^-16 M, 1x10^-17 M, 1x10^-18 M, 1x10^-19 M, 1x10^-20 M, 1x10^-21 M, 1x10^-22 M, 1x10^-23 M, 1x10^-24 M, 1x10^-25 M, 1x10^-26 M, 1x10^-27M, 1x10^-28 M, 1x10^-29 M, or 1x10^-30 M in aqueous solution. In other cases, BAM can have a concentration from 9.9x10^-31 M to 1x10^-29 M, from 9.9x10^-30 M to 1x10^-28 M, from 9.9x10^-29 M to 1x10^-27 M, from 9.9x10^-28 M to 1x10^-26 M, from 9.9x10^-27 M to 1x10^-25 M, from 9.9x10^-26 M to 1x10^-24 M, from 9.9x10^-25 M to 1x10^-23 M, from 9.9x10^-24 M to 1x10^-22 M, from 9.9x10^-23 M to 1x10^-21 M, from 9.9x10^-22 M to 1x10^-20 M, from 9.9x10^-21 M to 1x10^-19 M, from 9.9x10^-20 M to 1x10^-18 M, from 9.9x10^-19 M to 1x10^-17 M, from 9.9x10^-18 M to 1x10^-16 M, from 9.9x10^-17 M to 1x10^-15 M, from 9.9x10^-16 M to 1x10^-14 M, from 9.9x10^-15 M to 1x10^-13 M, from 9.9x10^-14 M to 1x10^-12 M, from 9.9x10^-13 M to 1x10^-11 M, from 9.9x10^-12 M to 1x10^-10 M, from 9.9x10^-11 M to 1x10^-9 M, from 9.9x10^-10 M to 1x10^-8 M, from 9.9x10^-9 M to 1x10^-7 M, from 9.9x 10^-8 M to 1x10^-6 M, from 9.9x10^-7 M to 1x10^-5 M, from 9.9x10^-6 M to 1x10^-4 M, from 9.9x10^-5 M to 1x10^-3 M, from 9.9x10^-4 M to 1x10^-2 M, from 9.9x 10^-3 M to 1x10^-1 M, from 9.9x10^-2 M to 1x10^0 M, from 9.9x10^-1 M to 1x10^1 M, or from 9.9x10^0 M to 1x10^2 M in aqueous solution.

BAM can be conjugated to a biotin, fluorescein, polypeptide, chemical, small molecule, nucleic acid, drug compound, polysaccharide, any derivatives herein and thereof, or any combinations herein and thereof. A polysaccharide can comprise monosaccharide or oligosaccharide units bound together by glycosidic linkages. In some instances, a BAM can be conjugated to a mannan. This can be achieved by reacting NHS group of a BAM with a primary amine of another molecule at pH 7-9 to form amide bond. In the case of conjugating mannan to BAM, aminated mannan is prepared by reductive amination. Mannan solution in an environment of ammonium acetate (300 mg/ml) is reduced by 0.2 M sodium cyanoborohydride at pH 7.5 and 50 °C for five days. Solution is further dialyzed using MWCO 3500 dialysis tubing (Serva, Heidelberg, Germany) against PBS at 4 °C overnight. Binding of BAM on amino group of mannan is performed at pH 7.3 according to Kato et al., 2004. During one hour at room temperature N-hydroxysuccinimide (NHS) group of BAM reacts with amino group of mannan. Solutions obtained after dialysis as above are stored frozen at −20 °C until use.

A personalized tumor vaccine can comprise 1x10^0 M, 2x10^0 M, 3x10^0 M, 4x10^0 M, 5x10^0 M, 6x10^0 M, 7x10^0 M, 8x10^0 M, 9x10^0 M, 1x10^-1 M, 2x10^-1 M, 3x10^-1 M, 4x10^-1M, 5x10^-1 M, 6x10^-1 M, 7x10^-1M, 8x10^-1 M, 9x10^-1 M, 1x10^-2 M, 2x10^-2 M, 3x10^-2 M, 4x10^-2 M, 5x10^-2 M, 6x10^-2 M, 7x10^-2 M, 8x10^-2 M, 9x10^-2 M, 1x10^-3 M, 2x10^-3 M, 3x10^-3 M, 4x10^-3 M, 5x10^-3 M, 6x10^-3 M, 7x10^-3 M, 8x10^-3 M, 9x10^-3 M, 1x10^-4 M, 2x10^-4 M, 3x10^-4 M, 4x10^-4 M, 5x10^-4 M, 6x10^-4 M, 7x10^-4 M, 8x10^-4 M, 9x10^-4 M, 1x10^-5 M, 2x10^-5 M, 3x10^-5 M, 4x10^-5 M, 5x10^-5 M, 6x10^-5 M, 7x10^-5 M, 8x10^-5 M, 9x10^-5 M, 1x10^-6 M, 2x10^-6 M, 3x10^-6 M, 4x10^-6 M, 5x10^-6 M, 6x10^-6 M, 7x10^-6 M, 8x10^-6 M, or 9x10^-6 M mannan-BAM. In some cases, a personalized tumor vaccine can comprise from 5x10^0M to 1x10^1 M, from 1x10^0M to 5x10^0 M, from 5x10^-1M to 1x10^0 M, from 1x10^-1M to 5x10^-1 M, from 5x10^-2M to 1x10^-1 M, from 1x10^-2M to 5x10^-2 M, from 5x10^-3M to 1x10^-2 M, from 1x10^-3M to 5x10^-3 M, from 5x10^-4M to 1x10^-3 M, from 1x10^-4M to 5x10^-4 M, from 5x10^-5M to 1x10^-4 M, from 1x10^-5M to 5x10^-5 M, from 5x10^-6M to 1x10^-5 M, from 1x10^-6M to 5x10^-6 M, or from 5x10^-7M to 1x10^-7 M mannan-BAM. A personalized tumor vaccine can also comprise about 0.2 mM mannan-BAM. A personalized tumor vaccine can also comprise about 0.95 mg mannan. A personalized tumor vaccine can also comprise about 0.098 mg BAM. A personalized tumor vaccine can comprise about 23.1 mg/day mannan. A personalized tumor vaccine can also comprise about 2.38 mg/day mannan.

Immunostimulatory Adjuvant

An immunostimulatory adjuvant can comprise any substance that acts to accelerate, prolong, or enhance phagocytosis stimulating agent-specific immune responses when used in combination with a phagocytosis stimulating agent linked to an attenuated cancer cell. In some instances, an immunostimulatory adjuvant can also potentiate, activate, prime, stimulate, or increase an immune response to a phagocytosis stimulating agent linked to an attenuated cancer cell.

A personalized tumor vaccine can comprise one immunostimulatory adjuvant. A personalized tumor vaccine can comprise more than one immunostimulatory adjuvant. A personalized tumor vaccine can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more than 100 immunostimulatory adjuvants. A personalized tumor vaccine can comprise from 1 to 10, from 5 to 15, from 10 to 20, from 15 to 25, from 20 to 30, from 25 to 35, from 30 to 40, from 35 to 45, from 40 to 50, from 45 to 55, from 50 to 60, from 55 to 65, from 60 to 70, from 65 to 75, from 70 to 80, from 75 to 85, from 80 to 90, from 85 to 95, from 90 to 100 immunostimulatory adjuvants. In some cases, a personalized tumor vaccine can comprise 2 immunostimulatory adjuvants. In some cases, a personalized tumor vaccine can comprise 3 immunostimulatory adjuvants. In some cases, a personalized tumor vaccine can comprise 4 immunostimulatory adjuvants.

Since an immunostimulatory adjuvant can engage the immune system by mimicking a phagocytosis stimulating agent, the phagocytosis stimulating agent and the immunostimulatory adjuvant can activate or signal through an overlapping set of receptors in the immune system. In some cases, an immunostimulatory adjuvant can comprise a PAMP or DAMP. In other cases, an immunostimulatory adjuvant can comprise an organic or inorganic immunostimulatory adjuvant. In some instances, an immunostimulatory adjuvant can activate a Toll-like receptor (TLR) by a TLR agonist. In other instances, an immunostimulatory adjuvant can activate a CD40 receptor by an anti-CD40 antibody.

An immunostimulatory adjuvant can comprise any PAMPs, DAMPs, TLR agonists, CD40 agonists, any derivatives herein and thereof, or any combination herein and thereof. In some instances, an immunostimulatory adjuvant can also comprise any nucleic that encodes any PAMPs, DAMPs, TLR agonists, CD40 agonists, any derivatives herein and thereof, or any combination herein and thereof. In some embodiments, an immunostimulatory adjuvant can also comprise any nucleic that encodes a protein that can increase, stimulate, activate, or initiate the production of any PAMPs, DAMPs, TLR agonists, CD40 agonists, any derivatives herein and thereof, or any combination herein and thereof. In some instances, an immunostimulatory adjuvant can comprise LTA, poly(I:C), R-848, anti-CD40 antibody, any derivatives herein and thereof, any combinations herein and thereof.

Toll-Like Receptors (TLRs)

The innate immune response pathway comprises cellular components that recognize the PAMPs or DAMPs. Such cellular components can comprise the Toll pathway and cytoplasmic pathway. The cellular components of innate immunity can comprise antigen-presenting dendritic cells (DCs), phagocytic macrophages and granulocytes, cytotoxic natural killer (NK) cells, and gamma-delta T lymphocytes. These cells use both the Toll pathway and cytoplasmic to recognize the PAMPs or DAMPs to trigger immune response pathway including but not limited to complement activation, phagocytosis, autophagy, and cytokine production secretion.

The Toll pathway uses a class of receptors, TLRs, in the PAMP recognition and immune pathway activation. Upon activation of PAMP, TLRs recruit adaptor proteins to propagate PAMP/antigen-induced signal transduction pathway in the inflammatory response. The TLRs are type I integral membrane receptors, each with an N-terminal ligand recognition domain, a single transmembrane helix, and a C-terminal cytoplasmic signaling domain.

TLRs can comprise TLR1, TLR2, TLR3, TLR4, TLR5, TLR6, TLR7, TLR8, TLR9, TLR10, TLR11, TLR12, TLR13, any derivatives herein and thereof, any combinations herein and thereof. In some embodiments, a TLR can be expressed on the membranes of dendritic cells, macrophages, natural killer cells, T cells, B cells, epithelial cells, endothelial cells, or fibroblasts.

TLRs can be activated by PAMPs or DAMPs described herein and thereof. TLRs can also be activated by small molecules described herein and thereof. Some of the ligands and their TLRs are listed in TABLE 1.

TABLE 1

A list of ligands for TLRs

| TLRs | Ligands | Class |
|---|---|---|
| TLR1 | Triacyl lipopeptides | PAMP |
| TLR2 | Glycolipids | PAMP |
| TLR2 | Lipoteichoic acid | PAMP |
| TLR2 | HSP70 | DAMP |
| TLR2 | Zymosan | PAMP |
| TLR2 | Beta-glucan | PAMP |
| TLR3 | dsRNAs | PAMP |
| TLR3 | Poly (I:C) | PAMP |
| TLR4 | Lipopolysaccharide | PAMP |
| TLR4 | HSPs | PAMP/DAMP |
| TLR4 | Heparan sulfate | DAMP |
| TLR4 | Fibrinogen | DAMP |
| TLR4 | Hyaluronic acid fragments | DAMP |
| TLR4 | Nickel | Chemicals/drugs |
| TLR4 | Opioid-class drugs | Chemicals/drugs |
| TLR5 | Flagellin | PAMP |
| TLR5 | Profilin (*Toxoplasma gondii*) | PAMP |
| TLR6 | Diacyl lipopeptides | PAMP |
| TLR7 | Imidazoquinoline | Chemicals/drugs |
| TLR7 | loxoribine (a guanosine analogue) | Chemicals/drugs |
| TLR7 | Bropirimine | Chemicals/drugs |
| TLR7 | Resiquimod (R-848) | Chemicals/drugs |
| TLR7 | ssRNA | PAMP |
| TLR8 | ssRNA | PAMP |
| TLR8 | dsRNA | PAMP |
| TLR9 | Unmethylated CpG DNA | PAMP |
| TLR10 | Triacylated lipopeptides | PAMP |
| TLR11 | Profilin (*Toxoplasma gondii*) | PAMP |
| TLR12 | Profilin (*Toxoplasma gondii*) | PAMP |
| TLR13 | bacterial ribosomal RNA sequence "CGGAAAGACC" | PAMP |

In some embodiments, a TLR ligand can comprise beta-defensin 2, fibronectin, HMGB1, HSP22, HSP70, HSP72, endoplasmin, alpha-crystallin A chain, human cardiac myosin, resistin, S100 proteins, surfactant proteins A, tenascin-C, biglycan, CD138, oligosaccharides of hyaluronan, hyaluronan breakdown fragments, mRNA, small interfering RNA (siRNA), oxidized PAPC (OxPAPC), monosodium urate crystals, etc. In some cases, a TLR agonist can comprise live, dead, or a fragment of bacteria, fungi, protist, protozoa, nematodes, plant cells or animal cells. In other embodiments, a TLR agonist can comprise a virus or an inactivated virus. In some instances, a TLR agonist can also comprise OX40, OX40 ligand, 4-1-BB, 4-1BB ligand, CD27, CD30, CD30 ligand, HVEM, TROY, RELT, TNF-alpha, TNF-beta, CD70, RANK ligand, LT-alpha, LT-beta, GITR ligand and LIGHT, MALP-2, IRM compounds, derivatives herein and thereof, combinations herein and thereof, and other TLR agonists known in the art.

In some cases, a TLR ligand can be a synthetic ligand. A synthetic ligand can comprise Pam3Cys, CFA, MALP-2, Pam2Cys, FSL-1, Hib-OMPC, poly I:C, polyadenosine-polyuridylic acid (poly A:U), AGP, Monophosphoryl lipid A (MPLA), RC-529, MDF2 beta, flagellin, guanosine analogs, imidazaquinolines, or loxoribine. Imidazoquinoles can comprise Imiquimod, Aldara, R-848, ssPolyU, 3M-012, CpG-oligonucleotides, or Resiquimod, polyinosinic-polycytidylic acid stabilized with poly-L-lysine and carboxymethylcellulose (Poly-ICLC), HLA-A2 restricted peptides, Sialyl-Tn (STn), keyhole limpet haemocyanin (KLH), derivatives herein and thereof, or combinations herein and thereof.

Lipoteichoic Acid (LTA)

A personalized tumor vaccine can comprise LTA. Lipoteichoic acid (LTA) is a surface-associated adhesion molecule. LTA is a major component of the cell wall of gram-positive bacteria. LTA can be secreted by the bacteria. LTA can be maintained as a lyophilized powder. Different gram-positive bacterial species can have different structures of LTA. LTA is anchored to the cell membrane by diacylglycerol. LTA can also comprise ribitol or plycerol phosphate. LTA can induce a proinflammatory cytokine response in the immune system. An exemplary chemical structure of LTA is shown in Formula III.

7x10^-1 g/dose, 8x10^-1 g/dose, 9x10^-1 g/dose, 1x10^-2 g/dose, 2x10^-2 g/dose, 3x10^-2 g/dose, 4x10^-2 g/dose, 5x10^-2 g/dose, 6x10^-2 g/dose, 7x10^-2 g/dose, 8x10^-2 g/dose, 9x10^-2 g/dose, 1x10^-3 g/dose, 2x10^-3 g/dose, 3x10^-3 g/dose, 4x10^-3 g/dose, 5x10^-3 g/dose, 6x10^-3 g/dose, 7x10^-3 g/dose, 8x10^-3 g/dose, 9x10^-3 g/dose, 1x10^-4 g/dose, 2x10^-4 g/dose, 3x10^-4 g/dose, 4x10^-4 g/dose, 5x10^-4 g/dose, 6x10^-4 g/dose, 7x10^-4 g/dose, 8x10^-4 g/dose, 9x10^-4 g/dose, 1x10^-5 g/dose, 2x10^-5 g/dose, 3x10^-5 g/dose, 4x10^-5 g/dose, 5x10^-5 g/dose, 6x10^-5 g/dose, 7x10^-5 g/dose, 8x10^-5 g/dose, 9x10^-5 g/dose, 1x10^-6 g/dose, 2x10^-6 g/dose, 3x10^-6 g/dose, 4x10^-6 g/dose, 5x10^-6 g/dose, 6x10^-6 g/dose, 7x10^-6 g/dose, 8x10^-6 g/dose, or 9x10^-6 g LTA. In some cases, a personalized tumor vaccine can comprise from 5x10^0 g/dose to 1x10^1 g/dose, from 1x10^0 g/dose to 5x10^0 g/dose, from 5x10^-1 g/dose to 1x10^0 g/dose, from 1x10^-1 g/dose to 5x10^-1 g/dose, from 5x10^-2 g/dose to 1x10^-1 g/dose, from 1x10^-2 g/dose to 5x10^-2 g/dose, from 5x10^-3 g/dose to 1x10^-2 g/dose, from 1x10^-3 g/dose to 5x10^-3 g/dose, from 5x10^-4 g/dose to 1x10^-3 g/dose, from 1x10^-4 g/dose to 5x10^-4 g/dose, from 5x10^-5 g/dose to 1x10^-4 g/dose, from 1x10^-5 g/dose to 5x10^-5 g/dose, from 5x10^-6 g/dose to 1x10^-5 g/dose, from 1x10^-6 g/dose to 5x10^-6 g/dose, from 5x10^-7 g/dose to 1x10^-7 g/dose LTA. A personalized tumor vaccine can also comprise about 0.05 to 5 mg/dose LTA. A personalized tumor vaccine can also comprise about 0.05 mg/dose LTA. A personalized tumor vaccine can also comprise about 5 mg/dose LTA. A personalized tumor vaccine can also comprise about 0.024 mg/dose LTA. A personalized tumor vaccine can also comprise about 0.584 mg/dose LTA.

Formula III

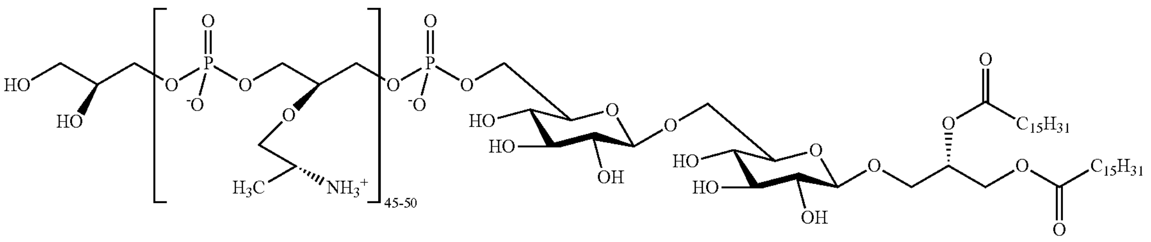

LTA is a TLR agonist: LTA can bind to TLR-2 to induce NF-κB TNF alpha expression. LTA can induce the complement system to induce passive immune kill phenomenon. LTA can also induce release of the reactive oxygen and nitrogen species from neutrophils and macrophage, acid hydrolases, cationic proteinases, or cytotoxic cytokines. LTA can also activate scavenger receptors. In some embodiments, LTA can link to tumor or cancer cells and the fragments of tumor or cancer cell membranes can support scavenger receptors-mediated recognition of cancer antigen by dendritic cells. In some cases, LTA can be a PAMP. In other case, LTA can be an immunostimulatory adjuvant.

LTA can comprise LTA from any gram-positive bacteria. LTA can comprise LTA from *Bacillus subtilis, Enterococcus hirae, Staphylococcus aureus*, or *Streptococcus pyogenes*. A personalized tumor vaccine can comprise 1x10^0 g/dose, 2x10^0 g/dose, 3x10^0 g/dose, 4x10^0 g/dose, 5x10^0 g/dose, 6x10^0 g/dose, 7x10^0 g/dose, 8x10^0 g/dose, 9x10^0 g/dose, 1x10^-1 g/dose, 2x10^-1 g/dose, 3x10^-1 g/dose, 4x10^-1 g/dose, 5x10^-1 g/dose, 6x10^-1 g/dose, Polyinosinic:Polycytidylic Acid (Poly(I:C))

A personalized tumor vaccine can comprise Poly(I:C). Poly(I:C) can activate TLR3, expressed at the cell membrane of B-cells, macrophages, and dendritic cells. Because of its structural similarity to dsRNA found in virus, poly(I:C) is a TLR agonist. Poly(I:C) and its derivatives can be used as an agonist or activator of TLR3. Such activation can further activate the transcription factor interferon regulatory factor 3 (IRF3) and produce type I IFN-beta. Poly(I:C) can also generate stable mature dendritic cells. In some cases, poly(I:C) can be a PAMP. In other case, poly(I:C) can be an immunostimulatory adjuvant.

Derivatives of poly(I:C) can comprise poly-L-lysine and carboxymethylcellulose (Poly ICLC) or Poly I:$C_{12}$U. Derivatives of poly(I:C) can also comprise any chemical known by an ordinary person in the cancer or immunity biology or therapy art.

An exemplary chemical structure of poly(I:C) is shown in Formula IV.

Formula IV

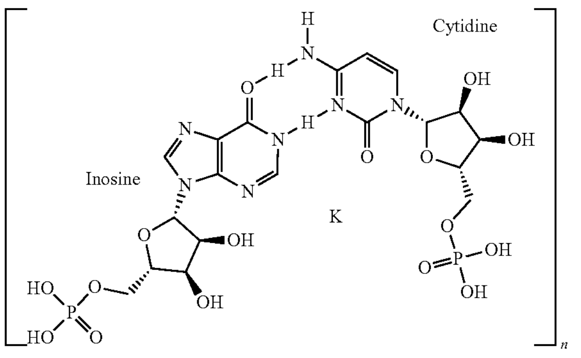

Schematic Structure of Poly(I:C)

Poly(I:C) can comprise a mismatched double-stranded nucleic acid. A nucleic acid strand in poly(I:C) can comprise RNA. Poly(I:C) can comprise a polymer of inosinic acid and cytidylic acid.

Poly(I:C) can be maintained or administered to a subject as a sodium salt or potassium salt. Poly(I:C) can also be maintained as a lyophilized powder.

A personalized tumor vaccine can comprise 1×10^0 g/dose, 2×10^0 g/dose, 3×10^0 g/dose, 4×10^0 g/dose, 5×10^0 g/dose, 6×10^0 g/dose, 7×10^0 g/dose, 8×10^0 g/dose, 9×10^0 g/dose, 1×10^−1 g/dose, 2×10^−1 g/dose, 3×10^−1 g/dose, 4×10^−1 g/dose, 5×10^−1 g/dose, 6×10^−1 g/dose, 7×10^−1 g/dose, 8×10^−1 g/dose, 9×10^−1 g/dose, 1×10^−2 g/dose, 2×10^−2 g/dose, 3×10^−2 g/dose, 4×10^−2 g/dose, 5×10^−2 g/dose, 6×10^−2 g/dose, 7×10^−2 g/dose, 8×10^−2 g/dose, 9×10^−2 g/dose, 1×10^−3 g/dose, 2×10^−3 g/dose, 3×10^−3 g/dose, 4×10^−3 g/dose, 5×10^−3 g/dose, 6×10^−3 g/dose, 7×10^−3 g/dose, 8×10^−3 g/dose, 9×10^−3 g/dose, 1×10^−4 g/dose, 2×10^−4 g/dose, 3×10^−4 g/dose, 4×10^−4 g/dose, 5×10^−4 g/dose, 6×10^−4 g/dose, 7×10^−4 g/dose, 8×10^−4 g/dose, 9×10^−4 g/dose, 1×10^−5 g/dose, 2×10^−5 g/dose, 3×10^−5 g/dose, 4×10^−5 g/dose, 5×10^−5 g/dose, 6×10^−5 g/dose, 7×10^−5 g/dose, 8×10^−5 g/dose, 9×10^−5 g/dose, 1×10^−6 g/dose, 2×10^−6 g/dose, 3×10^−6 g/dose, 4×10^−6 g/dose, 5×10^−6 g/dose, 6×10^−6 g/dose, 7×10^−6 g/dose, 8×10^−6 g/dose, or 9×10^−6 g/dose poly (I:C). In some cases, a personalized tumor vaccine can comprise from 5×10^0 g to 1×10^1 g/dose, from 1×10^0 g/dose to 5×10^0 g/dose, from 5×10^−1 g/dose to 1×10^0 g/dose, from 1×10^−1 g/dose to 5×10^−1 g/dose, from 5×10^−2 g/dose to 1×10^−1 g/dose, from 1×10^−2 g/dose to 5×10^−2 g/dose, from 5×10^−3 g/dose to 1×10^−2 g/dose, from 1×10^−3 g/dose to 5×10^−3 g/dose, from 5×10^−4 g/dose to 1×10^−3 g/dose, from 1×10^−4 g/dose to 5×10^−4 g/dose, from 5×10^−5 g/dose to 1×10^−4 g/dose, from 1×10^−5 g/dose to 5×10^−5 g/dose, from 5×10^−6 g/dose to 1×10^−5 g/dose, from 1×10^−6 g/dose to 5×10^−6 g/dose, from 5×10^−7 g/dose to 1×10^−7 g poly(I:C). A personalized tumor vaccine can also comprise about 0.05 to 5 mg/dose poly(I:C). A personalized tumor vaccine can also comprise about 0.05 mg/dose poly(I:C). A personalized tumor vaccine can also comprise about 5 mg/dose poly(I:C). A personalized tumor vaccine can also comprise about 0.024 mg/dose poly(I:C). A personalized tumor vaccine can also comprise about 0.584 mg/dose poly(I:C).

Resiquimod (R-848)

A personalized tumor vaccine can comprise a Resiquimod (R-848). R-848 is an imidazoquinolinamine TLR agonist. R-848 may have antitumor or antiviral activity. In some cases, R-848 can be a PAMP. In other case, R-848 can be used as an immunostimulatory adjuvant. R-848 can activate TLR7/8. Activation of TLR7/8 by R-848 can lead to the production of cytokines, especially interferon-alpha (INF-α), and enhanced T-helper 1 (Th1) immune responses. R-848 can also stimulate the maturation of dendritic cells. R-848 can also activate macrophages and B-cells.

R-848 is an analogue of imiquimod. Aa exemplary structure of R-848 is listed in Formula V.

Formula V

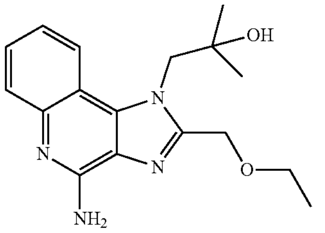

R-848 can also comprise $C_{17}H_{22}N_4O_2$. R-848 can have a molecular weight of 314.4 g/mol. It can comprise 2 hydrogen bond donors and 5 hydrogen bond acceptors. R-848 can also comprise 5 rotatable bonds. R-848 can comprise a monoisotopic mass of 314.174276 g/mol.

A personalized tumor vaccine can comprise 1×10^0 g/dose, 2×10^0 g/dose, 3×10^0 g/dose, 4×10^0 g/dose, 5×10^0 g/dose, 6×10^0 g/dose, 7×10^0 g/dose, 8×10^0 g/dose, 9×10^0 g/dose, 1×10^−1 g/dose, 2×10^−1 g/dose, 3×10^−1 g/dose, 4×10^−1 g/dose, 5×10^−1 g/dose, 6×10^−1 g/dose, 7×10^−1 g/dose, 8×10^−1 g/dose, 9×10^−1 g/dose, 1×10^−2 g/dose, 2×10^−2 g/dose, 3×10^−2 g/dose, 4×10^−2 g/dose, 5×10^−2 g/dose, 6×10^−2 g/dose, 7×10^−2 g/dose, 8×10^−2 g/dose, 9×10^−2 g/dose, 1×10^−3 g/dose, 2×10^−3 g/dose, 3×10^−3 g/dose, 4×10^−3 g/dose, 5×10^−3 g/dose, 6×10^−3 g/dose, 7×10^−3 g/dose, 8×10^−3 g/dose, 9×10^−3 g/dose, 1×10^−4 g/dose, 2×10^−4 g/dose, 3×10^−4 g/dose, 4×10^−4 g/dose, 5×10^−4 g/dose, 6×10^−4 g/dose, 7×10^−4 g/dose, 8×10^−4 g/dose, 9×10^−4 g/dose, 1×10^−5 g/dose, 2×10^−5 g/dose, 3×10^−5 g/dose, 4×10^−5 g/dose, 5×10^−5 g/dose, 6×10^−5 g/dose, 7×10^−5 g/dose, 8×10^−5 g/dose, 9×10^−5 g/dose, 1×10^−6 g/dose, 2×10^−6 g/dose, 3×10^−6 g/dose, 4×10^−6 g/dose, 5×10^−6 g/dose, 6×10^−6 g/dose, 7×10^−6 g/dose, 8×10^−6 g/dose, or 9×10^−6 g/dose R-848. In some cases, a personalized tumor vaccine can comprise from 5×10^0 g to 1×10^1 g/dose, from 1×10^0 g/dose to 5×10^0 g/dose, from 5×10^−1 g/dose to 1×10^0 g/dose, from 1×10^−1 g/dose to 5×10^−1 g/dose, from 5×10^−2 g/dose to 1×10^−1 g/dose, from 1×10^−2 g/dose to 5×10^−2 g/dose, from 5×10^−3 g/dose to 1×10^−2 g/dose, from 1×10^−3 g/dose to 5×10^−3 g/dose, from 5×10^−4 g/dose to 1×10^−3 g/dose, from 1×10^−4 g/dose to 5×10^−4 g/dose, from 5×10^−5 g/dose to 1×10^−4 g/dose, from 1×10^−5 g/dose to 5×10^−5 g/dose, from 5×10^−6 g/dose to 1×10^−5 g/dose, from 1×10^−6 g/dose to 5×10^−6 g/dose, from 5×10^−7 g/dose to 1×10^−7 g/dose R-848. A personalized tumor vaccine can also comprise about 0.05 to 5 mg/dose R-848. A personalized tumor vaccine can also comprise about 0.05 mg/dose R-848. A personalized tumor vaccine can also comprise about 5 mg/dose R-848. A personalized tumor vaccine can also comprise about 0.024 mg/dose R-848. A personalized tumor vaccine can also comprise about 0.584 mg/dose R-848.

Anti-CD40 monoclonal antibody (mAb) CD40 is a surface protein receptor, belonging to the tumor necrosis factor (TNF) receptor family. Activation of CD40 can induce dendritic cell licensing, T-cell activation, cytokine production, macrophage infiltration of the tumors, and other anti-tumor responses. CD40 agonists can be used activate CD40 and to induce antitumor immune response.

A CD40 agonist can comprise an anti-CD40 monoclonal antibody (mAb). In some instances, a personalized tumor vaccine can comprise 1×10^0 g/dose, 2×10^0 g/dose, 3×10^0 g/dose, 4×10^0 g/dose, 5×10^0 g/dose, 6×10^0 g/dose, 7×10^0 g/dose, 8×10^0 g/dose, 9×10^0 g/dose, 1×10^−1 g/dose, 2×10^−1 g/dose, 3×10^−1 g/dose, 4×10^−1 g/dose, 5×10^−1 g/dose, 6×10^−1 g/dose, 7×10^−1 g/dose, 8×10^−1 g/dose, 9×10^−1 g/dose, 1×10^−2 g/dose, 2×10^−2 g/dose, 3×10^−2 g/dose, 4×10^−2 g/dose, 5×10^−2 g/dose, 6×10^−2 g/dose, 7×10^−2 g/dose, 8×10^−2 g/dose, 9×10^−2 g/dose, 1×10^−3 g/dose, 2×10^−3 g/dose, 3×10^−3 g/dose, 4×10^−3 g/dose, 5×10^−3 g/dose, 6×10^−3 g/dose, 7×10^−3 g/dose, 8×10^−3 g/dose, 9×10^−3 g/dose, 1×10^−4 g/dose, 2×10^−4 g/dose, 3×10^−4 g/dose, 4×10^−4 g/dose, 5×10^−4 g/dose, 6×10^−4 g/dose, 7×10^−4 g/dose, 8×10^−4 g/dose, 9×10^−4 g/dose, 1×10^−5 g/dose, 2×10^−5 g/dose, 3×10^−5 g/dose, 4×10^−5 g/dose, 5×10^−5 g/dose, 6×10^−5 g/dose, 7×10^−5 g/dose, 8×10^−5 g/dose, 9×10^−5 g/dose, 1×10^−6 g/dose, 2×10^−6 g/dose, 3×10^−6 g/dose, 4×10^−6 g/dose, 5×10^−6 g/dose, 6×10^−6 g/dose, 7×10^−6 g/dose, 8×10^−6 g/dose, or 9×10^−6 g anti-CD40 mAb. In some cases, a personalized tumor vaccine can comprise from 5×10^0 g/dose to 1×10^1 g/dose, from 1×10^0 g/dose to 5×10^0 g/dose, from 5×10^−1 g/dose to 1×10^0 g/dose, from 1×10^−1 g/dose to 5×10^−1 g/dose, from 5×10^−2 g/dose to 1×10^−1 g/dose, from 1×10^−2 g/dose to 5×10^−2 g/dose, from 5×10^−3 g/dose to 1×10^−2 g/dose, from 1×10^−3 g/dose to 5×10^−3 g/dose, from 5×10^−4 g/dose to 1×10^−3 g/dose, from 1×10^−4 g/dose to 5×10^−4 g/dose, from 5×10^−5 g/dose to 1×10^−4 g/dose, from 1×10^−5 g/dose to 5×10^−5 g/dose, from 5×10^−6 g/dose to 1×10^−5 g/dose, from 1×10^−6 g/dose to 5×10^−6 g/dose, from 5×10^−7 g/dose to 1×10^−7 g/dose anti-CD40 mAb. A personalized tumor vaccine can also comprise about 0.04 mg/dose to about 4 mg/dose anti-CD40 mAb. A personalized tumor vaccine can also comprise about 0.04 mg/dose anti-CD40 mAb. A personalized tumor vaccine can also comprise about 4 mg/dose anti-CD40 mAb. A personalized tumor vaccine can also comprise about 0.02 mg/dose anti-CD40 mAb. A personalized tumor vaccine can also comprise about 0.467 mg/dose anti-CD40 mAb.

In some instances, a personalized tumor vaccine can also replace, substitute or combine an anti-CD40 mAb with a CD40 agonist described herein and thereof. In some cases, a CD40 agonist can also comprise trimer CD40 ligand (CD40L), ectopic expression of CD40L, any derivatives herein and thereof, or any combinations herein and thereof. In some instances, an anti-CD40 antibody can comprise ABBV-927, ADC-1013, Selicrelumab, APX005M, Chi-Lob7/4, ADC-1013, SEA-CD40, CDX1140, CP-870893, dacetuzmab, any derivatives herein and thereof, or any combinations herein and thereof. A CD40 agonist can also comprise CD40L, GM.CD40L, MEDI5083 (NCT03089645), HERACD40L, duokine, and derivatives herein and thereof, or any combinations herein and thereof.

An antibody can comprise IgA, IgD, IgE, IgG, IgM, any derivatives herein and thereof, or any combinations herein and thereof. In some embodiments, an anti-CD40 antibody can comprise a murine, human, chimeric, or humanized antibody. In other cases, an anti-CD40 antibody can comprise a polyclonal or monoclonal antibody. In some instances, an antibody can comprise an antibody from chickens, goats, guinea pigs, hamsters, horses, mice, rats, sheep, monkeys, chimpanzees, humans, camels, sharks, rabbits, alpaca, llama, or any combinations thereof. In some cases, an anti-CD40 antibody can comprise an intact antibody or an antibody fragment. In some cases, an anti-CD40 antibody can comprise IgA1, IgA2, IgG1, IgG2, IgG3, IgG4, any derivatives herein and thereof, or any combinations herein and thereof. In some embodiments, an anti-CD40 antibody can comprise a bispecific antibody, monoclonal antibody, single-chain variable fragment (scFv), single-chain antigen-binding fragment (scFab), Dual-variable domains Ig (DVD-Ig), scFv-IgG fusion, scFv-Fc (constant region), heavy chain antibody (HcAb), new antigen receptor antibody (IgNAR), domain antibody (dAb), single-dAb (sdAb), diabody, intrabody, trioMab, F(ab)2 bispecific antibody, F(ab)3 trispecific antibody, BiTE antibody, DART antibody, tand antibody, minibody, Bis-scFv, triabody, tetrabody, camel Ig, shark Ig, fragments herein and thereof, derivatives herein and thereof, or any combinations herein and thereof.

In some embodiments, activation of CD40 and TLRs can independently activate distinct immune response pathways. In some cases, activation of CD40 and TLRs can activate overlapping immune response pathways. In some embodiments, activation of CD40 and TLRs have an additive effect on the activation of immune response pathway. In other cases, activation of CD40 and TLRs have a synergistic effect on the activation immune response pathways. In some embodiments, activation of CD40 and TLRs can have an additive or synergistic effect on an antitumor response. In some instances, an antitumor response can comprise inhibiting, reversing, stropping, reducing, restraining, suppressing, or prohibiting the growth, metastasis of tumors, differentiation, migration, division, or secretion of tumor or tumor cells.

Organic and Inorganic Adjuvants

In some instances, an immunostimulatory adjuvant can comprise an organic molecule immunostimulatory adjuvant. In some cases, an immunostimulatory adjuvant can comprise an inorganic molecule immunostimulatory adjuvant.

An organic immunostimulatory adjuvant can comprise inactivated *Mycobacterium tuberculosis*, squalene, saponins, Monophosphoryl lipid A (MPL), any derivatives herein and thereof, or any combination herein and thereof. In some instances, an organic immunostimulatory adjuvant can also comprise algammulin; algal glucan; β-glucan; cholera toxin B subunit; CRL1005: ABA block polymer with mean value of x=8 and γ=205; γ insulin: linear (unbranched) B-D (2→1) polyfructofuranoxyl-α-D-glucose; Gerbu adjuvant: N-acetylglucosamine-(β1-4)-N-acetylmuramyl-L-alanyl-D-glutamine (GMDP); dimethyldioctadecyl ammonium chloride (DDA); zinc L-proline salt complex (Zn-Pro-8); Imiquimod (1-(2-methylpropyl)-1H-imidazo[4,5-c]quinoline-4-Amine; ImmTher™: N-acetylglucoaminyl-N-acetylmuramyl-L-Ala-D-iso Glu-L-Ala-dipalmitate glycerol; Murametide: methyl(2R)-2-[[(2S)-2-[2-[(2S,3R,4R,5S,6R)-3-acetamido-2,5-dihydroxy-6-(hydroxymethyl) oxan-4-yl]oxypropanoylamino]propanoyl]amino]-5-amino-5-oxopentanoate; QS-21; S-28463:4-amino-a, a-dimethyl-1H-imidazo[4,5-c]quinoline-1-ethanol; Salvopeptide: VQGEESNDK·HCl (IL-1β 163-171 peptide); Threonyl-MDP (Termurtide™): N-acetylmuramyl-L-threonyl-D-iso-glutamine; interleukin (IL)-18; IL-1 beta; IL-2; IL-12; IL-15; IL-4; IL 10; γ interferon; NFκB regulatory signal protein; DNA oligonucleotides such as C- or G-containing oligonucleotides, any derivatives herein and thereof, or any combination herein and thereof. In some instances, an organic immunostimulatory adjuvant can also comprise nucleic acid sequences encoding immune regulatory lymphokines such as IL-18, IL-1 beta, IL-2, IL-12, IL-15, IL-4, IL10, γ interferon, NFκB regulatory signal protein, any derivatives herein and thereof, or any combination herein and thereof. In some cases, an organic immunostimulatory adjuvant can comprise Trehalose-6,6'-dimycolate (TDM), muramyl dipeptide (MDP); AF or SPT (emulsion of squalane (5%); Tween 80 (0.2%); AVRIDINE™ (propane-diamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); cholera holotoxin; cholera-toxin-A1-protein-A-D-fragment fusion protein; sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); ISCOMS™; ISCOPREP 7.0.3.™; liposomes; LOXORIBINE™ (7-allyl-8-oxoguanosine); LT oral adjuvant (*E. coli* labile enterotoxin-protoxin); MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glyceroldipalmitoyl); NAGO (neuraminidase-galactose oxidase); NISVs (non-ionic surfactant vesicles); PLEURAN™ (beta-glucan); PLGA, PGA, or PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5 c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide); lipopeptides, comprising Pam3Cys; copolymers, comprising Optivax (CRL1005), L121, Poloaxmer4010); liposomes, comprising Stealth, cochleates, comprising BIORAL; plant derived adjuvants, comprising QS21, Quil A, Iscomatrix; Tomatine; PLG; PMM; Inulin; microbe derived adjuvants, comprising Romurtide, DETOX™, MPL, CWS, Mannose, CpG nucleic acid sequences, CpG7909, ligands of human TLR 1-10, ligands of murine TLR 1-13, ISS-1018, IC31, Imidazoquinolines, Rintatolimod, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; or CGRP neuropeptide. An organic immunostimulatory adjuvant can also comprise cationic or polycationic compounds. In some cases, cationic or polycationic compounds can comprise cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB (1), pVEC, hCT-derived peptides, SAP, protamine, spermine, spermidine, or histones. In other cases, cationic or polycationic compounds can comprise cationic polysaccharides. In some instances, cationic polysaccharides can comprise chitosan; polybrene; cationic polymers comprising polyethyleneimine (PEI); cationic lipids comprising DOTMA: 1,2-di-O-octadecenyl-3-trimethylammonium propane (chloride salt); DMRIE; di-C14-amidine; DOTIM; SAINT; DC-Chol; BGTC; CTAP: DOPC; DODAP; DOPE: Dioleyl phosphatidylethanol-amine; DOSPA; DODAB; DOIC; DMEPC; DOGS: Dioctadecylamidoglicylspermin; DIMRI: Dimyristo-oxypropyl dimethyl hydroxyethyl ammonium bromide; DOTAP: dioleoyloxy-3-(trimethylammonio) propane; DC-6-14: O,O-ditetradecanoyl-N-(−trimethylammonioacetyl) diethanolamine chloride; CLIP1: rac-[(2,3-Dioctadecyloxypropyl) (2-hydroxyethyl)]-dimethylammonium chloride; CLIP6: rac-[2 (2,3-Dihexadecyloxypropyl-oxymethyloxy) ethyl]trimethylammonium bromide; CLIPS: rac-[2 (2,3-dihexadecyloxypropyl-oxysuccinyloxy)ethyl]-trimethylammonium; oligofectamine; or cationic or polycationic polymers comprising modified polyaminoacids, comprising aminoacid-polymers or reversed polyamides; modified polyethylenes comprising PVP (poly(N-ethyl-4-vinylpyridinium bromide)); modified acrylates comprising pDMAEMA (poly (dimethylaminoethyl methylacrylate)); modified Amidoamines comprising pAMAM (poly(amidoamine)); modified polybetaaminoester (PBAE) comprising diamine end modified 1,4 butanediol diacrylate-co-5-amino-1-pentanol polymers; dendrimers comprising polypropylamine dendrimers or pAMAM based dendrimers; polyimine(s), comprising PEI: poly(ethyleneimine), poly(propyleneimine), polyallylamine; sugar backbone based polymers, comprising cyclodextrin based polymers, dextran based polymers, Chitosan; silan backbone based polymers comprising PMOXA-PDMS copolymers; Blockpolymers comprising a combination of one or more cationic blocks (e.g. selected of a cationic polymer as mentioned above) and of one or more hydrophilic- or hydrophobic blocks (e.g polyethyleneglycole). In some instances, an organic immunostimulatory adjuvant can comprise emulsion adjuvant. In some instances, an emulsion adjuvant can comprise squalene;

DL-a-tocopherol (vitamin E); lipids from the *Salmonella minnesota* bactrerium or Quillaja *saponaria* tree; AS01B; ASOIE; AS03; AS04; CFA; SAF; IFA; MF59; Provax; TiterMax; Montanide; or Vaxfectin. In some cases, an organic immunostimulatory adjuvant can comprise derivatives or combinations of any organic stimulatory adjuvants herein and thereof; microspheres and microparticles of any organic adjuvants described herein and thereof, or nanospheres or nanoparticles of any organic adjuvants described herein and thereof.

In some cases, an immunostimulatory adjuvant can comprise an inorganic molecule immunostimulatory adjuvant. An inorganic immunostimulatory adjuvant can comprise salts of metals such as cerium, zinc, iron, aluminum and calcium. In some instances, an inorganic immunostimulatory adjuvant can comprise an aluminum-containing compound (alum). Alum can comprise materials with a formula $KAl(SO_4)_2 \cdot 12H_2O$, $(NH_4^+)(Al(SO_4)_2) \cdot 12H_2O$ any derivatives herein and thereof, or any combinations herein and thereof. Alum can also comprise aluminum oxyhydroxide (AIO (OH)) or aluminum hydroxyphosphate $(Al(OH)_x(PO_4)_y)$. In some cases, an aluminum-containing compound can also comprise Imject™ alum. Imject™ alum can comprise crystalline magnesium hydroxide and aluminum hydroxide. Alum can also comprise Alhydrogel®, Adju-Phos®, ADJUMER™ (polyphosphazene), aluminium phosphate gel, calcium phosphate gel, CAP™ (calcium phosphate nanoparticles), cesium alum, phosphate-buffered saline, Rehydragel™ any derivatives herein and thereof, or any combinations herein and thereof.

Attenuated Cancer Cells

In some cases, a personalized tumor vaccine can comprise a population or groups of attenuated cancer cells. An attenuated cancer cell can comprise a cancer cell or population or group of cancer cells undergoing or undergone treatments. In some instances, an attenuated cancer cell can be a mammalian cell. In some instances, an attenuated cancer cell can be a non-mammalian cell. In some instances, an attenuated cancer cell can comprise a mouse cell. In some instances, an attenuated cancer cell can be a human cell. In some instances, an attenuated cancer cell can be a living cell. In some embodiments, an attenuated cancer cell can comprise an aged, stressed, injured, infected, or transformed cells not found in normal or healthy cells. In some instances, an attenuated cancer cell can comprise a tumor or cancer cell. In some instances, an attenuated cancer cell can comprise an overgrown cell. In some instances, an attenuated cancer cell can comprise an over-divided cell. In some cases, an attenuated cancer cell can comprise an over-differentiated cell. In some instances, an attenuated cancer cell can comprise a stem cell. In some instances, an attenuated cancer cell can comprise a cancer stem cell. In some instances, an attenuated cancer cell can comprise a non-dividing cell. In some instances, an attenuated cancer cell can comprise a mitotic cell. In some instances, an attenuated cancer cell can comprise a meiotic cell. In some cases, an attenuated cancer cell can comprise a growth-arrested cell. In some cases, an attenuated cancer cell can comprise a replication-arrested cell. In some cases, an attenuated cancer cell can comprise a division-arrested cell. In some cases, an attenuated cancer cell can comprise a mitosis-arrested cell.

In some cases, an attenuated cancer cell can comprise a differentiation-arrested cell. In some cases, an attenuated cancer cell can comprise a meiosis-arrested cell. In some embodiments, an attenuated cancer cell can comprise a monkey, chimpanzee, rat, rabbit, pig, guinea pig, horse, camel, alpaca, llama, dog, cat, cow cell.

In some cases, an attenuated cancer cell can comprise a primary tumor or cancer cell. In some cases, an attenuated cancer cell can comprise a cultured cancer cell. In some instances, an attenuated cancer cell can comprise a tumor or cancer cell extracted from an individual and cultured in vitro after the extraction. In some instances, an extraction can comprise harvesting a tumor or cancer cell from a biopsy of tissues from an individual. In some instances, an extraction can comprise harvesting a tumor or cancer cell from a biopsy of a site of tumor or cancer from the individual. In some cases, an extraction can comprise harvesting a tumor or cancer cell from a biopsy of circulating tumor or cancer cells from an individual. In some instances, a biopsy can comprise a bone biopsy, a bone marrow biopsy, a breast biopsy, a gastrointestinal biopsy, a lung biopsy, a liver biopsy, a prostate biopsy, a nervous system biopsy, a urogenital biopsy, a lymph node biopsy, a muscle biopsy, a skin biopsy, a blood biopsy, a body fluid biopsy, a cardiac biopsy, an endometrial biopsy, an open biopsy, a sentinel lymph node biopsy, any derivatives herein and thereof, or any combinations herein and thereof. In some instances, a biopsy can comprise a fine needle aspiration biopsy, a core needle biopsy, a vacuum-assisted biopsy, an excisional biopsy, a shave biopsy, a punch biopsy, an endoscopic biopsy, a laparoscopic biopsy, a bone marrow aspiration biopsy, a liquid biopsy, any derivatives herein and thereof, or any combinations herein and thereof. In other cases, a biopsy can comprise an incisional biopsy or an excisional biopsy.

In some instances, an attenuated cancer cell can comprise a tumor or cancer cell extracted from an individual without any culturing in vitro after the extraction. In some cases, a personalized tumor vaccine can comprise any types of cells described herein and thereof.

A personalized tumor vaccine can comprise from 1×10^0 to 1×10^1 attenuated cancer cells, from 5×10^0 to 5×10^1 attenuated cancer cells, from 1×10^1 to 1×10^2 attenuated cancer cells, from 5×10^1 to 5×10^2 attenuated cancer cells, from 1×10^2 to 1×10^3 attenuated cancer cells, from 5×10^2 to 5×10^3 attenuated cancer cells, from 1×10^3 to 1×10^4 attenuated cancer cells, from 5×10^3 to 5×10^4 attenuated cancer cells, from 1×10^4 to 1×10^5 attenuated cancer cells, from 5×10^4 to 5×10^5 attenuated cancer cells, from 1×10^5 to 1×10^6 attenuated cancer cells, from 5×10^5 to 5×10^6 attenuated cancer cells, from 1×10^6 to 1×10^7 attenuated cancer cells, from 5×10^6 to 5×10^7 attenuated cancer cells, from 1×10^7 to 1×10^8 attenuated cancer cells, from 5×10^7 to 5×10^8 attenuated cancer cells, from 1×10^8 to 1×10^9 attenuated cancer cells, from 5×10^8 to 5×10^9 attenuated cancer cells, from 1×10^9 to 1×10^10 attenuated cancer cells, from 5×10^9 to 5×10^10 attenuated cancer cells, from 1×10^10 to 1×10^11 attenuated cancer cells, from 5×10^10 to 5×10^11 attenuated cancer cells, from 1×10^11 to 1×10^12 attenuated cancer cells, from 5×10^11 to 5×10^12 attenuated cancer cells, from 1×10^12 to 1×10^13 attenuated cancer cells, from 5×10^12 to 5×10^13 attenuated cancer cells, from 1×10^13 to 1×10^14 attenuated cancer cells, from 5×10^13 to 5×10^14 attenuated cancer cells, from 1×10^14 to 1×10^15 attenuated cancer cells, from 5×10^14 to 5×10^15 attenuated cancer cells, from 1×10^15 to 1×10^16 attenuated cancer cells, from 5×10^15 to 5×10^16 attenuated cancer cells, from 1×10^16 to 1×10^17 attenuated cancer cells, from 5×10^16 to 5×10^17 attenuated cancer cells, from 1×10^17 to 1×10^18 attenuated cancer cells, from 5×10^17 to 5×10^18 attenuated cancer cells, from 1×10^18 to 1×10^19 attenuated cancer cells, from 5×10^18 to 5×10^19 attenuated cancer cells, from 1×10^19 to 1×10^20 attenuated cancer cells, or from 5×10^19 to 5×10^20 attenuated cancer cells. In some embodiments, a personalized tumor vaccine can comprise 1×10^5, 2×10^5, 3×10^5, 4×10^5, 5×10^5, 6×10^5, 7×10^5, 8×10^5, 9×10^5, 1×10^6, 2×10^6, 3×10^6, 4×10^6, 5×10^6, 6×10^6, 7×10^6, 8×10^6, 9×10^6, or 1×10^7 attenuated cancer cells. A personalized tumor vaccine can comprise 1×10^6 attenuated cancer cells.

A therapeutically relevant amount of attenuated cancer cells can comprise from 1×10^0 to 1×10^1 attenuated cancer cells, from 5×10^0 to 5×10^1 attenuated cancer cells, from 1×10^1 to 1×10^2 attenuated cancer cells, from 5×10^1 to 5×10^2 attenuated cancer cells, from 1×10^2 to 1×10^3 attenuated cancer cells, from 5×10^2 to 5×10^3 attenuated cancer cells, from 1×10^3 to 1×10^4 attenuated cancer cells, from 5×10^3 to 5×10^4 attenuated cancer cells, from 1×10^4 to 1×10^5 attenuated cancer cells, from 5×10^4 to 5×10^5 attenuated cancer cells, from 1×10^5 to 1×10^6 attenuated cancer cells, from 5×10^5 to 5×10^6 attenuated cancer cells, from 1×10^6 to 1×10^7 attenuated cancer cells, from 5×10^6 to 5×10^7 attenuated cancer cells, from 1×10^7 to 1×10^8 attenuated cancer cells, from 5×10^7 to 5×10^8 attenuated cancer cells, from 1×10^8 to 1×10^9 attenuated cancer cells, from 5×10^8 to 5×10^9 attenuated cancer cells, from 1×10^9 to 1×10^10 attenuated cancer cells, from 5×10^9 to 5×10^10 attenuated cancer cells, from 1×10^10 to 1×10^11 attenuated cancer cells, from 5×10^10 to 5×10^11 attenuated cancer cells, from 1×10^11 to 1×10^12 attenuated cancer cells, from 5×10^11 to 5×10^12 attenuated cancer cells, from 1×10^12 to 1×10^13 attenuated cancer cells, from 5×10^12 to 5×10^13 attenuated cancer cells, from 1×10^13 to 1×10^14 attenuated cancer cells, from 5×10^13 to 5×10^14 attenuated cancer cells, from 1×10^14 to 1×10^15 attenuated cancer cells, from 5×10^14 to 5×10^15 attenuated cancer cells, from 1×10^15 to 1×10^16 attenuated cancer cells, from 5×10^15 to 5×10^16 attenuated cancer cells, from 1×10^16 to 1×10^17 attenuated cancer cells, from 5×10^16 to 5×10^17 attenuated cancer cells, from 1×10^17 to 1×10^18 attenuated cancer cells, from 5×10^17 to 5×10^18 attenuated cancer cells, from 1×10^18 to 1×10^19 attenuated cancer cells, from 5×10^18 to 5×10^19 attenuated cancer cells, from 1×10^19 to 1×10^20 attenuated cancer cells, or from 5×10^19 to 5×10^20 attenuated cancer cells. In some embodiments, a therapeutically relevant amount of attenuated cancer cells can comprise 1×10^5, 2×10^5, 3×10^5, 4×10^5, 5×10^5, 6×10^5, 7×10^5, 8×10^5, 9×10^5, 1×10^6, 2×10^6, 3×10^6, 4×10^6, 5×10^6, 6×10^6, 7×10^6, 8×10^6, 9×10^6, or 1×10^7 attenuated cancer cells. A therapeutically relevant amount of attenuated cancer cells can comprise 1×10^6 attenuated cancer cells In some cases, a treatment of obtaining an attenuated cancer cell can comprise a physical or a chemical treatment of a cancer cell. A treatment can stress, arrest, growth-inhibit, or injure a cancer cell. A treatment can change the chemical or physical composition of a cancer cell. A treatment can increase or decrease a component, molecule, chemical, or any derivatives herein and thereof of a cancer cell. In some instances, a treatment can damage the DNA of a cancer cell. A treatment can stress, arrest, growth-inhibit, or injure 0%, 1%, 5%, 10%, 15%, 20%, 25%, 30%, 35%, 40%, 45%, 50%, 55%, 60%, 65%, 70%, 75%, 80%, 85%, 90%, 95%, or 100% of a population or group of cells. A treatment can stress, arrest, growth-inhibit, or injure from 1 to 5%, from 2 to 6%, from 3 to 7%, from 4 to 8%, from 5 to 9%, from 6 to 10%, from 7 to 11%, from 8 to 12%, from 9 to 13%, from 10 to 14%, from 11 to 15%, from 12 to 16%, from 13 to 17%, from 14 to 18%, from 15 to 19%, from 16 to 20%, from 17 to 21%, from 18 to 22%, from 19 to 23%, from 20 to 24%, from 21 to 25%, from 22 to 26%, from 23 to 27%, from 24 to 28%, from 25 to 29%, from 26 to 30%, from 27 to 31%, from 28 to 32%, from 29 to 33%, from 30 to 34%, from 31 to 35%, from 32 to 36%, from 33 to 37%, from 34 to 38%, from 35 to 39%, from 36 to 40%, from 37 to 41%, from 38 to 42%, from 39 to 43%, from 40 to 44%, from 41 to 45%, from 42 to 46%, from 43 to 47%, from 44 to 48%, from 45 to 49%, from 46 to 50%, from 47 to 51%, from 48 to 52%, from 49 to 53%, from 50 to 54%, from 51 to 55%, from 52 to 56%, from 53 to 57%, from 54 to 58%, from 55 to 59%, from 56 to 60%, from 57 to 61%, from 58 to 62%, from 59 to 63%, from 60 to 64%, from 61 to 65%, from 62 to 66%, from 63 to 67%, from 64 to 68%, from 65 to 69%, from 66 to 70%, from 67 to 71%, from 68 to 72%, from 69 to 73%, from 70 to 74%, from 71 to 75%, from 72 to 76%, from 73 to 77%, from 74 to 78%, from 75 to 79%, from 76 to 80%, from 77 to 81%, from 78 to 82%, from 79 to 83%, from 80 to 84%, from 81 to 85%, from 82 to 86%, from 83 to 87%, from 84 to 88%, from 85 to 89%, from 86 to 90%, from 87 to 91%, from 88 to 92%, from 89 to 93%, from 90 to 94%, from 91 to 95%, from 92 to 96%, from 93 to 97%, from 94 to 98%, from 95 to 99%, or from 96 to 100% of a population or group of cancer cells.

In some cases, a personalized tumor vaccine can comprise administering a treatment to a cancer cell or population of cancer cells. A treatment can comprise an irradiation treatment. In some instances, an irradiation treatment can comprise using of radio waves, microwaves, infrared (IR), visible light, ultraviolet (UV), X-rays and gamma rays. A gamma ray irradiation treatment can comprise 1Gy, 10 Gy, 20 Gy, 30 Gy, 40 Gy, 50 Gy, 60 Gy, 70 Gy, 80 Gy, 90 Gy, 100 Gy, 110 Gy, 120 Gy, 130 Gy, 140 Gy, 150 Gy, 160 Gy, 170 Gy, 180 Gy, 190 Gy, 200 Gy, 210 Gy, 220 Gy, 230 Gy, 240 Gy, 250 Gy, 260 Gy, 270 Gy, 280 Gy, 290 Gy, 300 Gy, 310 Gy, 320 Gy, 330 Gy, 340 Gy, 350 Gy, 360 Gy, 370 Gy, 380 Gy, 390 Gy, 400 Gy, 410 Gy, 420 Gy, 430 Gy, 440 Gy, 450 Gy, 460 Gy, 470 Gy, 480 Gy, 490Gy, or 500Gy gamma radiation. A gamma ray irradiation can comprise from 1 to 25 Gy, from 2 to 26 Gy, from 3 to 27 Gy, from 4 to 28 Gy, from 5 to 29 Gy, from 6 to 30 Gy, from 7 to 31 Gy, from 8 to 32 Gy, from 9 to 33 Gy, from 10 to 34 Gy, from 11 to 35 Gy, from 12 to 36 Gy, from 13 to 37 Gy, from 14 to 38 Gy, from 15 to 39 Gy, from 16 to 40 Gy, from 17 to 41 Gy, from 18 to 42 Gy, from 19 to 43 Gy, from 20 to 44 Gy, from 21 to 45 Gy, from 22 to 46 Gy, from 23 to 47 Gy, from 24 to 48 Gy, from 25 to 49 Gy, from 26 to 50 Gy, from 27 to 51 Gy, from 28 to 52 Gy, from 29 to 53 Gy, from 30 to 54 Gy, from 31 to 55 Gy, from 32 to 56 Gy, from 33 to 57 Gy, from 34 to 58 Gy, from 35 to 59 Gy, from 36 to 60 Gy, from 37 to 61 Gy, from 38 to 62 Gy, from 39 to 63 Gy, from 40 to 64 Gy, from 41 to 65 Gy, from 42 to 66 Gy, from 43 to 67 Gy, from 44 to 68 Gy, from 45 to 69 Gy, from 46 to 70 Gy, from 47 to 71 Gy, from 48 to 72 Gy, from 49 to 73 Gy, from 50 to 74 Gy, from 51 to 75 Gy, from 52 to 76 Gy, from 53 to 77 Gy, from 54 to 78 Gy, from 55 to 79 Gy, from 56 to 80 Gy, from 57 to 81 Gy, from 58 to 82 Gy, from 59 to 83 Gy, from 60 to 84 Gy, from 61 to 85 Gy, from 62 to 86 Gy, from 63 to 87 Gy, from 64 to 88 Gy, from 65 to 89 Gy, from 66 to 90 Gy, from 67 to 91 Gy, from 68 to 92 Gy, from 69 to 93 Gy, from 70 to 94 Gy, from 71 to 95 Gy, from 72 to 96 Gy, from 73 to 97 Gy, from 74 to 98 Gy, from 75 to 99 Gy, from 76 to 100 Gy, from 77 to 101 Gy, from 78 to 102 Gy, from 79 to 103 Gy, from 80 to 104 Gy, from 81 to 105 Gy, from 82 to 106 Gy, from 83 to 107 Gy, from 84 to 108 Gy, from 85 to 109 Gy, from 86 to 110 Gy, from 87 to 111 Gy, from 88 to 112 Gy, from 89 to 113 Gy, from 90 to 114 Gy, from 91 to 115 Gy, from 92 to 116 Gy, from 93 to 117 Gy, from 94 to 118 Gy, from 95 to 119 Gy, from 96 to 120

Gy, from 97 to 121 Gy, from 98 to 122 Gy, from 99 to 123 Gy, from 100 to 124 Gy, from 101 to 125 Gy, from 102 to 126 Gy, from 103 to 127 Gy, from 104 to 128 Gy, from 105 to 129 Gy, from 106 to 130 Gy, from 107 to 131 Gy, from 108 to 132 Gy, from 109 to 133 Gy, from 110 to 134 Gy, from 111 to 135 Gy, from 112 to 136 Gy, from 113 to 137 Gy, from 114 to 138 Gy, from 115 to 139 Gy, from 116 to 140 Gy, from 117 to 141 Gy, from 118 to 142 Gy, from 119 to 143 Gy, from 120 to 144 Gy, from 121 to 145 Gy, from 122 to 146 Gy, from 123 to 147 Gy, from 124 to 148 Gy, from 125 to 149 Gy, from 126 to 150 Gy gamma radiation. A gamma ray irradiation can comprise from 50 Gy gamma radiation. A treatment or a gamma ray irradiation treatment can comprise 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, or 1 hr, 55 minutes, 55 minutes, 50 minutes, 45 minutes, 40 minutes, 35 minutes, 30 minutes, 25 minutes, 20 minutes, 15 minutes, 10 minutes, 5 minutes, 1 minutes, or less than 1 minute. A cancer cell can undergo one treatment. A cancer cell can undergo 2, 3, 4, 5, 6, 7, 8, 9, 10, or more treatments.

In some cases, a personalized tumor vaccine can comprise from 1×10^0 to 1×10^1 gamma ray irradiated cancer cells, from 5×10^0 to 5×10^1 gamma ray irradiated cancer cells, from 1×10^1 to 1×10^2 gamma ray irradiated cancer cells, from 5×10^1 to 5×10^2 gamma ray irradiated cancer cells, from 1×10^2 to 1×10^3 gamma ray irradiated cancer cells, from 5×10^2 to 5×10^3 gamma ray irradiated cancer cells, from 1×10^3 to 1×10^4 gamma ray irradiated cancer cells, from 5×10^3 to 5×10^4 gamma ray irradiated cancer cells, from 1×10^4 to 1×10^5 gamma ray irradiated cancer cells, from 5×10^4 to 5×10^5 gamma ray irradiated cancer cells, from 1×10^5 to 1×10^6 gamma ray irradiated cancer cells, from 5×10^5 to 5×10^6 gamma ray irradiated cancer cells, from 1×10^6 to 1×10^7 gamma ray irradiated cancer cells, from 5×10^6 to 5×10^7 gamma ray irradiated cancer cells, from 1×10^7 to 1×10^8 gamma ray irradiated cancer cells, from 5×10^7 to 5×10^8 gamma ray irradiated cancer cells, from 1×10^8 to 1×10^9 gamma ray irradiated cancer cells, from 5×10^8 to 5×10^9 gamma ray irradiated cancer cells, from 1×10^9 to 1×10^10 gamma ray irradiated cancer cells, from 5×10^9 to 5×10^10 gamma ray irradiated cancer cells, from 1×10^10 to 1×10^11 gamma ray irradiated cancer cells, from 5×10^10 to 5×10^11 gamma ray irradiated cancer cells, from 1×10^11 to 1×10^12 gamma ray irradiated cancer cells, from 5×10^11 to 5×10^12 gamma ray irradiated cancer cells, from 1×10^12 to 1×10^13 gamma ray irradiated cancer cells, from 5×10^12 to 5×10^13 gamma ray irradiated cancer cells, from 1×10^13 to 1×10^14 gamma ray irradiated cancer cells, from 5×10^13 to 5×10^14 gamma ray irradiated cancer cells, from 1×10^14 to 1×10^15 gamma ray irradiated cancer cells, from 5×10^14 to 5×10^15 gamma ray irradiated cancer cells, from 1×10^15 to 1×10^16 gamma ray irradiated cancer cells, from 5×10^15 to 5×10^16 gamma ray irradiated cancer cells, from 1×10^16 to 1×10^17 gamma ray irradiated cancer cells, from 5×10^16 to 5×10^17 gamma ray irradiated cancer cells, from 1×10^17 to 1×10^18 gamma ray irradiated cancer cells, from 5×10^17 to 5×10^18 gamma ray irradiated cancer cells, from 1×10^18 to 1×10^19 gamma ray irradiated cancer cells, from 5×10^18 to 5×10^19 gamma ray irradiated cancer cells, from 1×10^19 to 1×10^20 gamma ray irradiated cancer cells, or from 5×10^19 to 5×10^20 gamma ray irradiated gamma ray irradiated cancer cells. In some embodiments, a personalized tumor vaccine can comprise 1×10^5, 2×10^5, 3×10^5, 4×10^5, 5×10^5, 6×10^5, 7×10^5, 8×10^5, 9×10^5, 1×10^6, 2×10^6, 3×10^6, 4×10^6, 5×10^6, 6×10^6, 7×10^6, 8×10^6, 9×10^6, or 1×10^7 gamma ray irradiated cancer cells. A personalized tumor vaccine can comprise 1×10^6 gamma ray irradiated cancer cells. A personalized tumor vaccine can comprise 2×10^6 gamma ray irradiated cancer cells. A personalized tumor vaccine can comprise 2.5×10^6 gamma ray irradiated cancer cells. A personalized tumor vaccine can comprise 5×10^6 gamma ray irradiated cancer cells. A personalized tumor vaccine can comprise 5.5×10^6 gamma ray irradiated cancer cells.

In some instances, a treatment of obtaining an attenuated cancer cell can also comprise a chemical treatment. A chemical treatment can comprise reactive oxygen species (ROS) (e.g., superoxide, hydroxyl radicals and hydrogen peroxide), deaminating agents (e.g., nitrous acid, which can cause transition mutations by converting cytosine to uracil), polycyclic aromatic hydrocarbon (PAH), alkylating agents (e.g., ethylnitrosourea, nitrosamines, mustard gas and vinyl chloride), aromatic amines and amides (e.g., 2-Acetylaminofluorene), alkaloid from plants, bromine and some compounds that contain bromine in their chemical structure, sodium azide, psoralen, benzene, ethidium bromide, proflavine, daunorubicin, and some metals (arsenic, cadmium, chromium, nickel, iron, cobalt).

The Methods of Treating an Individual with Cancer

Described herein are methods of treating an individual with a cancer or tumor an effective amount of pharmaceutical composition that is subject-specific. In some cases, a subject-specific pharmaceutical composition can be a prophylactic or preventative composition. A subject-specific pharmaceutical composition can be a therapeutic or treatment pharmaceutical composition. In some embodiments, a subject-specific pharmaceutical composition can be administered to a subject in need thereof before the subject is diagnosed with a cancer. In some embodiments, a subject-specific pharmaceutical composition can be administered to a subject in need thereof after the subject is diagnosed with a cancer.

In some instances, a subject-specific pharmaceutical composition can comprise a phagocytosis stimulating agent or derivative herein and thereof; an immunostimulatory adjuvant or derivative herein and thereof; and an attenuated cancer cell or derivative herein and thereof.

In some instances, a subject specific pharmaceutical composition can comprise a phagocytosis stimulating agent or derivative herein and thereof; an immunostimulatory adjuvant or derivative herein and thereof; and from about 1.0×10^3 to about 1.0×10^7 attenuated cancer cells. In some instances, a subject specific pharmaceutical composition can comprise a mannan; an immunostimulatory adjuvant or derivative herein and thereof; and an attenuated cancer cell, cell population or derivative herein and thereof. In some instances, a subject specific pharmaceutical composition can comprise about 2 mg/dose to about 200 mg/dose mannan; an immunostimulatory adjuvant or derivative herein and thereof; and an attenuated cancer cell, cell population or derivative herein and thereof. In some cases, a subject specific pharmaceutical composition can comprise a phagocytosis stimulating agent or derivative herein and thereof conjugated to biocompatible anchor for cell membrane (BAM); an immunostimulatory adjuvant or derivative herein and thereof; and an attenuated cancer cell, cell population or derivative herein and thereof. In some cases, a subject specific pharmaceutical composition can comprise a mannan conjugated to BAM an immunostimulatory adjuvant or derivative herein and thereof; and an attenuated cancer cell, cell population or derivative herein and thereof. In some cases, a subject specific pharmaceutical composition can comprise a mannan conjugated to from about 0.2 mg/dose to about 20 mg/dose BAM; an immunostimulatory adjuvant or derivative herein and thereof; and an attenuated cancer cell, cell population or derivative herein and thereof. In some cases, a subject specific pharmaceutical composition can comprise a mannan conjugated to BAM comprising Formula I described herein and thereof; an immunostimulatory adjuvant or derivative herein and thereof; and an attenuated cancer cell, cell population or derivative herein and thereof.

In some instances, a subject specific pharmaceutical composition can comprise a phagocytosis stimulating agent or derivative herein and thereof; a Toll like receptor (TLR) agonist; and an attenuated cancer cell, cell population or derivative herein and thereof. In some cases, a subject specific pharmaceutical composition can comprise a phagocytosis stimulating agent or derivative herein and thereof; R-848, poly(I:C), lipoteichoic acid (LTA), or combinations thereof; and an attenuated cancer cell, cell population or derivative herein and thereof. In some cases, a subject specific pharmaceutical composition can comprise a phagocytosis stimulating agent or derivative herein and thereof; from about 0.05 mg/dose to about 5 mg/dose R-848, poly (I:C), lipoteichoic acid (LTA), or combinations thereof; and an attenuated cancer cell, cell population or derivative herein and thereof. In some cases, a subject specific pharmaceutical composition can comprise a phagocytosis stimulating agent or derivative herein and thereof; R-848, from about 0.05 mg/dose to about 5 mg/dose poly(I:C), lipoteichoic acid (LTA), or combinations thereof; and an attenuated cancer cell, cell population or derivative herein and thereof. In some cases, a subject specific pharmaceutical composition can comprise a phagocytosis stimulating agent or derivative herein and thereof; R-848, poly(I:C), from about 0.05 mg/dose to about 5 mg/dose lipoteichoic acid (LTA), or combinations thereof; and an attenuated cancer cell, cell population or derivative herein and thereof.

In some instances, a subject specific pharmaceutical composition can comprise a phagocytosis stimulating agent or derivative herein and thereof; an anti-CD40 antibody; and an attenuated cancer cell, cell population or derivative herein and thereof. In some instances, a subject specific pharmaceutical composition can comprise a phagocytosis stimulating agent or derivative herein and thereof; from about 0.04 mg/dose to about 4 mg/dose anti-CD40 antibody; and an attenuated cancer cell, cell population or derivative herein and thereof.

In some instances, a subject specific pharmaceutical composition can comprise a mannan attached to BAM, a R-848, a poly(I:C), an LTA, an anti-CD40 antibody, and irradiated cancer cells. In some instances, a subject specific pharmaceutical composition can comprise from about 0.05 mg/dose to about 5 mg/dose mannan attached to from about 0.05 mg/dose to about 5 mg/dose BAM, from about 0.05 mg/dose to about 5 mg/dose R-848, from about 0.05 mg/dose to about 5 mg/dose poly(I:C), from about 0.05 mg/dose to about 5 mg/dose LTA, from about 0.04 mg/dose to about 4 mg/dose anti-CD40 antibody, and from about 1.0×10^3 to about 1.0×10^7 irradiated cancer cells.

Described herein are also methods of treating an individual in need thereof with an effective amount of a personalized cancer described herein and thereof.

Methods of Making a Personalized Tumor Vaccine or Pharmaceutical Composition

A personalized tumor vaccine or a pharmaceutical composition can comprise mixing an irradiated cell population extracted from a tumor of a subject with a phagocytosis stimulating agent and an immunostimulatory adjuvant simultaneously. In other cases, a personalized tumor vaccine or a pharmaceutical composition can comprise mixing an irradiated cell population extracted from a tumor of a subject with a phagocytosis stimulating agent and an immunostimulatory adjuvant sequentially. A personalized tumor vaccine or a pharmaceutical composition can comprise mixing an irradiated cell or cell population extracted from a tumor of a subject and a mannan-BAM, R-848, anti-CD40 mAb, poly(I:C), and LTA to form a personalized tumor vaccine.

Excipient

A personalized tumor vaccine or a pharmaceutical composition can comprise an excipient. In some instances, an excipient can comprise a preservative, adjuvant, diluent, or stabilizer. In some instances, an excipient can prevent contamination. In some instances, an excipient can stabilize vaccine potency during storage. In some instances, an excipient can comprise monosodium glutamate, sucrose, D-mannose, D-frusctose, dextrose, human serum albumin, potassium phosphate, plasdone C, anhydrous lactose, microcrystalline, cellulose, polacrilin potassium, magnesium stearate, cellulose acetate phthalate, alcohol, acetone, caster oil, aluminum hydroxide, sodium chloride, benzethonium chloride, formaldehyde, glycerin, asparagine, citric acid, magnesium sulfate, iron ammonium citrate, sodium carbonate, essential amino acid, L-phenylalanine, non-essential amino acids, L-arginine hydrochloride, D-trehalose dihydrate, D-sorbitol, trometamol, thimerosal, gelatin, urea, isotonic sodium chloride, glutaraldehyde, 2-phenoxyethanol, polysorbate 80 (Tween 80), neomycin sulfate, polymyxin B, 2-phenoxyethanol, neomycin, polymyxin B sulfate, bovine serum albumin, yeast protein, streptomycin sulfate, ammonium thiocyanate, alum, aluminum-containing compounds, host cell DAN benzonase, rice protein, amorphous aluminium hydrozyphosphate sulfate, MRC-5 cellular proteins, formalin, saline, Tween20, aminoglycoside antibiotic, sodium borate, disodium phosphate dihydrate, sodium dihydrogen phosphate dihydrate, yeast DNA, phosphorothioate linked oligoeoxynucleotide, dibasic dodecahydrate, monobasic dehydrate, phosphate buffer, L-histidine, calcium chloride, sodium taurodeozycholate, ovalbumin, beta-propriolactone, hydrocortisone thimerosal, squalene, sorbitan trioleate, citric acid monohydrate, kanamycin, barium, hydrocortisone, egg proteins, cetyltrimethylammonium bromide (CTAB), TRITON X-100, alpha-tocopheryl hydrogen succinate, gentamicin sulfate, maltodextrin 17, maltodextrin 4, arginine, maltose, histidine, calcium heptagluconate, maltodextrin 13, heparin, raffinose, myo-inositol, sucrose, sorbitol, arabitol, fructose, potassium gluconate, adonitol, xylitol, sodium thiosulfate, asparigine, 2-hydroxypropyl--cyclodextrin, TRIS, sodium citrate, dulcitol, glycerol, any derivatives herein and thereof, any combinations herein and thereof.

In some instances, an excipient of a personalized cancer vaccine or a pharmaceutical composition can comprise amorphous sugars. In some instances, an amorphous sugar can comprise bulking agents and protein stabilizers. In some instances, an amorphous sugar can comprise glass-forming sugars. In some embodiments, an amorphous sugar can comprise sucrose, raffinose, trehalose, stachyose, lactose, maltose, any derivatives or combinations herein and thereof. A sugar can comprise an amount effective for volume increase or an amount effective for protein stabilization. Based on weight percent units, the sugar can be present in the range of about 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100%, by weight.

In some instances, an excipient of a personalized cancer vaccine or a pharmaceutical composition can comprise a thickener. A thickener can comprise polymeric materials. A polymeric material can comprise hydroxyethylcellulose (HEC), hydroxypropylmethylcellulose (HPMC), hydroxypropylcellulose (HPC), methylcellulose (MC), hydroxyethylmethylcellulose (HEMC), or ethylhydroxyethylcellulose (EHEC) and other cellulose derivatives.

In some embodiments, an excipient can increase the stability of an antigen, phagocytosis stimulating agent, or cell or cell population in a dry solid formulation as compared to a dry solid formulation of the antigen, phagocytosis stimulating agent, or cell or cell population without any excipients. In some cases, at least one excipient can be used in a personalized tumor vaccine. In some cases, multiple excipients can provide a greater effect than that of any excipient alone, and in some cases provides a greater than additive effect of the multiple excipients on the stability of the antigen, phagocytosis stimulating agent, or cell or cell population.

An excipient or excipients can be present in the composition in a total amount of about 0%, 5%, 10%, 15%, 20%, 25%, 30%, 35%, 40%, 45%, 50%, 55%, 60%, 65%, 70%, 75%, 80%, 85%, 90%, 95%, or 100%, by weight or volume, of a personalized tumor vaccine. In some instances, an excipient or excipients can be present in the composition in a total amount of 0-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100%, by weight or volume, of a personalized tumor vaccine.

A personalized tumor vaccine or a pharmaceutical composition can comprise a diluent. A diluent can comprise water, PBS buffer, sodium chloride, MenCWY, DTaP-IPV, calcium carbonate, xanthan, adjuvants described herein and thereof, and derivatives herein and thereof, or any combinations herein and thereof.

Administration of a personalized tumor vaccine or pharmaceutical composition

In some cases, a personalized tumor vaccine can comprise packing the vaccine into a composition or formulation for delivery or administration in a subject. In some cases, an administration of a composition or a pharmaceutical composition provided herein can refer to methods that can be used to enable delivery of the vaccine or pharmaceutical composition to the desired site of biological action. Delivery can include direct application to the affect tissue or region of the body. Delivery can include intracranial injection. Delivery can include a parenchymal injection, an intra-thecal injection, an intra-ventricular injection, or an intra-cisternal injection. A composition provided herein can be administered by any method. A method of administration can be by inhalation, intraarterial injection, intracerebroventricular injection, intracisternal injection, intramuscular injection, infraorbital injection, intraparenchymal injection, intraperitoneal injection, intraspinal injection, intrathecal injection, intravenous injection, intraventricular injection, stereotactic injection, subcutaneous injection, or any combination thereof. Delivery can include parenteral administration (including intravenous, subcutaneous, intrathecal, intraperitoneal, intramuscular, intravascular or infusion), oral administration, inhalation administration, intraduodenal administration, rectal administration. Delivery can include topical administration (such as a lotion, a cream, an ointment) to an external surface of a surface, such as a skin. In some cases, administration is by parenchymal injection, intra-thecal injection, intra-ventricular injection, intra-cisternal injection, intravenous injection, or intranasal administration or any combination thereof. In some instances, a subject can administer the composition in the absence of supervision. In some instances, a subject can administer the composition under the supervision of a medical professional (e.g., a physician, nurse, physician's assistant, orderly, hospice worker, etc.). A medical professional can administer the composition. In some cases, a cosmetic professional can administer the composition.

The methods of treating an individual with cancer described herein can comprise administration of a personalized tumor vaccine or a pharmaceutical composition in an individual with a cancer or suspected of a cancer. The methods of treating an individual with cancer described herein can also comprise administration of a personalized tumor vaccine or a pharmaceutical composition in an individual without a cancer or suspected of a cancer. In some embodiments, the cancer comprises Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloepithelioma, Melanoma, Meningioma, Merkel Cell Carcinoma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple myeloma, Mycosis Fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neurofibroma, Neuroma, Nodular melanoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral cancer, Oropharyngeal Cancer, Osteosarcoma, Ovarian cancer, Ovarian Epithelial Cancer, Ovarian Germ Cell Tumor, Ovarian Low Malignant Potential Tumor, Paget's disease of the breast, Pancoast tumor, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, or Wilms' tumor.

Administration or application of a personalized tumor vaccine or a pharmaceutical composition can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. A treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

Administration or application of a composition disclosed herein can be performed for a treatment duration of at least about 1 week, at least about 1 month, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or more. Administration can be performed repeatedly over a lifetime of a subject, such as once a month or once a year for the lifetime of a subject. Administration can be performed repeatedly over a substantial portion of a subject's life, such as once a month or once a year for at least about 1 year, 5 years, 10 years, 15 years, 20 years, 25 years, 30 years, or more.

In some cases, an administration of any personalized tumor vaccines or pharmaceutical compositions provided herein, including pharmaceutical compositions can be in an effective amount, for example to reduce a symptom of a disease or condition and/or to reduce a disease or condition. In some instances, an effective amount can be sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above.

Dosing

Administration or application of personalized tumor vaccines or pharmaceutical compositions disclosed herein can be performed at least 1, 2, 3, 4, 5, 6, 7, 8, 9, 10, 11, 12, 13, 14, 15, 16, 17, 18, 19, 20, 21, 22, 23, or 24 times a day. In some cases, administration or application of personalized tumor vaccines or pharmaceutical compositions disclosed herein can be performed at least 1, 2, 3, 4, 5, 6, 7, 8, 9, 10, 11, 12, 13, 14, 15, 16, 17, 18, 19, 20, or 21 times a week. In some cases, administration or application of personalized tumor vaccines or pharmaceutical compositions disclosed herein can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

A personalized tumor vaccines or pharmaceutical composition of the present disclosure can be administered/applied as a single dose or as divided doses. In some cases, the personalized tumor vaccines or pharmaceutical compositions described herein can be administered at a first time point and a second time point. In some cases, a personalized tumor vaccines or pharmaceutical composition can be administered such that a first administration is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, 2 months, 3 months, 4 months, 5 months, 6 months, 7 months, 8 months, 9 months, 10 months, 11 months, 1 year or more.

An effective amount of a personalized tumor vaccines or pharmaceutical composition can reduce the size of a tumor. A personalized tumor vaccines or pharmaceutical composition can decrease the size of a tumor by 0%, 5%, 10%, 15%, 20%, 25%, 30%, 35%, 40%, 45%, 50%, 55%, 60%, 65%, 70%, 75%, 80%, 85%, 90%, 95%, or 100% of the size of the tumor before the administration of the personalized tumor vaccines or pharmaceutical composition. In some instances, an effective amount of a personalized tumor vaccines or pharmaceutical composition can decrease the size of a tumor by 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100% of the size of the tumor before the administration of the personalized tumor vaccines or pharmaceutical composition.

An effective amount of a personalized tumor vaccines or pharmaceutical composition can reduce the number of cancer cells. A personalized tumor vaccines or pharmaceutical composition can reduce the number of cancer cells by 0%, 5%, 10%, 15%, 20%, 25%, 30%, 35%, 40%, 45%, 50%, 55%, 60%, 65%, 70%, 75%, 80%, 85%, 90%, 95%, or 100% of number of the cancer cells before the administration of the personalized tumor vaccines or pharmaceutical composition. In some instances, an effective amount of a personalized tumor vaccines or pharmaceutical composition can decrease the number of cancer cells by 1-10%, 5-15%, 10-20%, 15-25%, 20-30%, 25-35%, 30-40%, 35-45%, 40-50%, 45-55%, 50-60%, 55-65%, 60-70%, 65-75%, 70-80%, 75-85%, 80-90%, 85-95%, or 90-100% of the number of the cancer cells before the administration of the personalized tumor vaccines or pharmaceutical composition.

An effective amount of a personalized tumor vaccines or pharmaceutical composition can extend the life-span of a subject administered with the personalized tumor vaccines or pharmaceutical composition. In some instances, an effective amount of a personalized tumor vaccines or pharmaceutical composition can extend the life-span of a subject administered with the personalized tumor vaccines or pharmaceutical composition by 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, or more than 50 years. In some instances, an effective amount of a personalized tumor vaccines or pharmaceutical composition can extend the life-span of a subject administered with the personalized tumor vaccines or pharmaceutical composition by an amount of time from 1 day to 1 month, from 25 days to 6 months, from 5 months to 12 months, from 10 months to 2 years, from 1 year to 5 years, from 4 years to 10 years, from 9 years to 15 years, from 14 years to 20 years, from 19 years to 25 years, from 24 years to 30 years, from 29 years to 35 years, from 34 years to 40 years, from 39 years to 45 years, or from 44 years to 50 years.

An effective amount of a personalized tumor vaccines or pharmaceutical composition can delay the onset of a cancer of a subject administered with the personalized tumor vaccines or pharmaceutical composition. In some instances, an effective amount of a personalized tumor vaccines or pharmaceutical composition can delay the onset of a cancer of a subject administered with the personalized tumor vaccines or pharmaceutical composition by 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, or more than 50 years. In some instances, an effective amount of a personalized tumor vaccines or pharmaceutical composition can delay the onset of a cancer of a subject administered with the personalized tumor vaccines or pharmaceutical composition by an amount of time from 1 day to 1 month, from 25 days to 6 months, from 5 months to 12 months, from 10 months to 2 years, from 1 year to 5 years, from 4 years to 10 years, from 9 years to 15 years, from 14 years to 20 years, from 19 years to 25 years, from 24 years to 30 years, from 29 years to 35 years, from 34 years to 40 years, from 39 years to 45 years, or from 44 years to 50 years.

EXAMPLES

These examples are provided for illustrative purposes only and not to limit the scope of the claims provided herein.

Example 1: A Mouse Model of Subcutaneous Primary and Metastatic Distant Tumors Provided herein are methods for creating a mouse model to study subcutaneous primary and metastatic distant tumors.

Cell Lines

CT26 colon carcinoma cells were obtained from ATCC. Tumor cells were cultured in complete medium (RPMI 1640, Gibco) containing 10% (vol/vol) FBS (Gibco), 100 Uml-1 penicillin, 100 μgml-1 streptomycin (Gibco). All cell lines used were shown to be negative for *mycoplasma* contamination using PCR amplification.

a CT26 Tumor-Bearing Mouse Model

To establish a mouse model to study primary and metastatic distant tumors, tumor cells were injected into the right and left flank, respectively, to form the primary tumor and distant metastatic tumor.

Figure 1B:
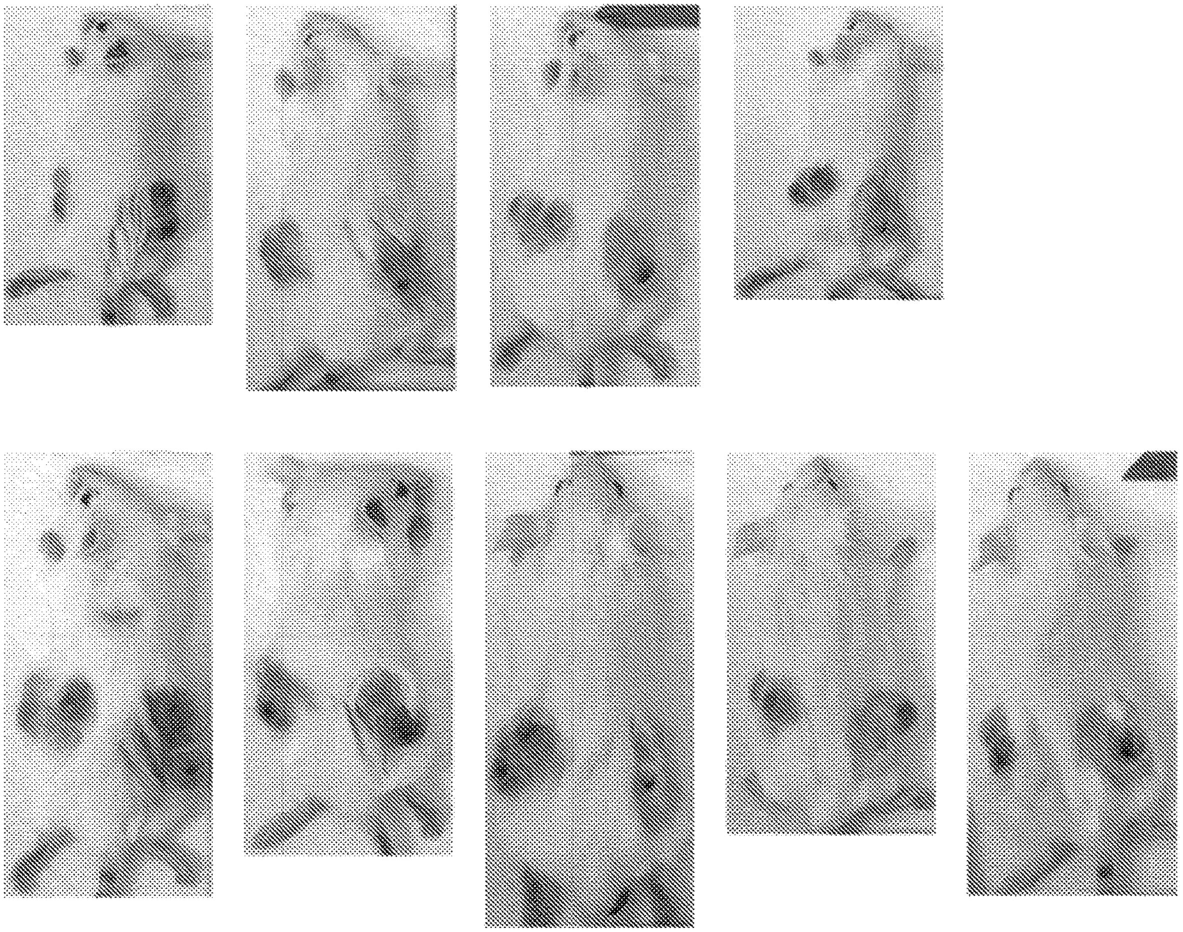

Mice were maintained, and experiments were conducted with the approval of the NCI Animal Use and Care Committees. Female BALB/c (6-8-week-old) were purchased from Charles River Laboratory. 5.5×10^5 and 2.5×10^5 CT26 cells suspended in 100-200 μL PBS were subcutaneously injected into 101 and 102 on right or left flanks respectively, as shown in FIG. 1A. Tumor volume was measured twice per week using a caliper and calculated according to the formula: Volume ($mm^3$)=L×W2/2, where L is the length and W is the width of the tumor (in millimeters). FIG. 1B shows representative pictures of CT26 tumor-bearing mice 10 days after injection of saline.

Statistics

Sample sizes of animal studies were determined empirically. Pre-established starting tumor size used as inclusion criteria for randomization was determined by pilot experiments. Investigators not blinded from the group allocation during outcome measurement performed randomization manually. Survival end points for all animal studies were defined according to the following criteria: (1) tumor volume exceeding 2000 $mm^3$, (2) tumor diameter exceeding 2 cm, (3) severe non-healing skin necrosis over the tumor.

GraphPad Prism software was used to analyze tumor growth and test the statistical differences in mean tumor volumes between treatment groups reached using the Mann-Whitney test and Kruskal-Wallis with Dunn's multiple comparisons test. P values <0.05 were considered statistically significant. For survival analyses, Kaplan-Meier curves were generated. P values were calculated using the log-rank test (Mantel-Cox).

Example 2: In Situ MBTA Injection at Primary Tumors Suppresses Distant Tumor Growth Via a T-Cell Dependent Subject-Specific Immune Response Provided herein are methods for using MBTA to treat primary and distant tumor growth.

MBTA Immunotherapy Strategy

Figure 2A:
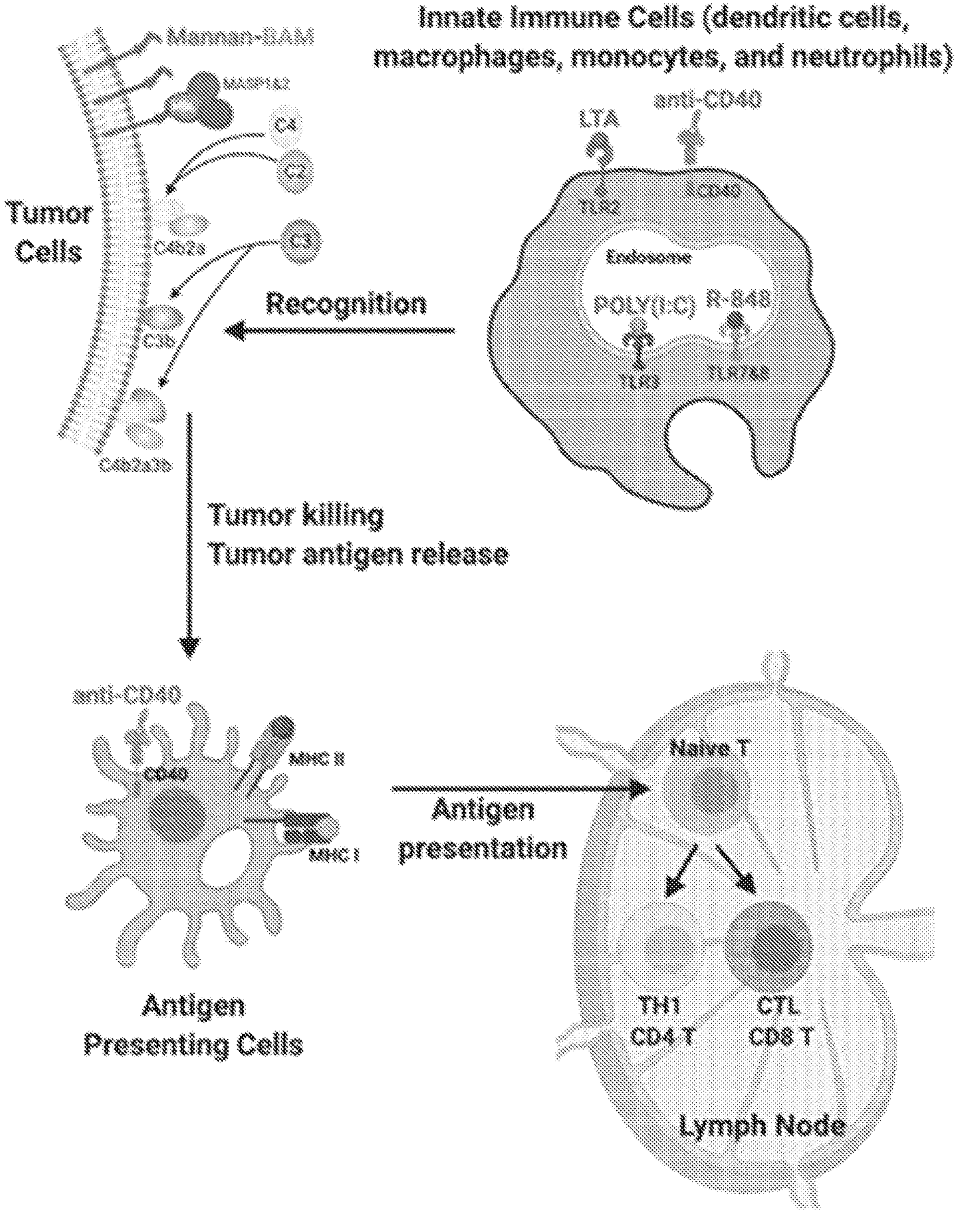
FIGS. 2A-H show that in situ MBTA injection at representative primary tumors induces a potent and systemic subject-specific adaptive immune response.

FIG. 2A shows the general strategy of the MBTA treatment: To bolster mannan-BAM's inductive effect on innate immune cells—such as dendritic cells, macrophages, monocytes, and neutrophils-three TLR ligands (Lipo-teichoic acid (LTA), polyinosinic-polycytidylic acid (poly(I:C)), Resiquimod (R-848)), and immunostimulatory anti-CD40-mAb (recombinant mouse CD40 fusion protein, Bio X Cell, catalog number: BE0016-2, clone number: FGK4.5/FGK45) were incorporated as adjuvants. LTA from *Bacillus subtilis* activates TLR2 mediated inflammatory pathways known to increase TNFα secretion. Poly(I:C), a synthetic analog of viral dsRNA, activated TLR3 mediates signaling previously demonstrated to activate APCs, modulate the phenotype of tumor associated macrophages to become increasingly immunosupportive, and induce tumor cell apoptosis. R-848, an imidazoquinolinamine and synthetic analog of viral ssRNA, activates TLR7/8 pathways, resulting in the induction of Th1 cell-mediated immunity. In some instances, anti-CD40-mAb was introduced to mimic the natural ligand to activate a CD40 receptor, a tumor necrosis factor receptor, on the T-cells.

Dendritic cells (DCs) is used for the induction of an antitumor response by a personalized tumor vaccine. DCs are 100-fold more effective in inducing the proliferation of T-cells than B-cells do. DCs are the most potent antigen-presenting cells that prime naïve T-cells into antigen-specific cytotoxic $CD4^+$ or $CD8^+$ T lymphocytes. DCs can present exogenous antigens on major histocompatibility complex (MHC) class II molecules or endogenous antigens on MHC class I molecules. In some cases, DCs can also present exogenous antigens on MHC molecules, which is necessary for the generation of the cytotoxic T lymphocytes. DCs can also induce T helper (Th) 1, Th2, or Th17 polarization response.

DCs need to undergo a maturation process in order to primer naïve T-cells. Immature DCs can be induced to undergo maturation by a combination of PAMPs, inflammatory cytokines, and TLR agonistics; thymic stromal lymphopoietin; TLR agonists and CD40 agonist; or Wnt-B-cadherin. For example, in the personalized tumor vaccine described herein, DCs can be matured by a combination of LTA, Poly(I:C), R-848, and anti-CD40 mAb.

DCs represent a link between innate immunity and adaptive immune response: DCs, as innate immune response cells, can engulf or phagocytose pathogens, such as the attenuated cancer cell associated with mannan-BAM They then migrated to the lymph node for the activation of adaptive immune cells T-cells. There, DCs digest and express antigens from the phagocytosed attenuated cancer cells on their cell surface using MHC molecules on the surface of their cell membrane. The presentation of cancer antigens then activates T-cell differentiation and proliferation, activating an immunological memory, long after even if the pathogens are eliminated. When the immune system encounters a similar or same pathogen, a potent immune response by T-cells and B-cells are, triggered i.e., the adaptive immune response. DCs, therefore, represent a physical linkage between innate and adaptive immune response.

Drug Synthesis

The linkage of mannan to BAM (Mannan-BAM) facilitated anchoring of mannan to the tumor cell membranes via BAM's hydrophobic oleyl group. BAM subsequently exploited mannan's recognition by pattern recognition receptors on innate immune cells via the recruitment of the MASP1 & MASP2 proteins to activate the complement components (such as C2, C3, and C4), leading to the opsonphagocytosis of the tumor cells by the innate immune cells.

After killing the tumor cells, ligation of anti-CD40-mAb to the CD40 receptor activates antigen presenting cells to present the tumor antigens to naïve T-cells in the lymph node. The naïve T-cells then differentiated into helper $CD4^+$ and cytotoxic $CD8^+$ T-cells for long-lasting adaptive immune response.

Mannan and Poly(I:C) were obtained from Sigma-Aldrich (St. Louis, Mo). LTA was obtained from Sigma-Aldrich (St. Louis, Mo) and InvivoGen (San Diego, CA). R-848 was obtained from Tocris Bioscience (Minneapolis MN). In some instances, anti-mouse CD40 (clone: FGK4.5/GFK45) was obtained from BioXCell (West Lebanon, NH). Biocompatible anchor for cell membrane (BAM) was obtained from NOF America Corporation (White Plains, NY).

Mannan-BAM synthesis was performed as previously reported (Janotová et al. PLOS One 2014, 9, e85222. Aminated mannan was prepared by reductive amination, as previously reported (Torosantucci et al. J. Exp. Med. 2005, 202, 597). Mannan solution in an environment of ammonium acetate (300 mg mL-1) was reduced by 0.2 m sodium cyanoborohydride at pH 7.5 and 50 °C for five days. Solution was further dialyzed using MWCO 3500 dialysis tubing (Serva, Heidelberg, Germany) against PBS at 4 °C overnight. Binding of BAM on amino group of mannan was performed at pH 7.3 according to Kato et al. (Biotechnol. Prog. 2004, 20, 897). N-hydroxysuccinimide (NHS) group of BAM reacted with amino group of mannan within one hour at room temperature. Solutions obtained after dialysis was stored frozen at −20 °C until use.

In Situ MBTA Injections

For in situ MBTA injections, 50 µL of the therapeutic mixture consisting of 0.5 mg R-848 (HCl form), 0.5 mg poly(I:C), 0.5 mg LTA, and 0.4 mg anti-CD40 per mL of 0.2 mM mannan-BAM in PBS was injected intratumorally.

MBTA Treatment of Primary and Distant Tumors

The effectiveness of the MBTA treatment was examined using the mouse model of Example 1.

Figure 2B:
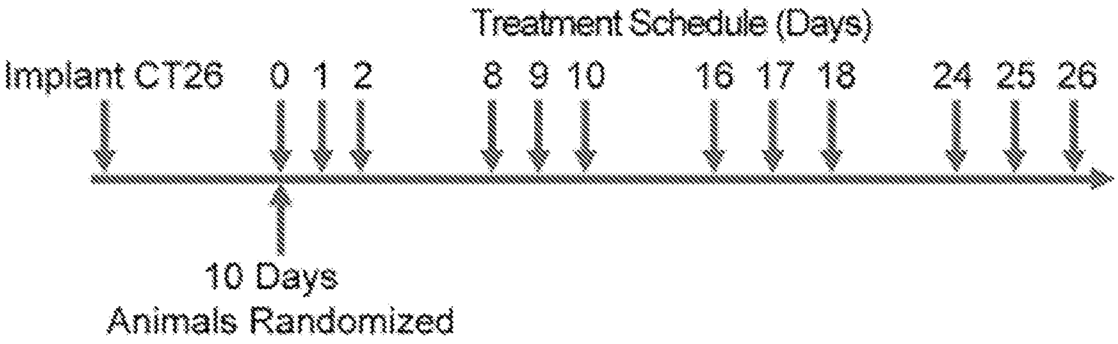
Figure 2C:
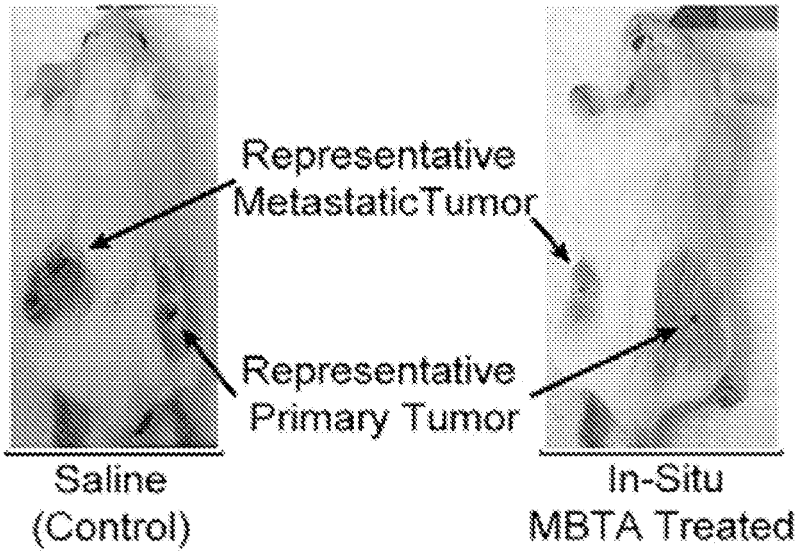

As referred in FIG. 2B, after 10 days, mice bearing left flank tumors (average left flank tumor volume-31.3 $mm^3$) were randomized into two treatment arms: normal saline (control) and in situ injection of MBTA into right flank tumors. Treatments were administered every day for 3 days then repeated weekly for a total of 4 weeks. Tumor growth was assessed twice a week until survival end point. Experiment was performed twice. Representative pictures of these mice were shown in FIG. 2C.

Figure 2D:
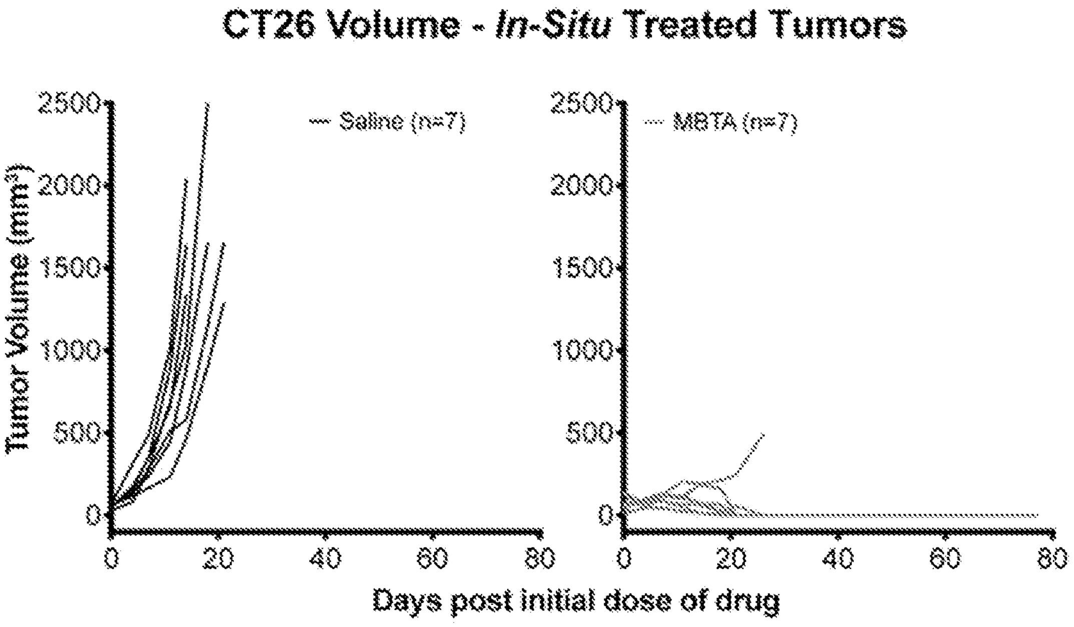
Figure 2E:
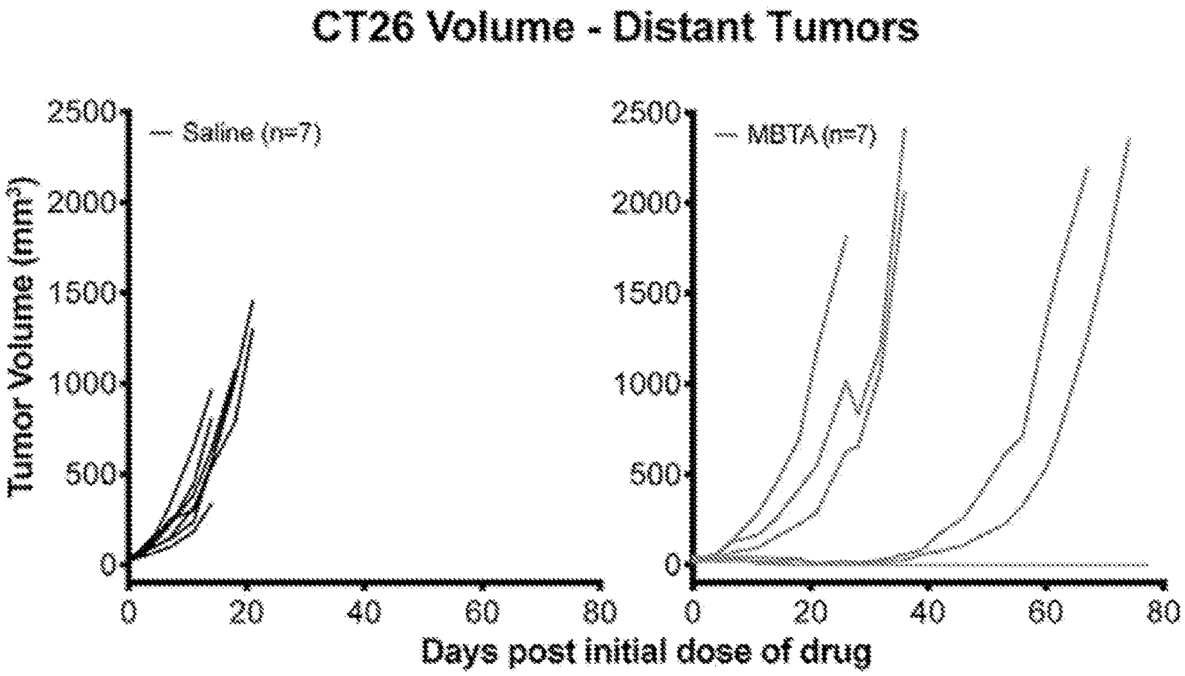

As referred in FIGS. 2D and 2E, four days after the start of treatment, both right and left flank tumor volumes show a statistically significant difference between in situ MBTA injected mice versus saline treated mice (median tumor volumes±SEM of in situ MBTA versus saline treated mice: right flank treated tumors—74.4±8.8 versus 150.2±28.1 $mm^3$. p=0.0041; left flank distant tumors—39.7±5.3 versus 111.0±11.5 $mm^3$, p=0.0006).

Figure 2F:
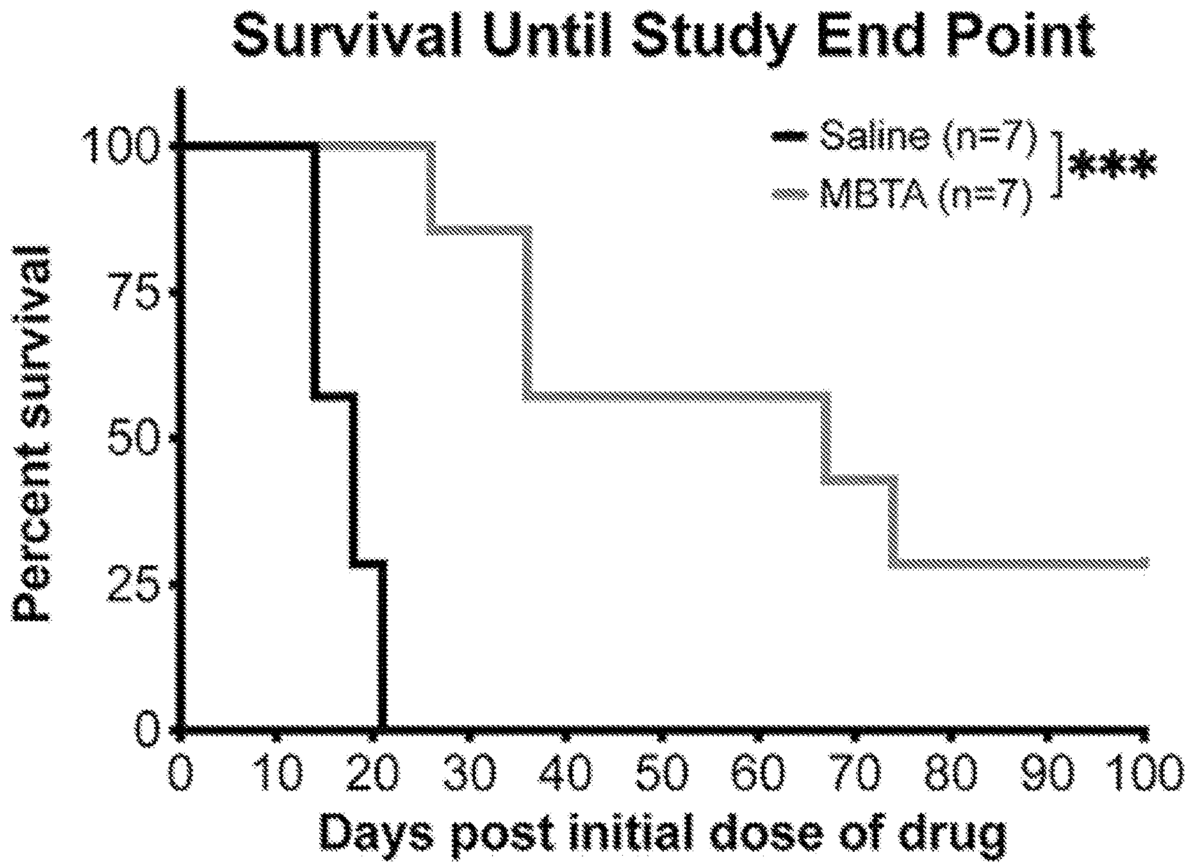

The in situ MBTA injected mice had a significantly improved survival over the saline treated mice (median survival±SEM of in situ MBTA versus saline treated mice: 67±11.7 versus 18±1.2 days, p=0.0002 by Log-rank test), as shown in FIG. 2F. 2/7 (28.6%) The MBTA treated mice achieved complete regression (CR) for the duration of the study. Therefore, the in situ injection of MBTA into the primary tumors suppressed the distal tumor growth.

Figure 2G:
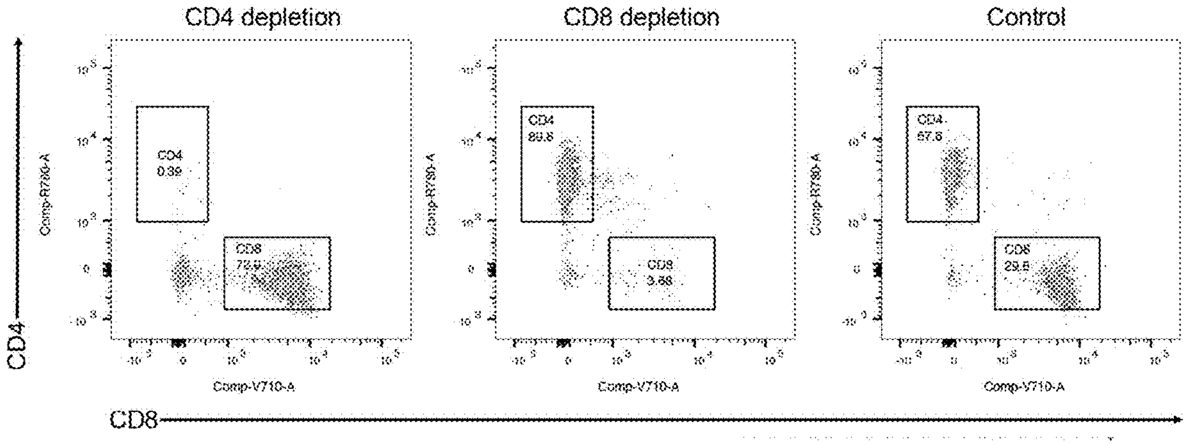
Figure 2H:
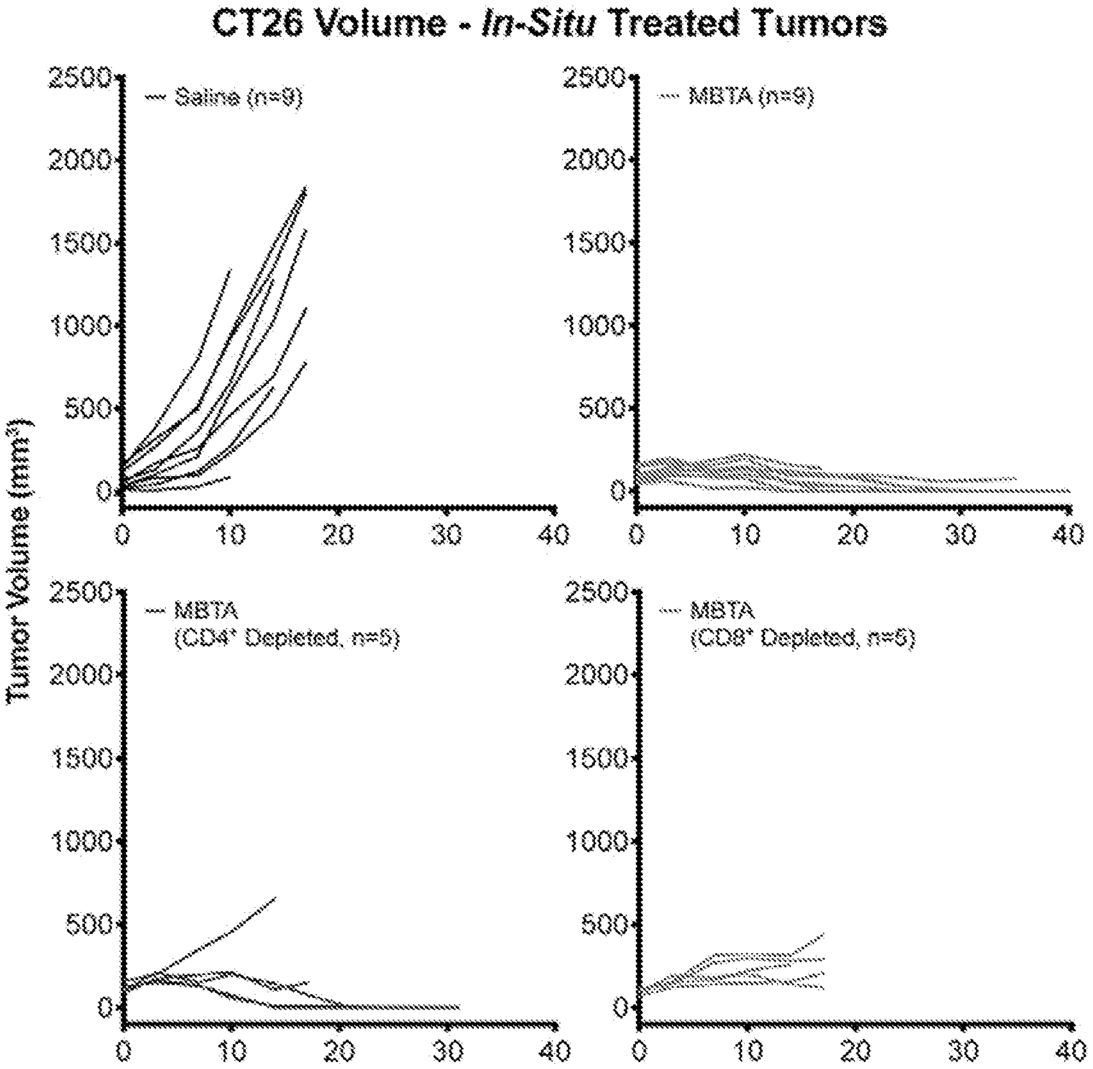
Figure 2I:
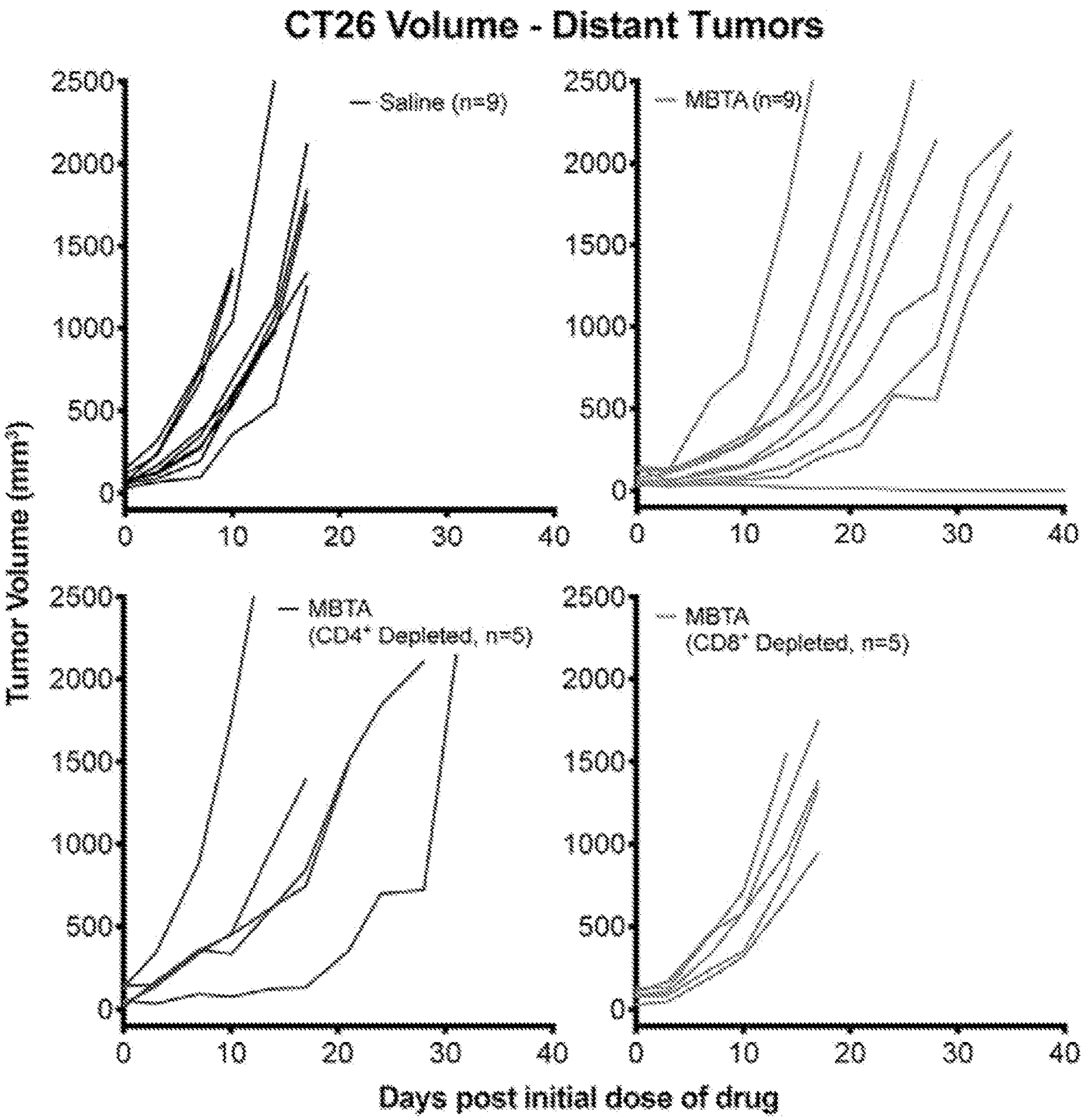
FIG. 2I depicts line graphs showing the relationship of the metastatic distant tumor volume ($mm^3$) and time for the CT26 tumor-bearing mice with the primary tumor injected in situ with saline (n=9, top left panel), MBTA (n=9, top right panel), MBTA plus $CD4^+$ cells depletion (n=5, bottom left panel), and MBTA plus $CD8^+$ cells depletion (n=5, bottom right panel). The metastatic distant tumors of the mice with the in situ MBTA injection and the non-T-cells or $CD4^+$ cells depletion grew slower than those with the saline injection or MBTA injection plus the $CD8^+$ cells depletion.

To determine if the observed antitumor effect is mediated by T-cells, antibodies were administered both prior to and during treatment to deplete $CD4^+$ or $CD8^+$ T-cells in the CT26 tumor-bearing mice. Mice in the $CD8^+$ and $CD4^+$ depletion group were injected with 250 µg of CD8-depleting antibodies (clone 53-6.7; BioXcell) and CD4-depleting antibodies (clone GK1.5; BioXcell), respectively. Injections were given −2 day, −1 day, and on the day of therapy initiation (day −2, −1, 0), then weekly thereafter. The T-cell depletion was confirmed via flow cytometry 16 days after initiating treatment, as shown in FIG. 2G. The $CD4^+$ and $CD8^+$ T-cell depleted mice were subjected to the same in situ MBTA treatment schedule as shown in FIG. 2B. FIGS. 2H and 2I show that ten days after the treatment, both primary and distant tumor showed a statistically significant difference in tumor volumes (p=0.0019 and 0.0057) corresponding to the non-T-cell depleted in situ MBTA treated mice, $CD4^+$ depleted in situ MBTA treated mice, $CD8^+$ depleted in situ MBTA treated mice, and saline treated mice (median tumor volumes±SEM: CD4+ depleted versus non-T-cell depleted in situ MBTA treated mice—199.6±71.3 versus 136.9±19.8 $mm^3$, Bonferroni adjusted p>0.05).

The primary tumor volumes of both $CD8^+$ depleted in situ MBTA treated mice and saline treated control mice were significantly larger than those of non-T-cell depleted in situ MBTA treated mice (median tumor volumes±SEM: $CD8^+$ depleted versus non-T-Cell depleted in situ MBTA treated mice—222.4±31.9 versus 136.9±19.8 $mm^3$. Bonferroni adjusted p=0.0420; saline treated versus non-T-cell depleted in situ MBTA treated mice—595.4±133.6 versus 136.9±19.8 $mm^3$. Bonferroni adjusted p=0.0111). Therefore, $CD8^+$ T-cells significantly affect tumor growth control of the primary tumors.

Figure 2J:
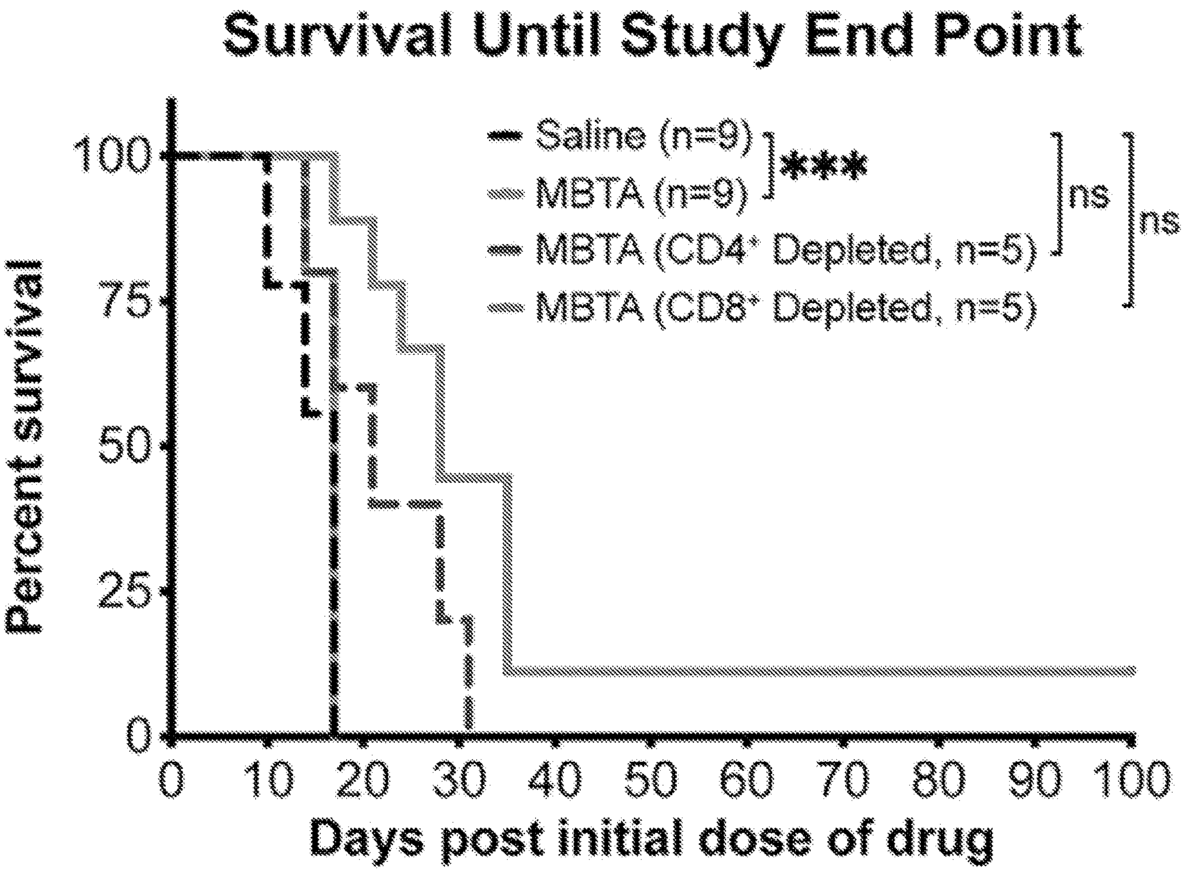
FIG. 2J depicts the cumulative survival curves of the CT26 tumor-bearing mice with the in situ injection at the primary tumor. By 30 days, all mice received the saline control (n=7), the MBTA injection with $CD4^+$ or $CD8^+$ cell depletion died, while all mice received the MBTA treatment (n=7) survived. At least 10% of the MBTA treated mice without T-cell depletion survived 100 days after the treatment. * p=0.0002, ns=not significant by Log-rank (Mantel-Cox) test.

No significant difference in distant tumor volumes was detected between $CD4^+$ or $CD8^+$ depleted in situ MBTA treated mice and the saline treated control mice (median tumor volumes±SEM: $CD4^+$ depleted in situ MBTA treated versus saline treated mice—448.7±291.1 versus 607.4±121.1 $mm^3$. Bonferroni adjusted p>0.05; $CD8^+$ depleted in situ MBTA treated versus saline treated mice—582.5±75.6 versus 607.4±121.1 $mm^3$. Bonferroni adjusted p>0.05), as shown in FIG. 2I. The distant tumor of the non-T-cell depleted in situ MBTA treated mice was significantly smaller than that of the saline treated control mice (median tumor volumes±SEM: non-T-cell depleted in situ MBTA treated versus saline treated mice—158.7±72.5 versus 607.4±121.1 $mm^3$, Bonferroni adjusted p=0.0074). Left flank tumor growth data suggest that $CD4^+$ and $CD8^+$ T-cells significantly affect tumor growth control of the metastatic distant tumors. Furthermore, survival between the aforementioned 4 treatment groups was significant different (Log-rank test p=0.0003). Both $CD4^+$ and $CD8^+$ depleted in situ MBTA treated mice demonstrated no significant improvement in survival over saline treated control mice (median survival±SEM of $CD4^+$ depleted in situ MBTA versus saline treated mice: 21±3.2 versus 17±0.9 days, Tukey-Kramer adjusted p>0.05; CD8+ depleted in situ MBTA versus saline treated mice: 17±0.6 versus 17±0.9 days, Tukey-Kramer adjusted p>0.05), as shown in FIG. 2J. The non-T-cell depleted in situ MBTA treated mice demonstrated a significant improvement in survival over the saline treated control mice (median survival±SEM of non-T-cell depleted in situ MBTA treated mice versus saline treated mice: 28±2.4 versus 17±0.9, Tukey-Kramer adjusted p=0.0002). Therefore, MBTA's therapeutic efficacy at the distal tumors is dependent on T-cells.

When compared to the median survival of in situ MBTA injected mice in FIG. 2F, mice in the non-T-cell depleted in situ MBTA injected treatment group had a decreased median survival time (median survival±SEM of in situ MBTA injected mice in FIG. 2F versus non-T-cell depleted in situ MBTA injected mice: 67±11.7 versus 28±2.4 days in FIG. 2J). The difference in survival time can be attributed to the experimental design of each experiment: Animals in FIG. 2F were subcutaneously inoculated with 2.5×10^5 CT26 tumor cells in the left flank to establish a distant (representative metastatic) tumor, while animals in this experiment were inoculated with 5.0×10^5 CT26 tumor cells. At the start of treatment, animals in this section had developed significantly larger left flank distal tumors compared to those in FIG. 2F and therefore reached the study end point substantially faster. Nevertheless, despite the aforementioned differences in the number of CT26 cells used to establish left flank tumors, both experiments independently confirmed that the in situ treatment with MBTA into the primary tumor significantly reduced the tumor growth of the metastatic distant tumors and improved the median survival of the MBTA treated mice when compared to the control.

Example 3: Immunophenotyping (I.P.) of Tumors with Flow Cytometry

Provided herein are methods for I.P. of tumors flow cytometry.

CT26 tumors were established as in Example 1 to the right and left flanks. Two independent sets of I.P. experiments were completed after 10 and 16 days from the start of treatment. Each I.P. experiment consisted of control (n=5) and MBTA treated mice (n=5). After the mice were sacrificed, both right and left flank tumors were excised and subjected to mechanical disruption using a GentleMACS Dissociator (Miltenyi Biotec) in the presence of enzymatic digestion using Tumor Dissociation Kit (Miltenyi Biotec).

Antibodies for flow cytometry staining are listed in TABLE 2.

TABLE 2

Antibodies used in flow cytometry analysis

| Antibodies Experiments | Target | Fluorochrome | Clone | Source |
|---|---|---|---|---|
| Innate immune cell analysis | CD45.2 | APC/ Cyanine7 | 104 | BioLegend, USA, cat. no. 109824 |
| Innate immune cell analysis | CD11c | APC | HL3 | BD Biosciences, USA, cat. no. 550261 |
| Innate immune cell analysis | I-A/I-E (MHC II) | Brilliant Violet 711 ™ | M5/ 114.15.2 | BioLegend, USA, cat. no. 107643 |
| Innate immune cell analysis | CD11b | PE | M1/70 | BioLegend, USA, cat. no. 101208 |
| Innate immune cell analysis | Ly-6G | PE/Cy7 | 1A8 | BioLegend, USA, cat. no. 127618 |

TABLE 2-continued

Antibodies used in flow cytometry analysis

| Antibodies Experiments | Target | Fluorochrome | Clone | Source |
|---|---|---|---|---|
| Innate immune cell analysis | Ly-6C | BV421 | AL-21 | BD Biosciences, USA, cat. no. 562727 |
| Innate immune cell analysis | CD206 (MMR) | FITC | C068C2 | BioLegend, USA, cat. no. 141704 |
| Innate immune cell analysis | live/dead | Propidium Iodide | n/a | BioLegend, USA, cat. no. 421301 |
| Adaptive immune cell analysis | CD45.2 | PE | 104 | BioLegend, USA, cat. no. 109808 |
| Adaptive immune cell analysis | TCR β chain | PE/Cy7 | H57-597 | BioLegend, USA, cat. no. 109222 |
| Adaptive immune cell analysis | CD4 | APC/ Cyanine7 | GK1.5 | BioLegend, USA, cat. no. 100414 |
| Adaptive immune cell analysis | CD8a | Brilliant Violet 711 ™ | 53-6.7 | BioLegend, USA, cat. no. 100759 |
| Adaptive immune cell analysis | CD19 | APC | 1D3/ CD19 | BioLegend, USA, cat. no. 152409 |
| Adaptive immune cell analysis | live/dead | Propidium Iodide | n/a | BioLegend, USA, cat. no. 421301 |
| Cytokine analysis | CD45 | Brilliant Violet 785 ™ | 30-F11 | BioLegend, USA, cat. no. 103149 |
| Cytokine analysis | CD4 | Alexa Fluor ® 647 | RM4-5 | BioLegend, USA, cat. no. 100530 |
| Cytokine analysis | CD8a | BUV737 | 53-6.7 | BD Biosciences, USA, cat. no. 564297 |
| Cytokine analysis | IFNγ | Brilliant Violet 605 ™ | XMG1.2 | BioLegend, USA, cat. no. 505839 |
| Cytokine analysis | Granzyme B | FITC | QA16A02 | BioLegend, USA, cat. no. 372206 |
| Cytokine analysis | TNFα | Brilliant Violet 510 ™ | MP6-XT22 | BioLegend, USA, cat. no. 506339 |
| Cytokine analysis | LIVE/DEAD Fixable Near-IR | LIVE/ DEAD Fixable Near-IR | n/a | Thermo-Fisher Scientific, L10119 |
| Tetramer analysis | CD45 | Brilliant Violet 785TM | 30-F11 | BioLegend, USA, cat. no. 103149 |
| Tetramer analysis | CD4 | Alexa Fluor ® 647 | RM4-5 | BioLegend, USA, cat. no. 100530 |
| Tetramer analysis | CD8a | BUV737 | 53-6.7 | BD Biosciences, USA, cat. no. 564297 |
| Tetramer analysis | H-2L(d) MuLV gp70 env AH1423-431 (SPSYVYHQF) tetramer | PE | n/a | NIH Tetramer Core Facility at Emory University |

TABLE 2-continued

| Antibodies used in flow cytometry analysis | | | | |
|---|---|---|---|---|
| Antibodies Experiments | Target | Fluoro-chrome | Clone | Source |
| Tetramer analysis | live/dead | DAPI | n/a | BD Biosciences, USA, cat. no. 564907 |

Gating strategy used for I.P. analyses of tumors was performed. Specific immune cell populations were defined as follows: Dendritic cells (CD45.2+CD11c+MHCII+); Macrophages (CD45.2+CD11c−CD11b+Ly6G− Ly6C−/low); Monocytes (CD45.2+CD11c− CD11b+Ly6G− Ly6C high); MHC class II+Monocytes (CD45.2+CD11c−CD11b+Ly6G−Ly6C high MHCII+); Neutrophils (CD45.2+CD11c−CD11b+Ly6G+); CD4+ T-cells (CD45.2+ TCRβ+CD4+CD8−); CD8+ T-cell (CD45.2+ TCRβ+CD4-CD8+); B cells (CD45.2+ TCRβ−CD19+). Intracellular cytokine staining and flow cytometry—Suspensions containing T-cells were stained with a fixable live/dead stain (Invitrogen) in PBS followed by surface antibody staining in FACS buffer (PBS with 0.5% BSA and 0.1% sodium azide). For intracellular staining, cells were first stimulated with Cell Stimulation Cocktail (eBioscience) containing PMA/Ionomycin and protein transport inhibitor for five hours prior to undergoing staining. Next, cells were stained for surface molecules following fixation and permeabilization (eBioscience), and then stained with cytokine antibodies. Stained cells were analyzed by flow cytometry (LSRII; BD Bioscience). Data analysis was performed using FlowJo software (TreeStar).

Example 4: Enhanced Subject-Specific Innate Immunity Against CT26 Tumors after MBTA Treatment Provided herein are methods for using MBTA treatment to treat CT26 tumors with innate immunity.

Immunophenotyping (I.P.) of tumors were performed according to Example 3 to further assess the immune profile of the tumor microenvironment of subcutaneous tumor model in Example 1. Both right and left flank tumors were harvested 10 days and 16 days after the start of the MBTA treatment.

Figure 3A:
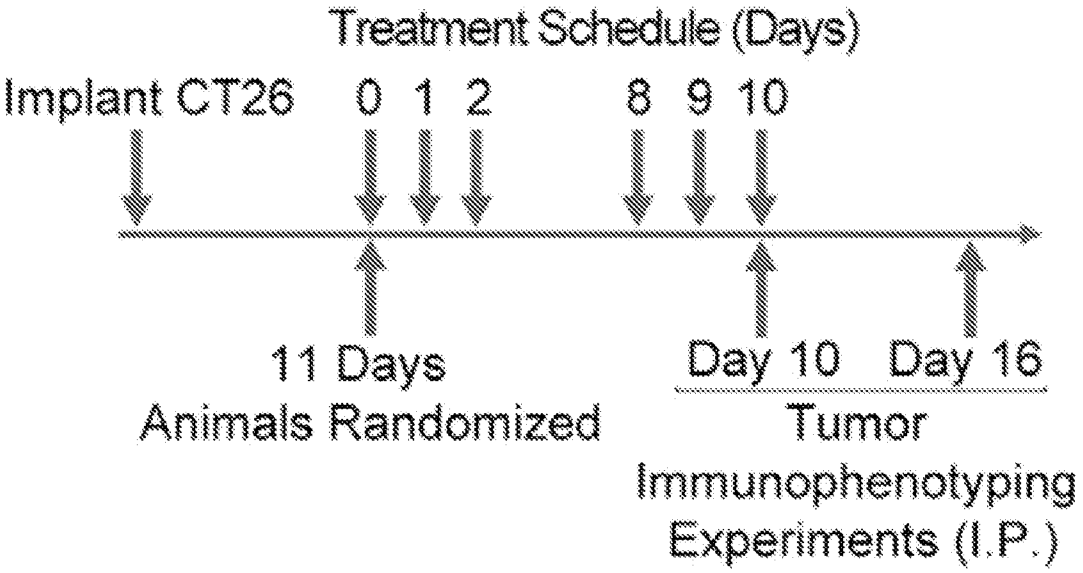
FIGS. 3A-I show that MBTA stimulates the innate immune system to elicit subject-specific rejection of primary and distant CT26 tumors.

To elucidate temporal changes in immune cell populations, I.P. analyses were completed at two distinct time points, as shown in FIG. 3A. The first timepoint was carried out 10 days after first treatment and within 6 hours following in situ injection of MBTA. To provide insight into the acute changes of immune cell populations immediately following treatment, day 10 was chosen to coincide with the final injection of the second set of treatments. The second time point was carried out 6 days later, on day 16, to assess interim changes in the immune cell composition.

Figure 3B:
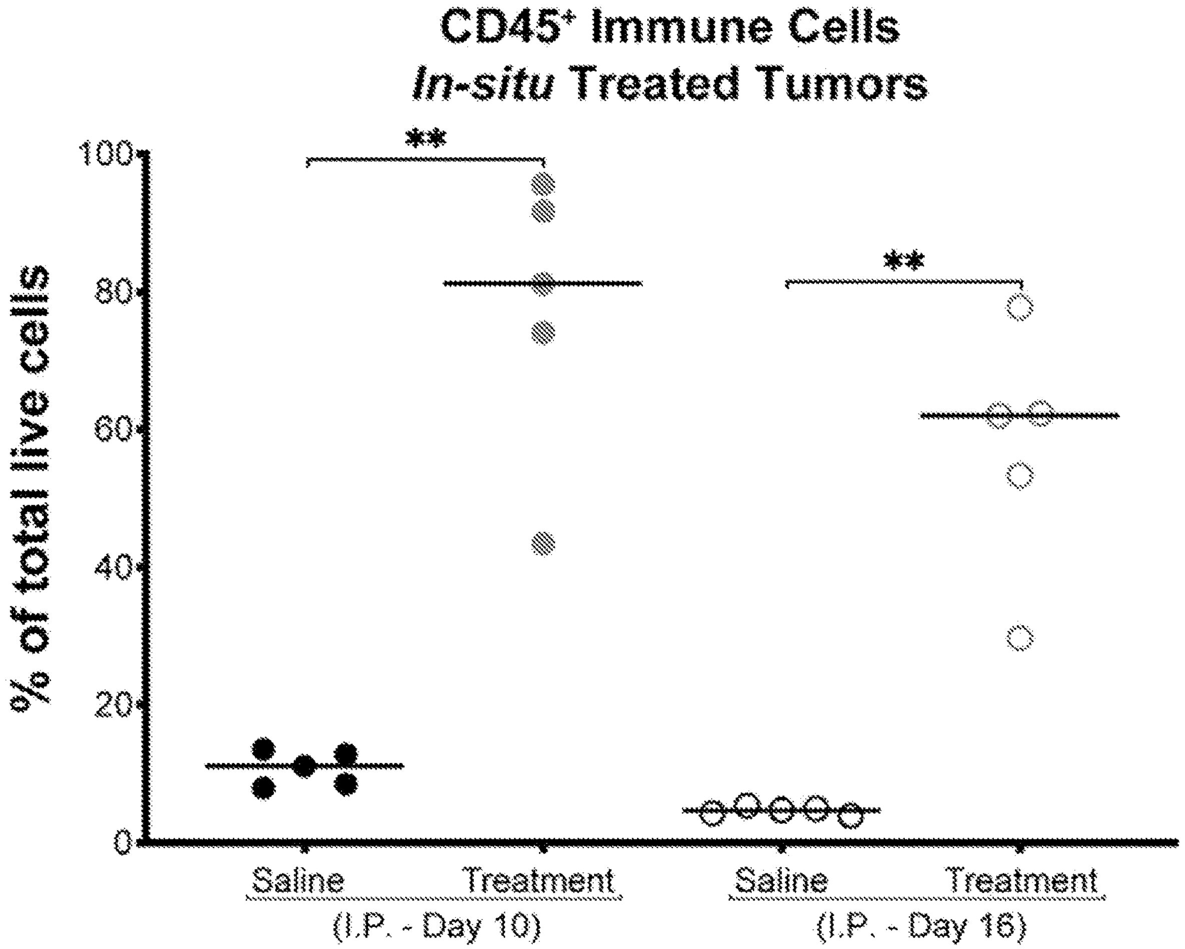
Figure 3C:
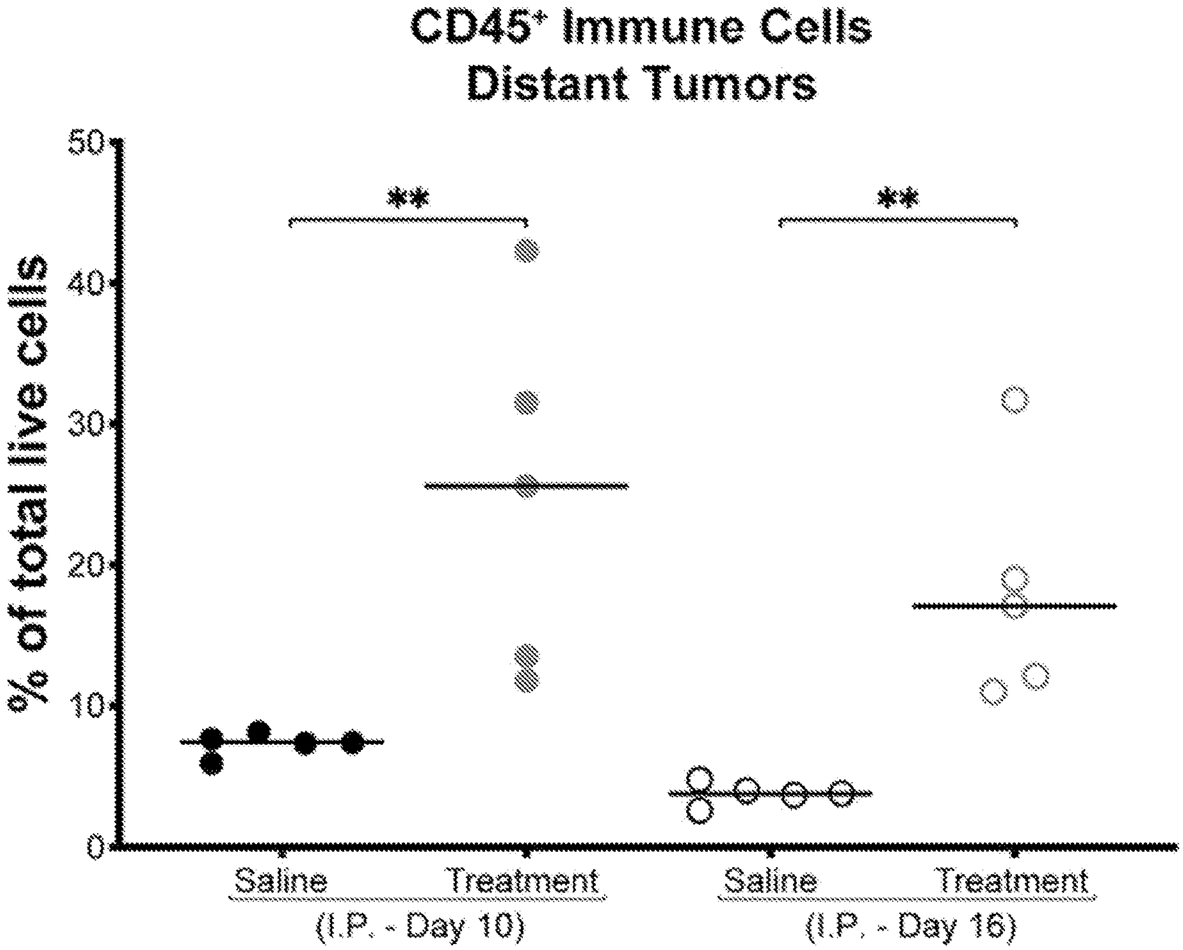
Figure 3D:
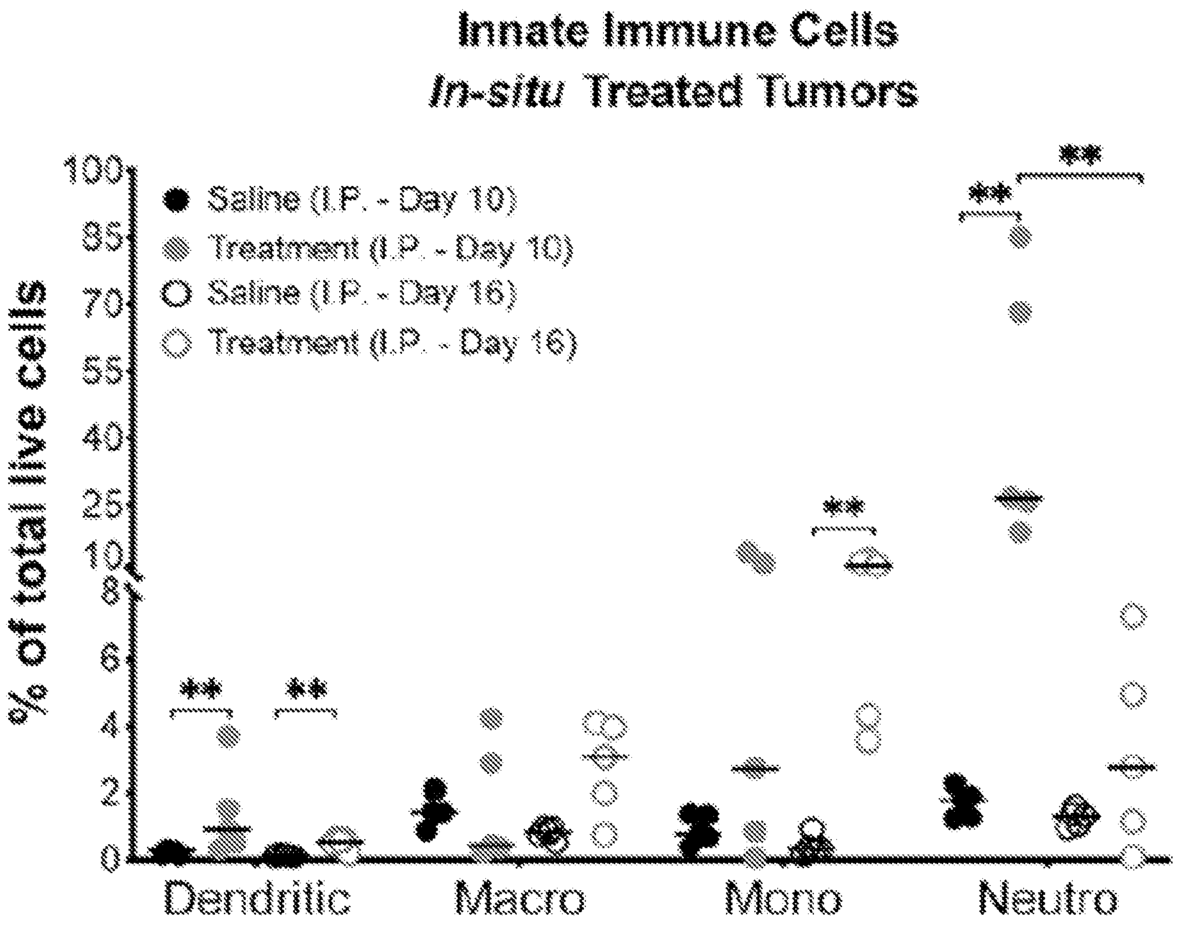
Figure 3E:
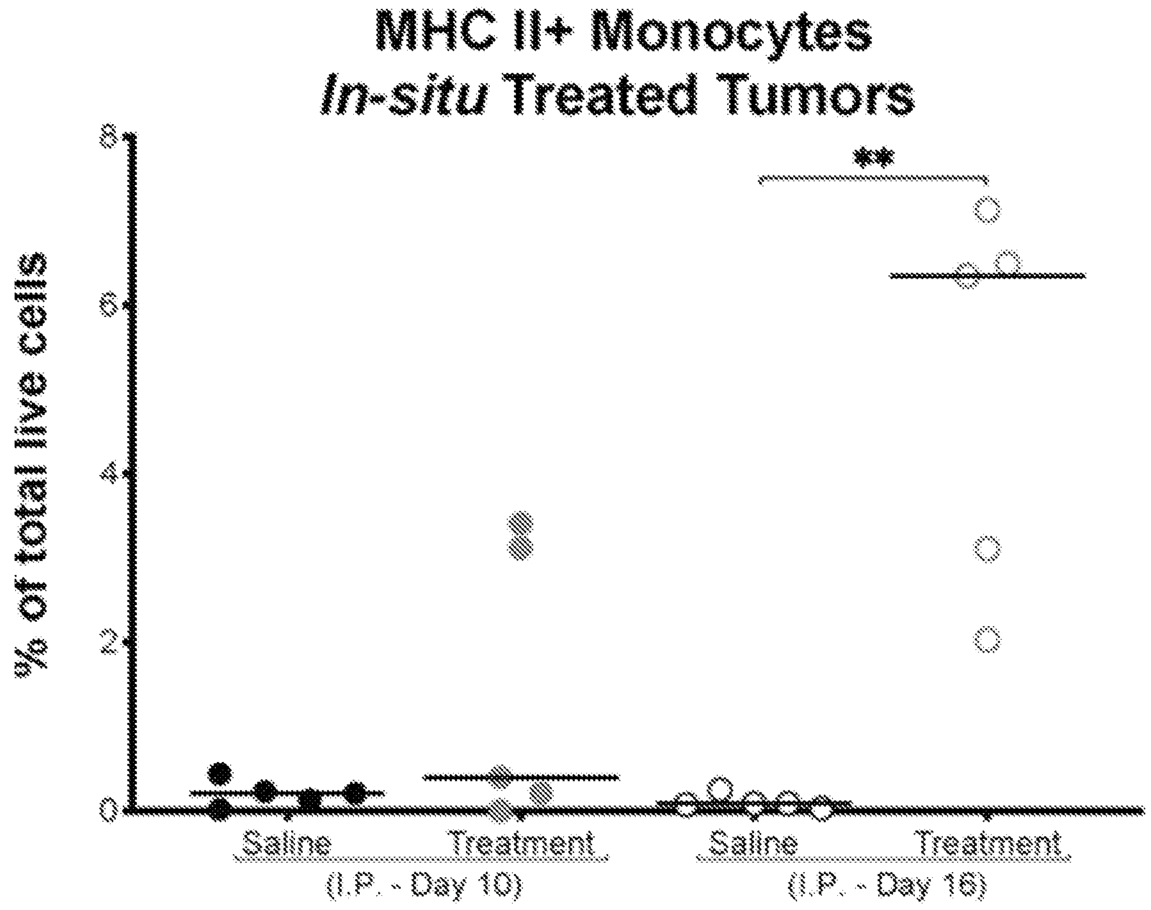

In situ injection of the MBTA into the primary tumors significantly increased the infiltration of immune cells (CD45+ cells) into both primary and metastatic distant tumors of the MBTA treated mice, compared to the saline treated control mice, as shown in FIGS. 3B and 3C. FIG. 3D revealed a striking dendritic (CD45.2+CD11c+MHCII+) and neutrophilic (CD45.2+CD11c−CD11b+Ly6G+) inflammatory response in the MBTA treated mice versus the control. Six days later, results from I.P. (Day 16) analysis of the right flank tumors revealed a significant decrease in neutrophils and increase in APCs, including DCs and MHC class II positive monocytes (CD45.2+CD11c−CD11b+Ly6G−Ly6C high MHC II+), as shown in FIGS. 3D and 3E.

Figure 3F:
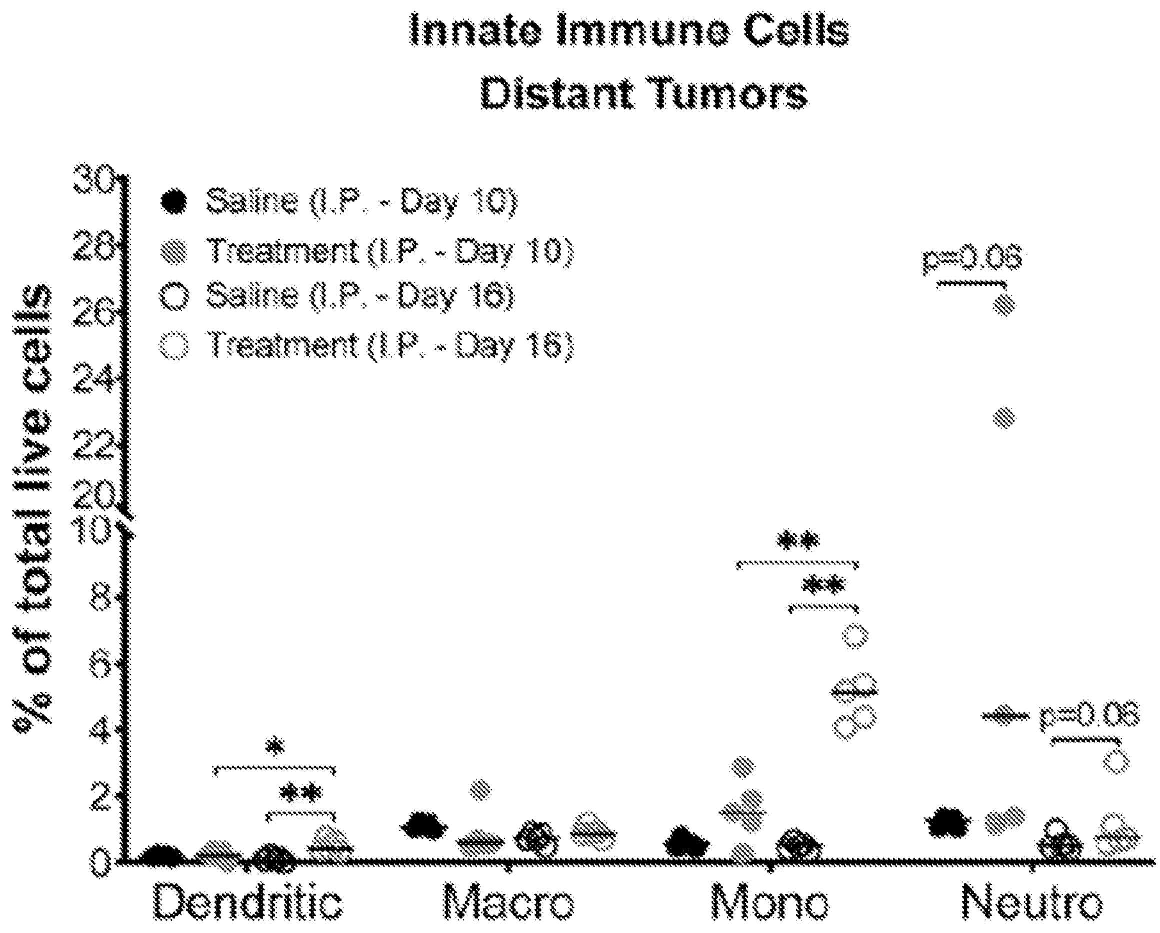
Figure 3G:
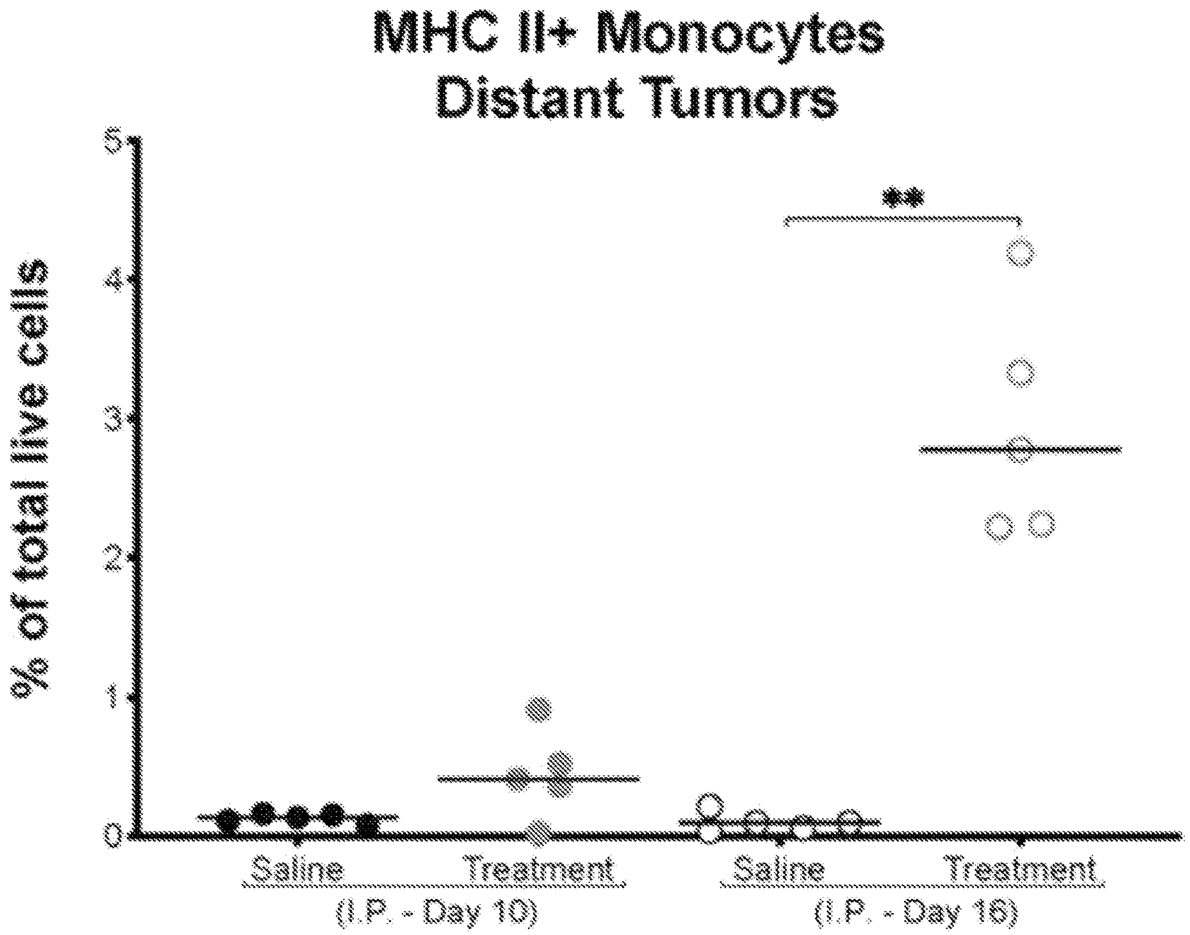
Figure 3H:
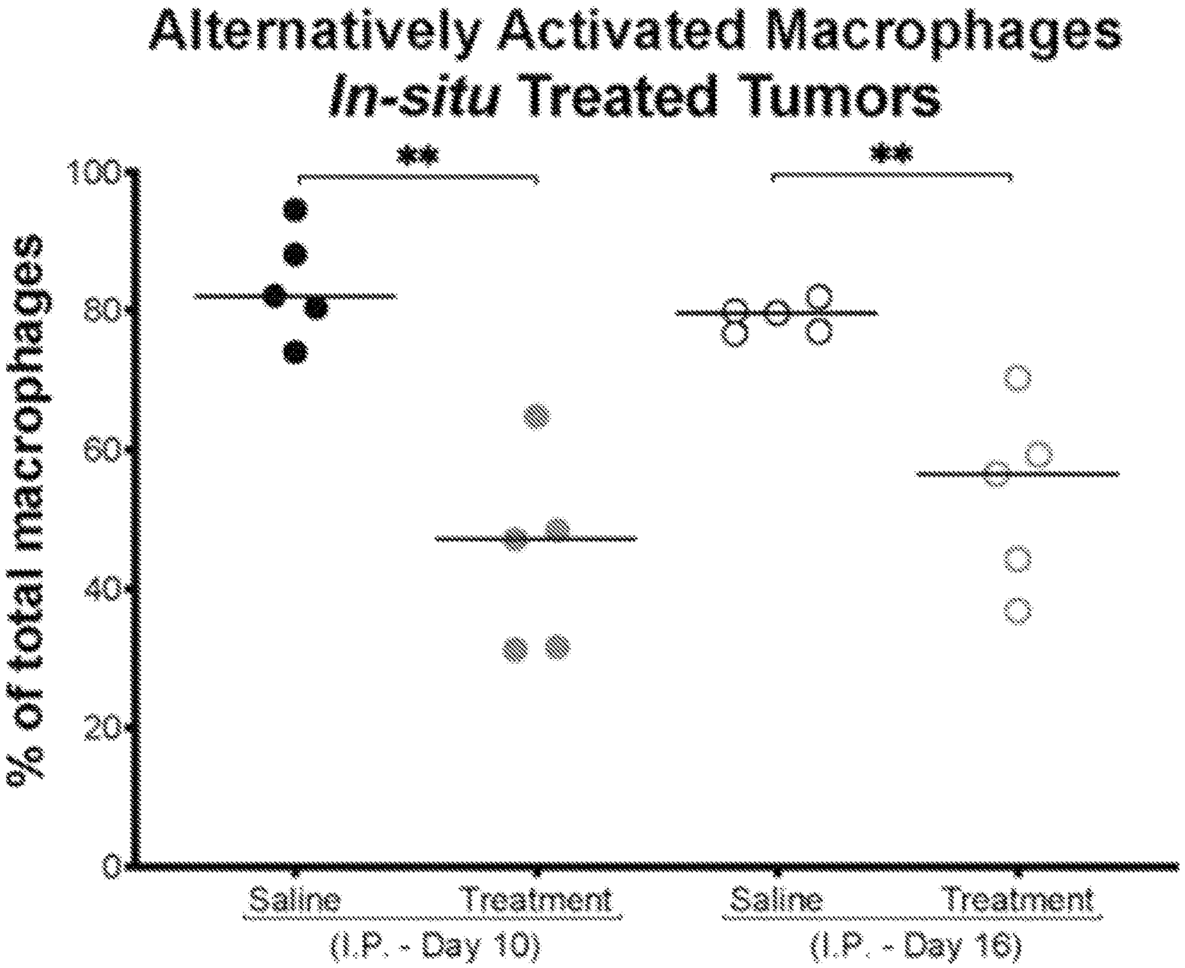
Figure 3I:
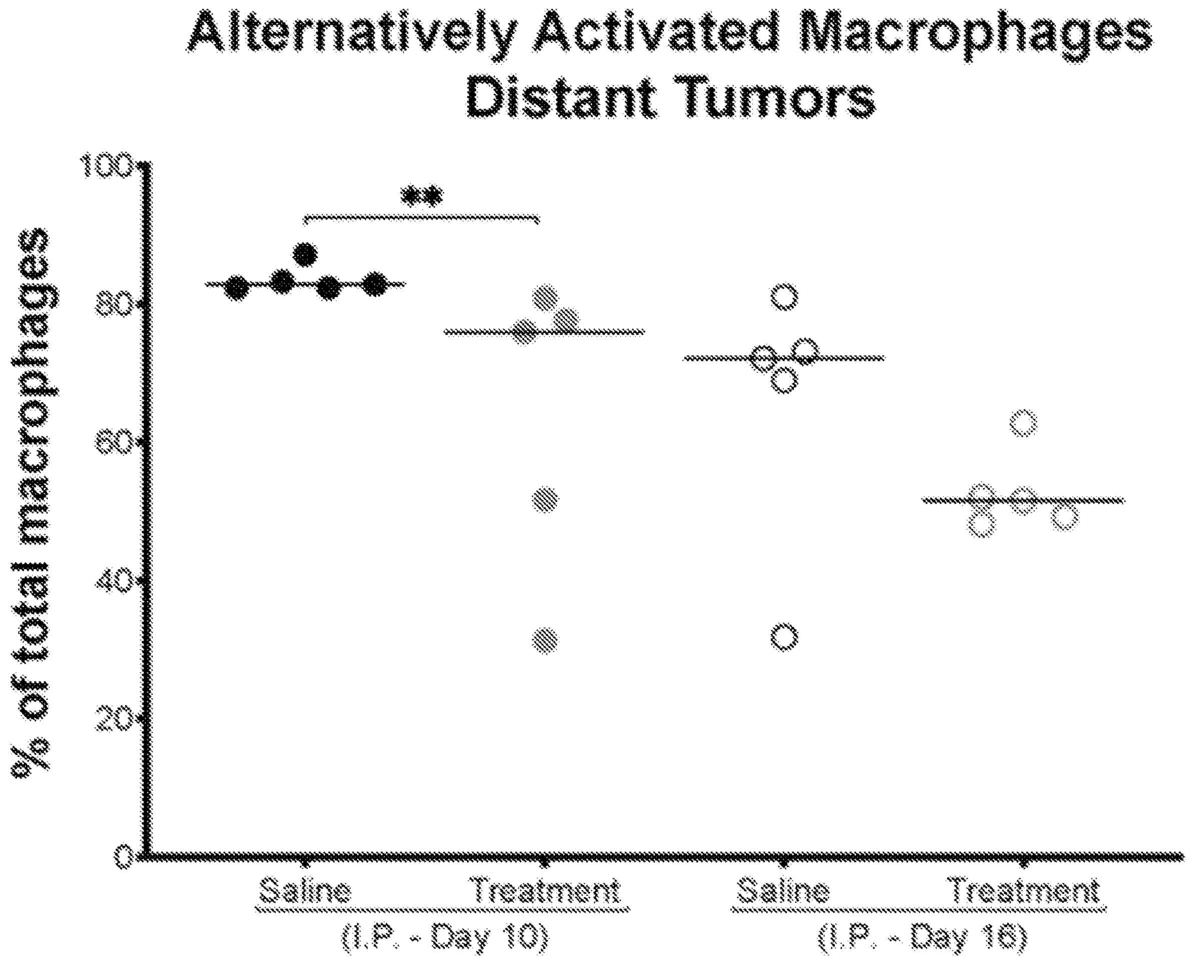

Assessments of the innate immune cell populations at the distal, non-treated left flank tumors showed an increased neutrophilic immune response on I.P. (Day 10), followed by a significant increase in APCs (DCs and MHC class II positive monocytes) on I.P. (Day 16) in the tumors of the MBTA treated mice versus the control, as shown in FIGS. 3F and 3G. These results suggest MBTA therapy facilitates neutrophil and APC trafficking to tumors, thereby promoting phagocytosis of tumor cells and processing for the further development of subject-specific adaptive immune responses. Although FIGS. 3D and 3F show that there were no significant changes in the overall quantity of macrophages (CD45.2+CD11c−CD11b+Ly6GLy6C−/low), an assessment of the CD206 positive alternatively activated macrophage (AAM) population—also known as M2-macrophages (CD45.2+CD11c−CD11b+Ly6GLy6C−/low CD206+), as shown in FIG. 3H—demonstrated that the AAM population was significantly decreased in the primary (MBTA treated) tumors on both I.P. day 10 and 16. FIG. 3I shows that the AAM population in the distal tumors from the MBTA treated mice significantly decreased on I.P. day 10. TLR agonist and anti-CD40-mAb were shown to skew the polarization of tumor associated macrophages (TAM) toward an M1-like phenotype.

Example 5: Enhanced Subject-Specific Adaptive Immune Response Against CT26 Tumors after MBTA Treatment Provided herein are methods for using MBTA treatment to treat CT26 tumors with adaptive immune response.

Figure 4A:
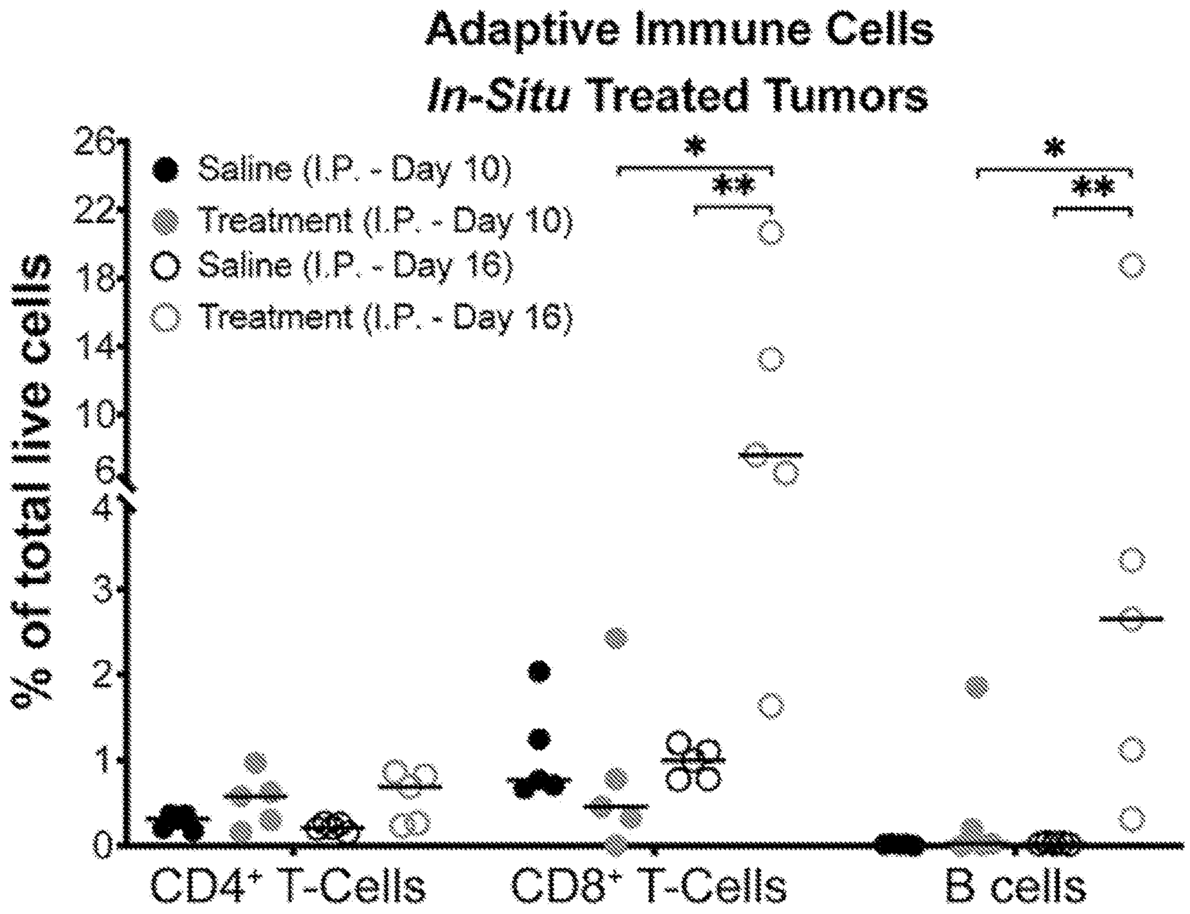
FIGS. 4A-F show that MBTA stimulates the adaptive immune systems to elicit subject-specific rejection of primary and distant CT26 tumors.
Figure 4B:
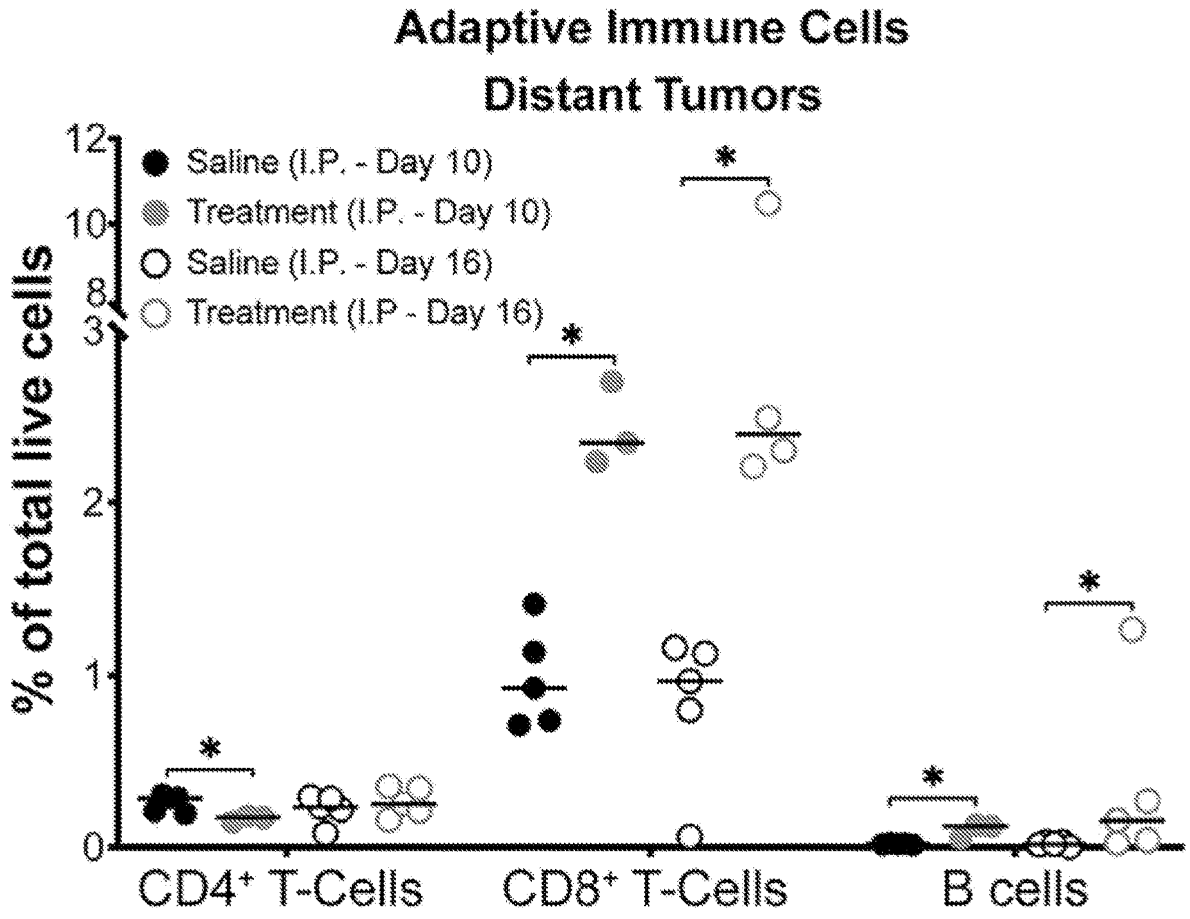

Results from I.P. day 10 and 16, as described in Example 4, also revealed an overall increase in adaptive immune cells in both primary and distant tumors of the MBTA treated mice compared to the control, as shown in FIGS. 4A and 4B. FIG. 4A shows that CD8+ T-cells (CD45.2+ TCRβ+CD4−CD8+) and B cells (CD45.2+ TCRβ−CD19+) populations statistically increased in the primary tumor of the MBTA treated mice demonstrated on I.P. day 16. I.P. (Day 10) and I.P. (Day 16) analyses revealed that both CD8+ T-cell and B cell populations significantly increased in the tumor of the MBTA treated mice compared to the control, as shown in FIG. 4B. These results suggest that in situ injection of MBTA at the primary tumor augments the overall quantity of the adaptive immune cells to the distal, non-treated tumors, underscoring MBTA's therapeutic potential to modulate the T-cell inflammatory response at representative metastatic lesions.

Figure 4C:
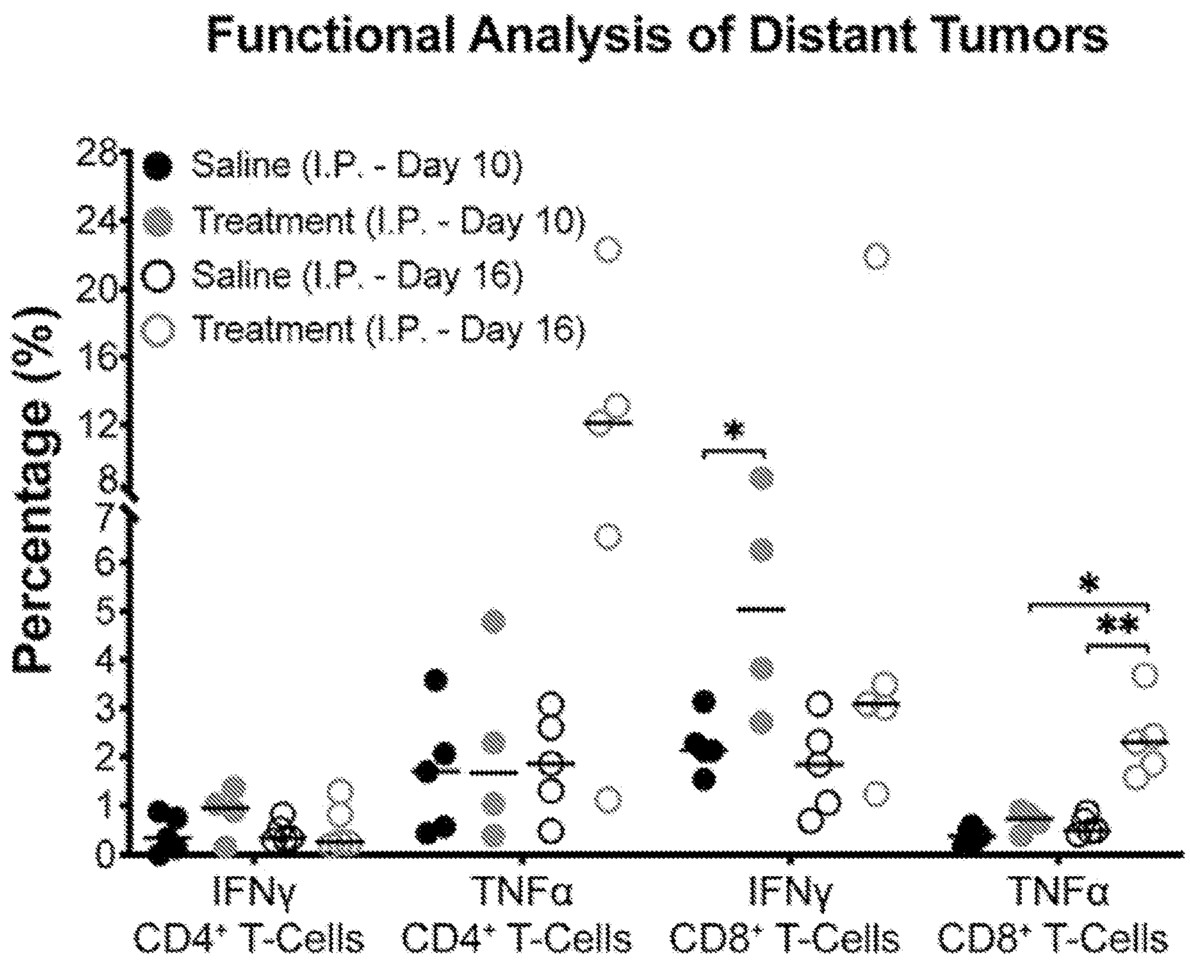
Figure 4D:
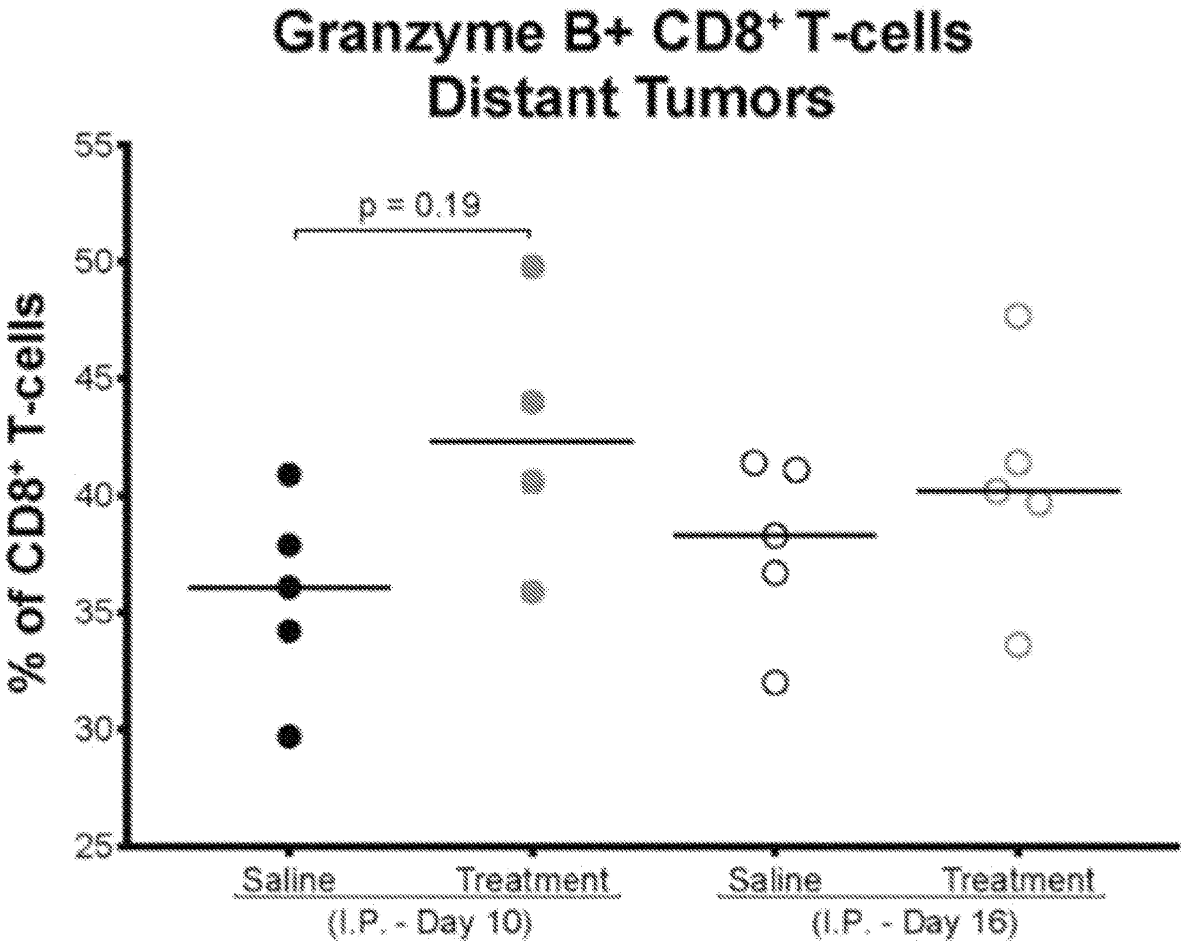
Figure 4E:
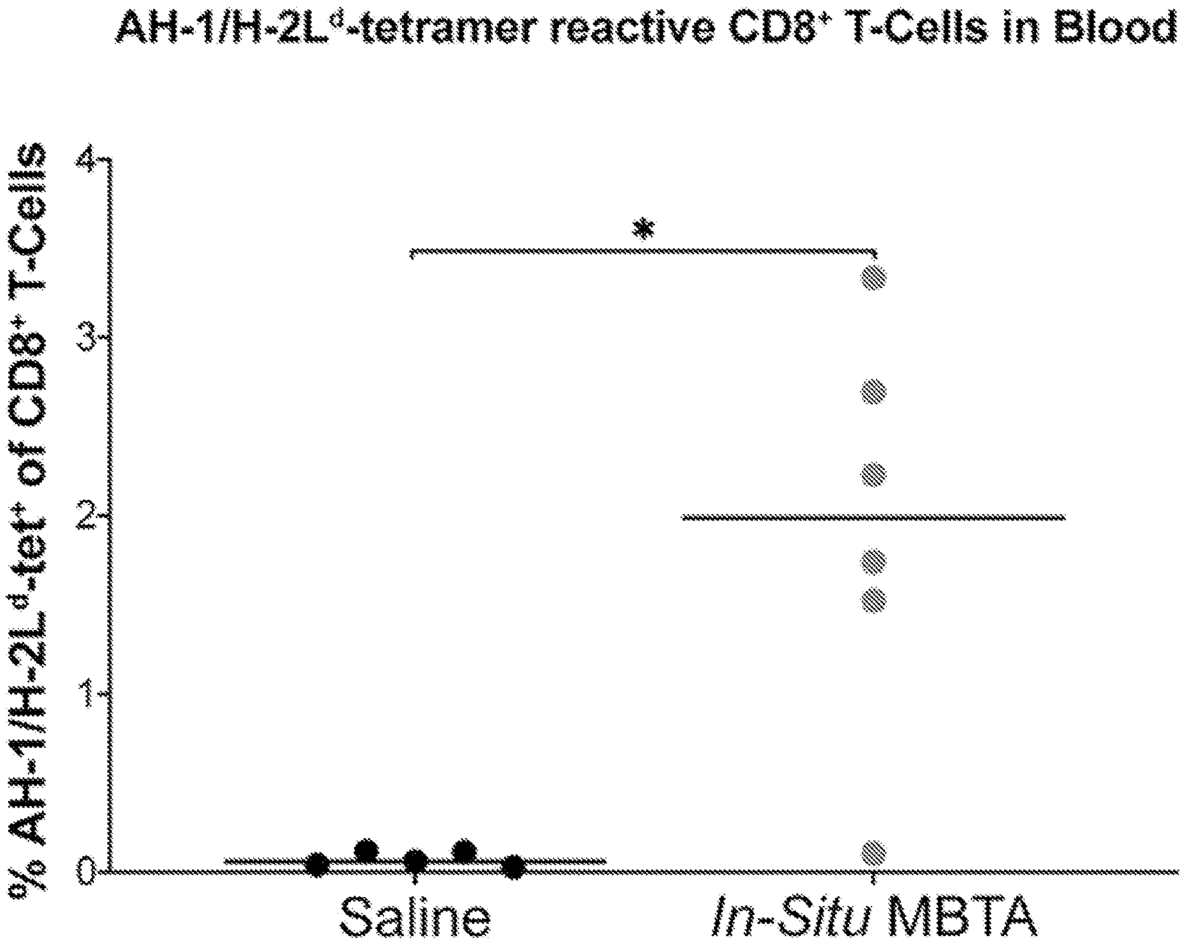
Figure 4F:
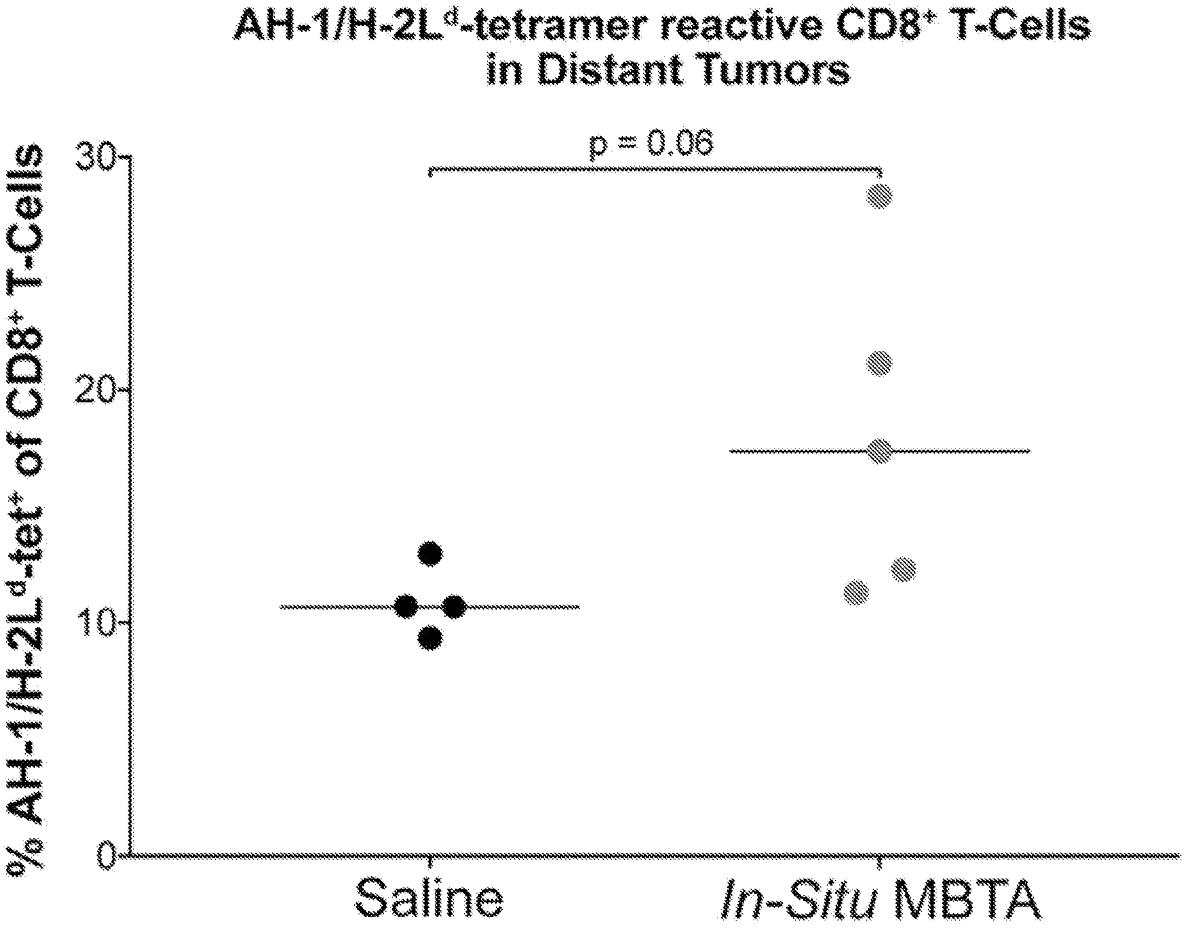

$CD4^+$ (CD45.2+ TCRβ+CD4+CD8−) and $CD8^+$ T-cell populations were extracted from the distant tumors and stimulated with PMA/Ionomycin in vitro to assess for intracellular expression of IFNγ, TNFα and Granzyme B. T-cells harvested from the MBTA treated mice on I.P. (Day 10) and (Day 16) had higher production of IFNγ and TNFα than the control, as shown in FIG. 4C. Notably, CD8+ T-cells demonstrated a significant increase in IFNγ on I.P. (Day 10) and TNFα during the six-day interval between I.P. (Day 10) and (Day 16). FIG. 4D also shows an increased, though not statistically significant, population of Granzyme B positive CD8+ T cells. Hence, the MBTA treatment significantly augments the quantity and activation of CD8+ T-cells within the distant tumors, suggesting their major role in the MBTA-induced tumor growth inhibition. AH-1 loaded H-2Ld tetramer was used to assess if the MBTA therapy generated higher quantities of CD8+ T-cells (CTLs) against the immunodominant epitope of CT26, gp70423-431 (AH-1) (Huang, et al., Proc. Natl. Acad. Sci. U.S.A 1996, 93, 9730). Peripheral blood samples and the distant tumor of the in situ MBTA treated and control mice were collected 11 days after the start of treatment for analysis. As shown in FIG. 4E, the in situ MBTA treated mice had a significantly higher percentage of AH-1/H-2Ld-specific CD8+ T-cells in the whole blood relative to the control (p=0.02 by Mann-Whitney U test). The in situ MBTA treated mice also had increased AH-1/H-2Ld-specific CD8+ T-cells within the distant tumor relative to the control (p=0.06 by Mann-Whitney U test), as shown in FIG. 4F. Therefore, the in situ MBTA injections increase the AH-1-specific CD8+ T-cell clones circulating in the blood and in the metastatic distant tumors within 11 days from the start of MBTA treatment.

Taken together, the in situ injection of MBTA resulted in significant changes in the immunophenotypes of representative primary and metastatic tumors. At the primary tumor, the MBTA treatment generated an innate inflammatory response initially characterized by a strong neutrophilic and DC predominance and followed by a significant increase in APC populations (MHC II+ monocytes and DCs). At the metastatic distant tumor, the MBTA treatment strengthened the adaptive immune response by increasing the overall supply of CD8+ T-cells and B cells infiltrating the tumor. T-cells extracted from the distant tumor were not only higher in quantity but demonstrated higher expressions of IFNγ and TNFα cytokines, relative to the control, validating their enhanced tumoricidal activity. Collectively, our finding in situ MBTA treatment elicits tumor rejection of representative metastatic tumors.

Example 6: RCT26-MBTA Vaccines Generate a Potent Subject-Specific Antitumor Immune Response in CT26-Bearing Mice Provided herein are methods for generating a potent antitumor immune response using the rCT26-MBTA vaccine.

Generation of the rCT26-MBTA Vaccine

Figure 5A:
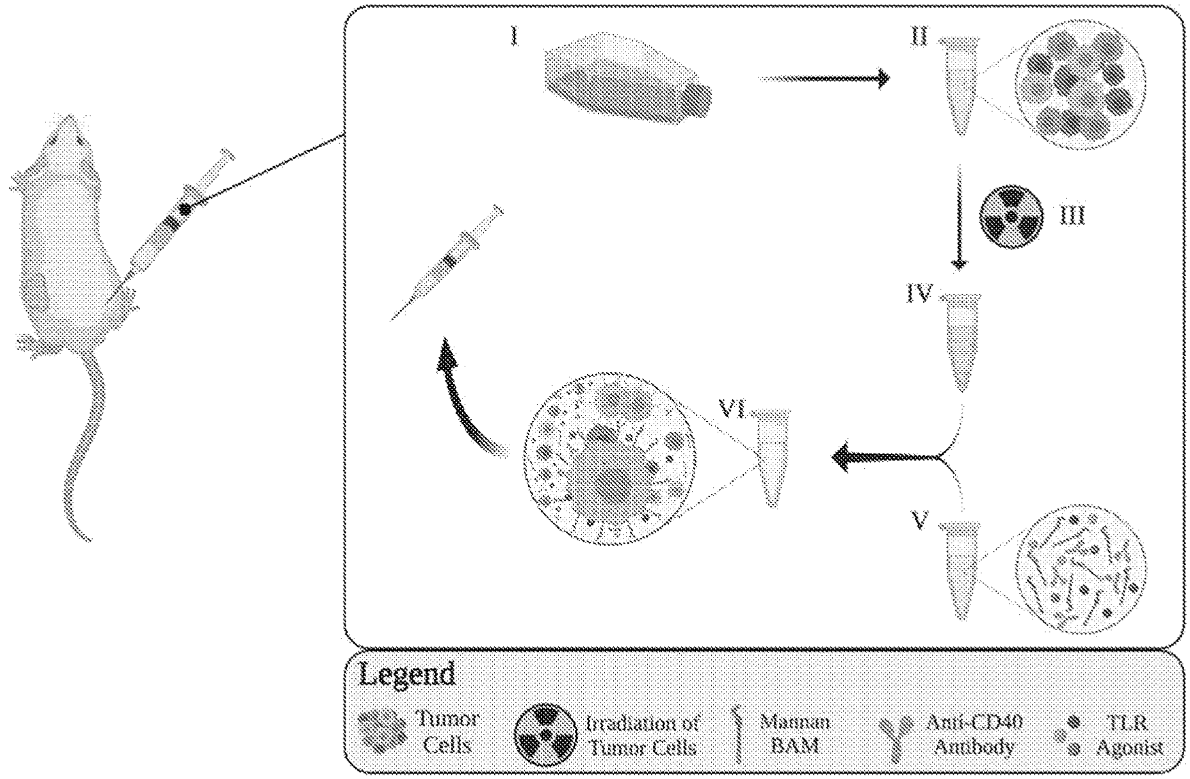
FIGS. 5A-F show that rCT26-MBTA vaccines generate a potent subject-specific antitumor immune response resulting in improved tumor growth control and survival in CT26-bearing mice.
Figure 5B:
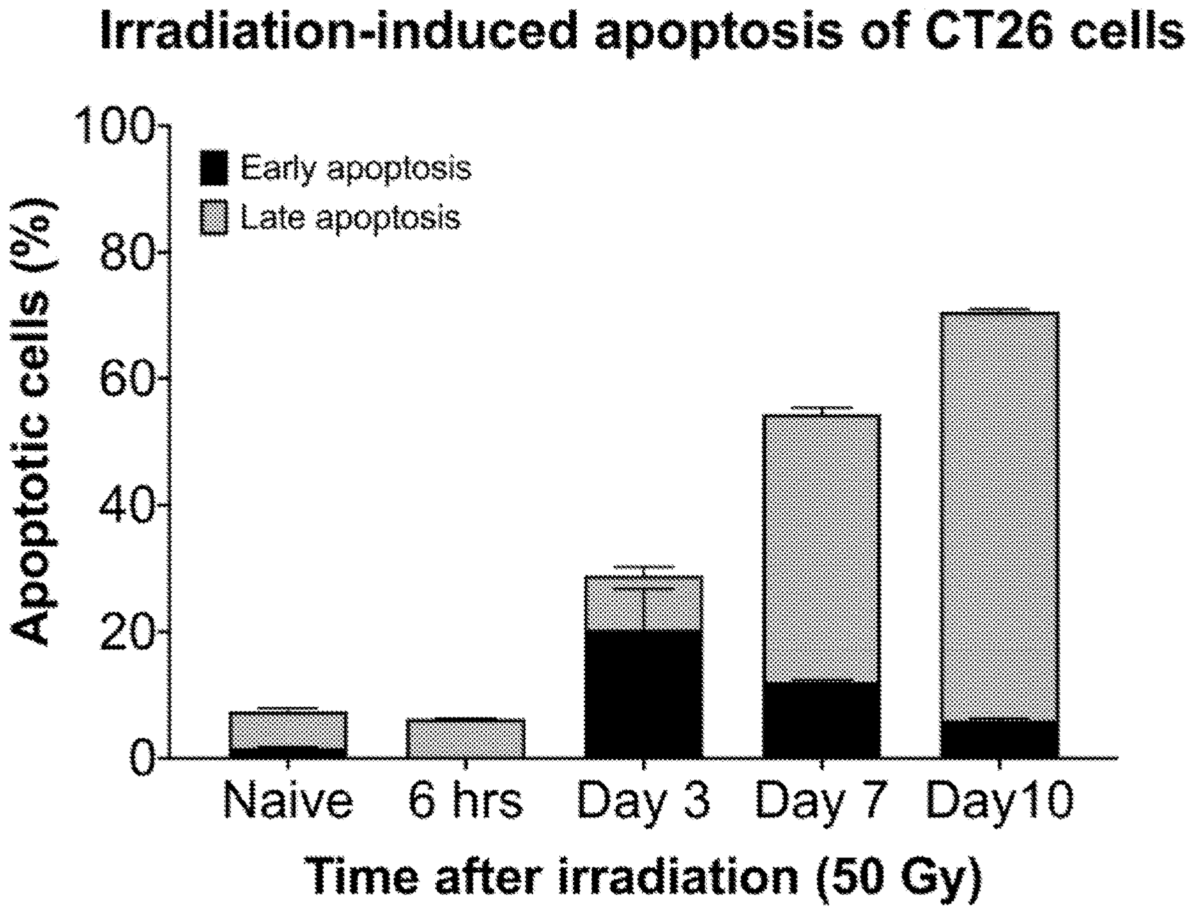

As shown in FIG. 5A, CT26 cells are expanded in vitro and subsequently aliquoted into 1×10^6 million cells per vaccine dose. CT26 cells are sub-lethally irradiated with 50 Gy using a $^{137}$Cs MARK I model irradiator (JL Shepherd & Associates, San Fernando, CA) to induce tumor cell apoptosis and prevent engraftment of tumor cells at the vaccine site. CT26 tumor cells were initially irradiated to induce tumor cell apoptosis and prevent tumor outgrowth when used as a component in the rCT26-MBTA vaccine, as shown in FIG. 5B.

For the rCT26-MBTA vaccines, 100 μL of the following therapeutic mixture were injected subcutaneously into the right flanks of rCT26-MBTA treated mice: a) 1×10^6 irradiated CT26 cells suspended in 50 μL PBS and b) 50 μL of the therapeutic mixture consisting of 0.5 mg R-848 (HCl form), 0.5 mg poly(I:C), 0.5 mg LTA, and 0.4 mg anti-CD40 per mL of 0.2 mM mannan-BAM in PBS. The vaccine dose (a) was then pulsed (incubated) with (b) (50 μL, dose per mouse) for 1 h, facilitating the in vitro integration of mannan-BAM into tumor cell membranes, to form the therapeutic mixture. It was then subsequently injected subcutaneously to the right flank of treated animals according to the specified therapeutic schedule. Mice receiving the rCT26 vaccine were injected with 1×10^6 irradiated tumor cells suspended in 100 μL PBS (dose per mouse).

Generation of a Potent Immune Response Using the rCT26-MBTA Vaccine

The rCT26-MBTA vaccinated mice can generate CD8+ T-cell responses against CT26-specific antigens.

Figure 5C:
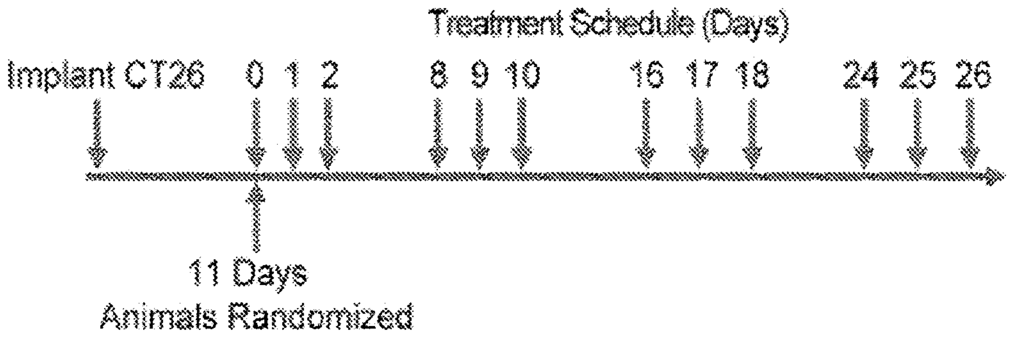

As shown in FIG. 5C, female BALB/c mice were inoculated with CT26 cells subcutaneously at the left flank, using the method described in Example 1. After 11 days, mice were randomized into three treatment groups: normal saline (control; n=7), irradiated CT26 cells (rCT26; n=7) or rCT26 pulsed with MBTA vaccines (rCT26-MBTA; n=8). Treatments were injected subcutaneously into the right flank three consecutive times per week for four weeks (12 dosages). Experiment was performed twice.

Figure 5D:
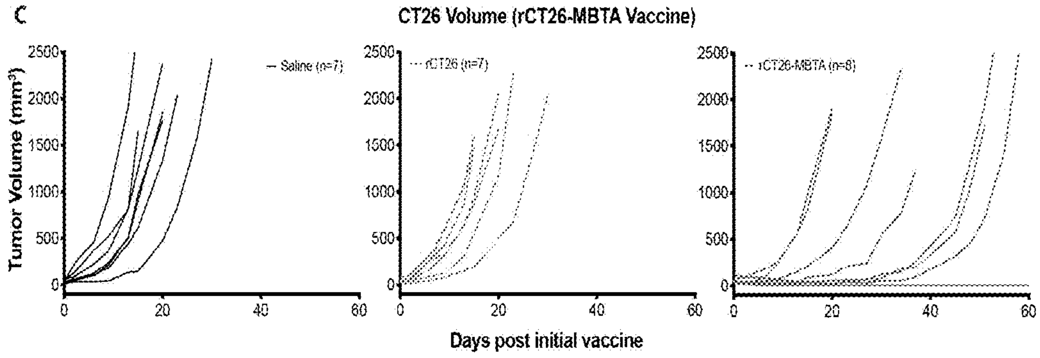

After 6 days of treatment, a Kruskal-Wallis test revealed a statistically significant difference in tumor volumes corresponding to the saline treated control, rCT26 and rCT26-MBTA treated mice (p=0.0108), as shown in FIG. 5D.

Figure 5E:
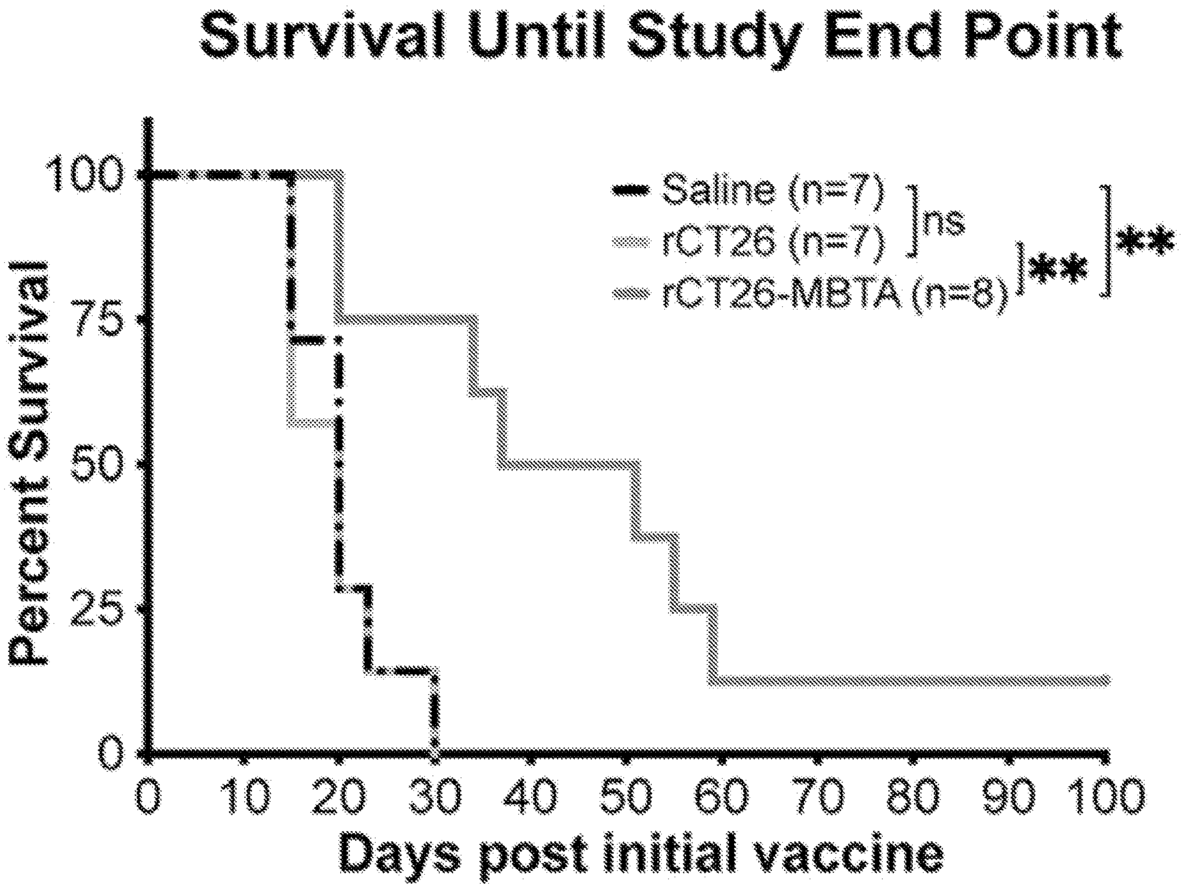
Figure 5F:
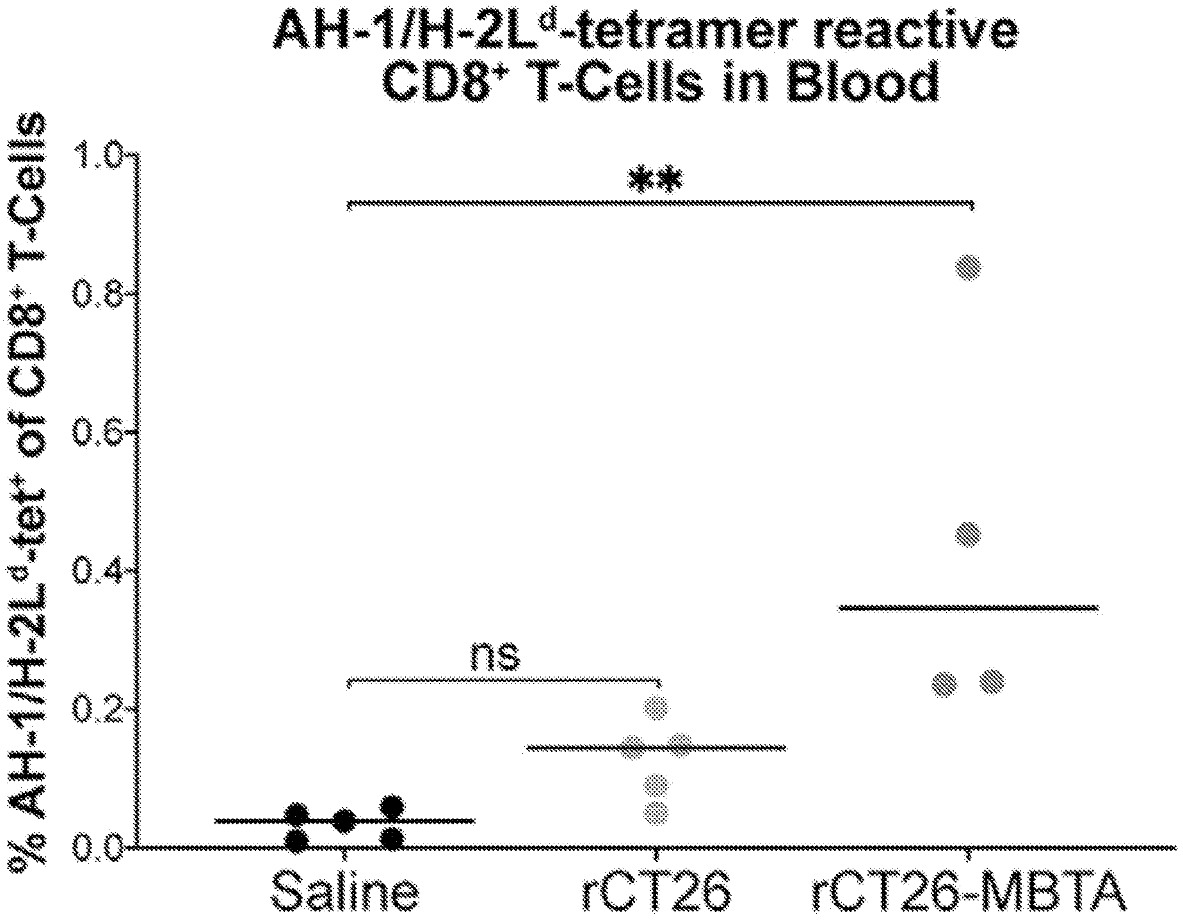
Figure 5G:
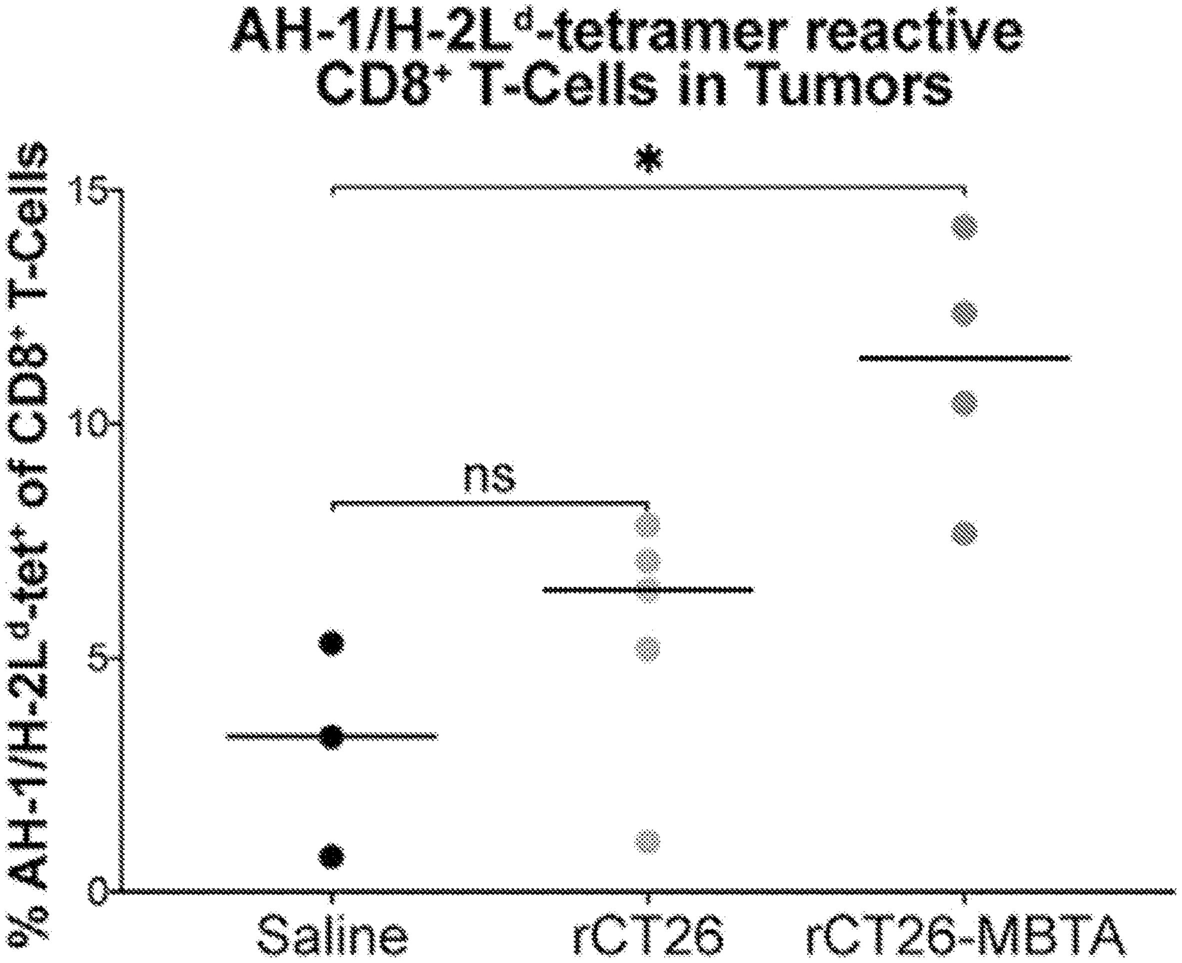
FIG. 5G depicts a dot plot showing the percentage of AH-1-specific $CD8^+$ T-cells extracted from the tumors of the CT26 tumor-bearing mice with saline treatment, rCT26 vaccination, and rCT26-MBTA vaccination. rCT26-MBTA-treated mice had significantly more AH-1-specific (AH-1/H-2Ld-tetramer reactive) $CD8^+$ T-cells in the blood than the saline or rCT26 treated mice did. Data is shown as individual plots with median. *$p<0.05$ by Kruskal-Wallis test.

A post hoc analysis revealed that the rCT26-MBTA vaccinated mice demonstrated significantly smaller median tumor volumes compared to the rCT26 or saline vaccinated mice after 6 and 15 days of treatment, respectively (Day 6: median tumor volumes±SEM of rCT26-MBTA versus rCT26 vaccinated mice—47.7±19.0 versus 247.1±37.3 mm$^3$: Bonferroni adjusted p=0.0279; Day 15: median tumor volumes of rCT26-MBTA versus saline vaccinated mice—67.6±137.7 versus 971.2±320.3 mm$^3$. Bonferroni adjusted p=0.0420). No significant difference in tumor volumes was observed between the rCT26 and saline treatment mice (Bonferroni adjusted p>0.05). Mice in the rCT26-MBTA vaccine treatment group also demonstrated a significant increase in survival when compared to the saline or rCT26 vaccinated mice (median survival±SEM of rCT26-MBTA versus saline treated mice: 44±9.2 versus 20±1.9 days, Tukey-Kramer adjusted p=0.0071; median survival of rCT26-MBTA versus rCT26 vaccinated mice: 44±9.2 versus 20±2.1 days, Tukey-Kramer adjusted p=0.0034), as shown in FIG. 5E, in addition to the improved tumor growth control. In contrast, mice in the rCT26 vaccine treatment group did not have improved survival over the saline treated mice (median survival±SEM of rCT26 versus saline treated mice: 20±2.1 versus 20±1.9 days, Tukey-Kramer adjusted p>0.05). 1/8, or 12.5% of the rCT26-MBTA vaccinated mice achieved CR for the duration of the study, as shown in FIG. 5E. Therefore, the treatment with a total of 12 rCT26-MBTA vaccinations can successfully generate a potent antitumor immune response. We also evaluated the quantities of AH-1/H-2Ld-specific CD8+ T-cells found in the peripheral blood and within distal, nontreated tumors. Peripheral blood samples were collected 10 days after the start of treatment and after receiving a total of two vaccinations. Tumors were harvested 22 days after the start of treatment and after receiving a total of four vaccinations, which is in accordance with the known timeline for T-cell activation after initial antigen stimulation (Pennock et al. Adv. Physiol. Educat. 2013, 37, 273). The rCT26-MBTA vaccine treated mice had significantly more AH-1/H-2Ld-specific CD8+ T-cells in the whole blood than the control mice (p=0.0018 by Kruskal-Wallis test), as shown in FIG. 5F. To examine the presence of AH-1/H-2Ld-specific CD8+ T-cells in tumors, tumor infiltrating lymphocytes were isolated and analyzed by flow cytometry. The rCT26-MBTA vaccinated mice similarly had significantly more AH-1/H-2Ld-specific CD8+ T-cells within the tumors relative to the control (p=0.0169 by Kruskal-Wallis test), as shown in FIG. 5G. The rCT26 vaccinated treated mice also had more AH-1/H-2Ld-specific CD8+ T-cells, although not statistically significant, found in the whole blood and within the tumors when compared to the saline treated mice (p=0.1642 and 0.6469, respectively, by Kruskal-Wallis test). The AH-1-MHC tetramer results suggest that significantly more AH-1-specific CD8+ T-cell clones were found in the whole blood and within the tumors of the rCT26-MBTA vaccinated mice when compared to the control mice, underscoring its potential to generate CD8+ T-cell responses against CT26-specific antigens.

Figure 5H:
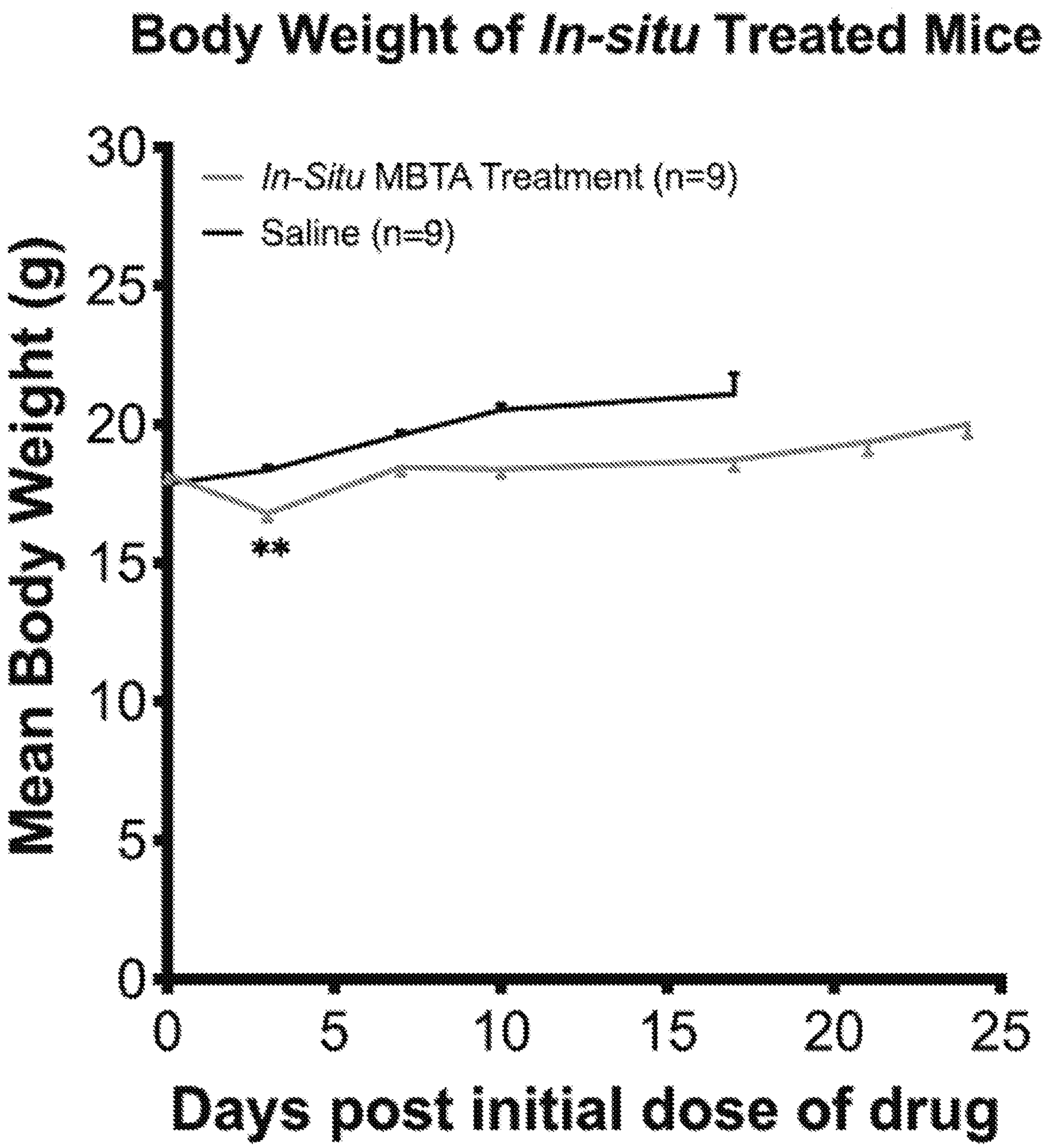
FIG. 5H shows a line plot of the mean body weight (g) of the mice subjected to saline and in situ MBTA treatment. In situ MBTA treated mice demonstrated a significant acute drop in mean body weight 3 days after the start of treatment when compared to pre-treatment levels. The loss in body weight was recuperated 7 days post-treatment. $p=0.004$ by Mann-Whitney U test.
Figure 5I:
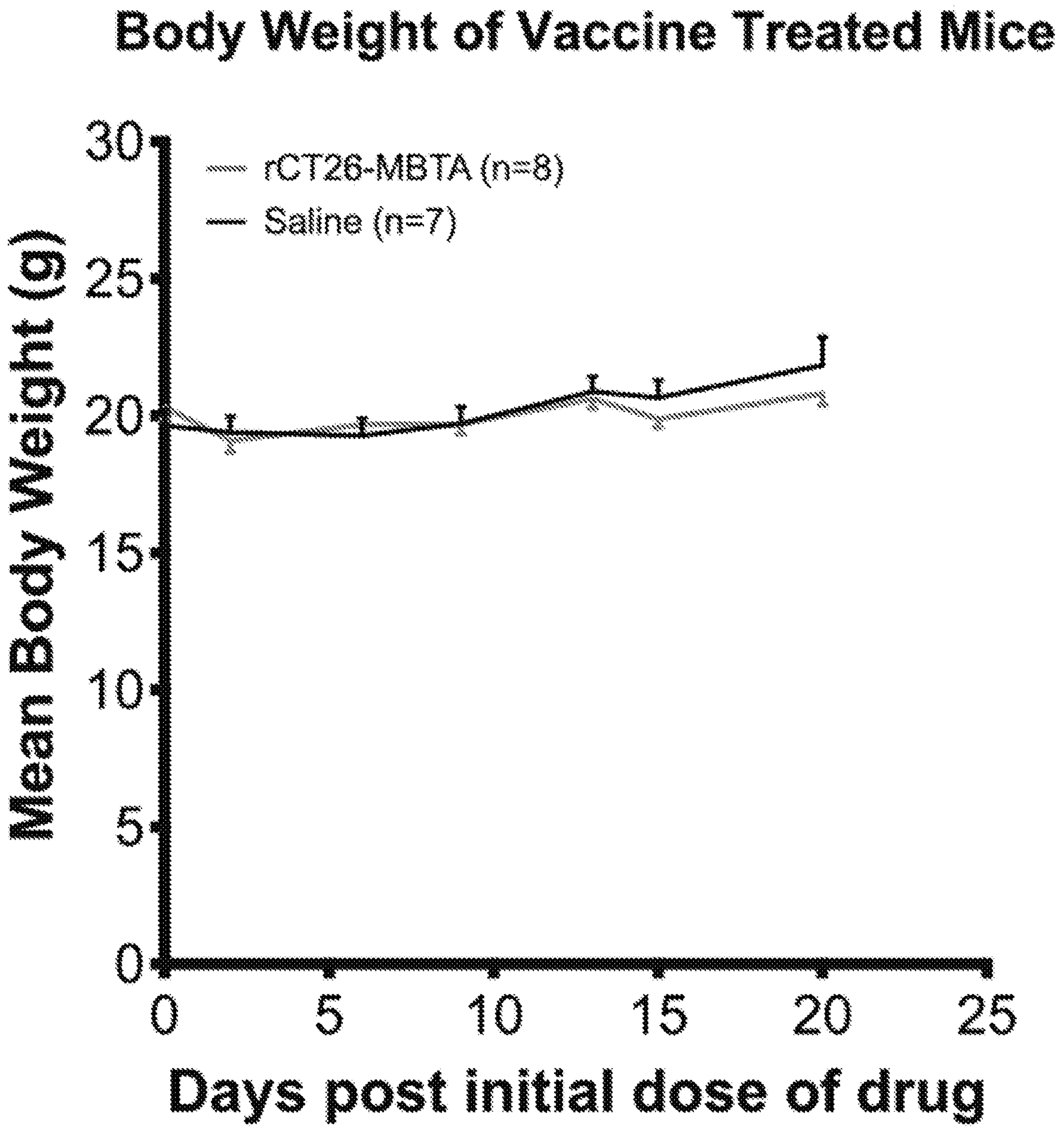
FIG. 5I shows a line plot of the mean body weight (g) of the mice subjected to saline and rCT26-MBTA treatment. rCT26-MBTA treated mice did not demonstrate a significant difference in mean body weight to that of the saline-treated mice.

The MBTA treatment was overall well-tolerated: The in situ MBTA treated mice demonstrated a significant acute drop in mean body weight 3 days after the start of treatment when compared to the pre-treatment level, as shown in FIG. 5H. The loss in body weight was recuperated 7 days after the start of treatment. The mice treated with the rCT26-MBTA vaccine had no significant changes in body weight, as shown in FIG. 5I. None of the in situ MBTA or rCT26-MBTA vaccinated mice died unexpectedly in our investigations.

Example 7: MBTA Treatment Induces Subject-specific Immunological Memory Against CT26 Cells Provided herein are methods for inducing immunological memory against CT26 tumors using the MBTA treatment.

The MBTA treatment can generate durable and robust immunological memory to prevent the relapse of parental tumors in both the periphery and intracranially.

Figure 6A:
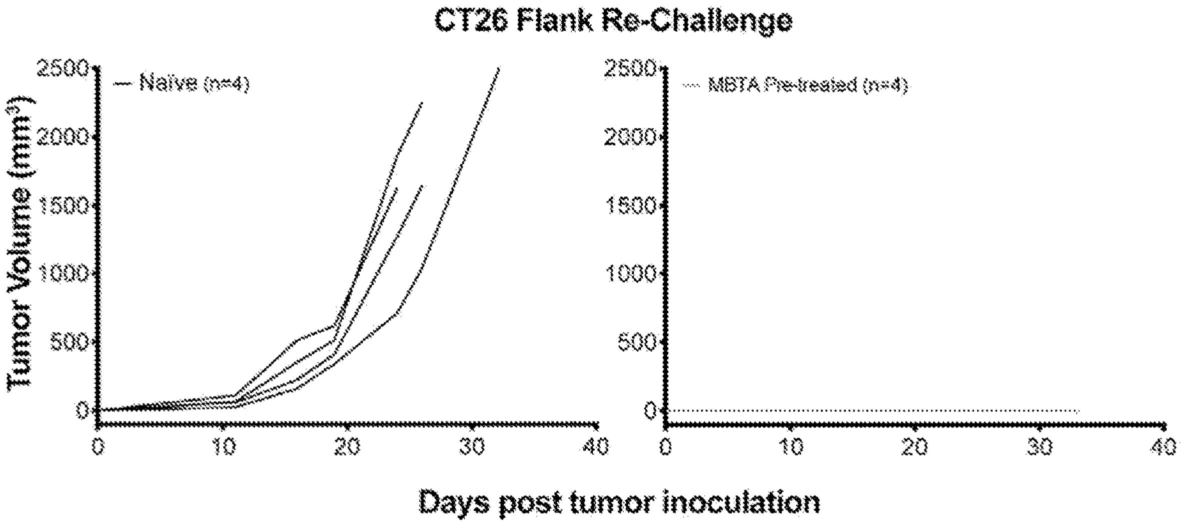
FIGS. 6A-D show MBTA treatment induces subject-specific immunological memory against CT26 cells.
Figure 6B:
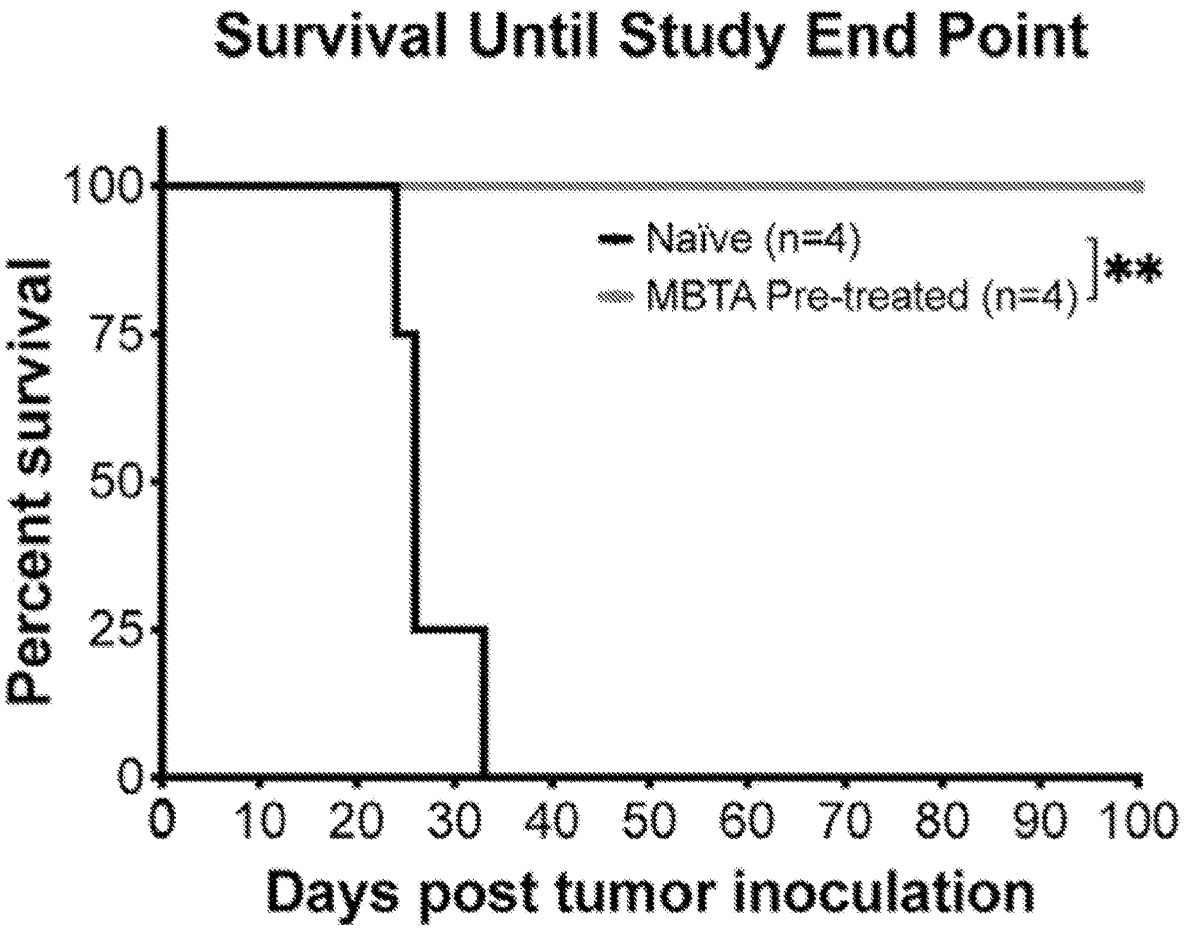

All mice that achieved complete remission (CR) (n=4) of CT26 tumors established in methods of Example 1 were challenged after a minimum of 50 days had passed from their last day of treatment. Mice that achieved CR of CT26 tumors (n=4) and naïve female BALB/c mice were inoculated with 4.5×10^5 CT26 cells suspended in 100 μL PBS into left flank, opposite from the site of initial treatment. FIGS. 6A and 6B show that all CR mice displayed no evidence of tumor growth, while all control mice developed tumors and reached corresponding end points, confirming the induction of an effective immunological memory against CT26 tumor antigens.

Immunological memory generated by the MBTA treatment also extends beyond peripheral circulation and engages CT26 tumors within the central nervous system (CNS).

CT26-Luc cells with stable luciferase expression were used to facilitate monitoring of intracranial tumor growth. Both CR (n=4) and naïve female BALB/c mice were inoculated with CT26-Luc cells in the frontal lobe. 1.0×10^4 CT26-Luc cells in 2 μL HBSS containing 5 μg mL-1 DNase I were stereotactically injected through an entry site at a point 1 mm rostral of the bregma, 2 mm right of midline, and 2 mm deep from the skull surface in the right frontal lobe, using a Hamilton syringe (Hamilton Company), as previously reported, according to Toda et al. (Cancer Gene Ther. 2002, 9, 356). Surgical anesthesia was obtained via vaporized isoflurane.

Figure 6C:
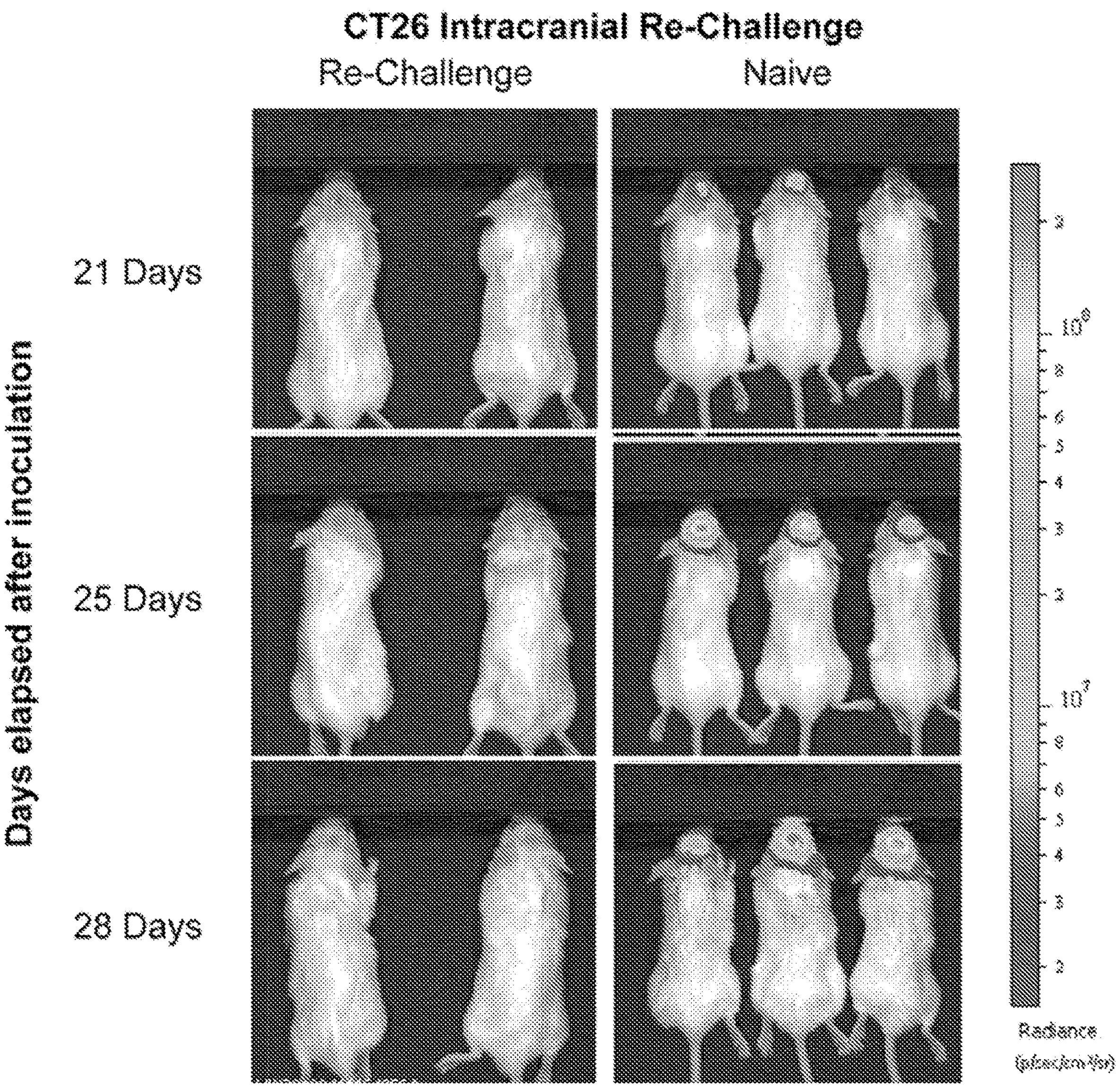
Figure 6D:
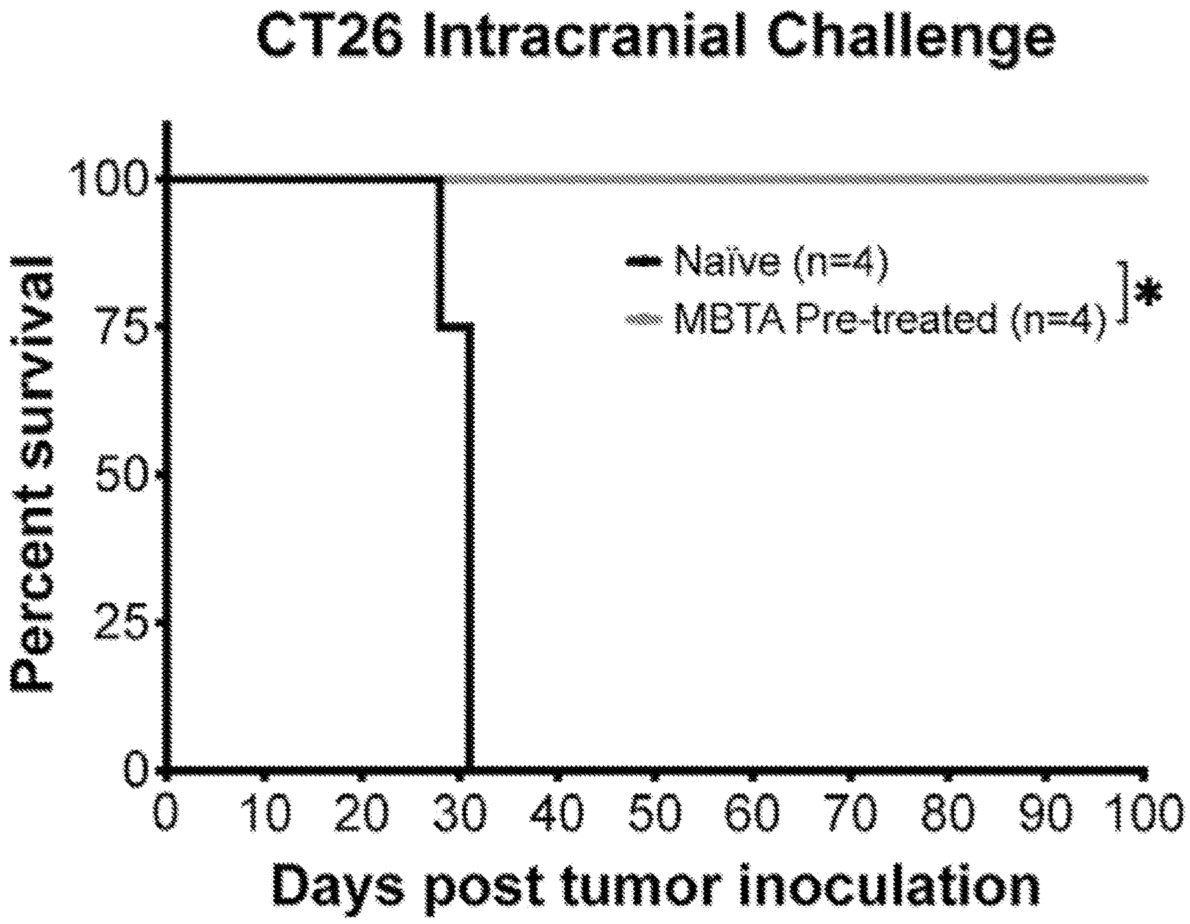

None of the previously treated mice demonstrated evidence of intracranial tumor formation, while all control mice developed intracranial tumors and reached corresponding end points, as shown in FIGS. 6C and 6D. Taken together, re-challenge experiments revealed that MBTA treated mice developed immunological memory against CT26 cells that is not only durable, but also sufficiently robust to prevent the relapse of parental tumors in both the periphery and intracranially.

Example 8: Human Equivalent Dose (HED) Calculation Based on Body Surface Area Provided herein are methods for calculating HED of the MBTA components based on body surface area.

See details from: Nair AB, Jacob S. A simple practice guide for dose conversion between animals and human. *J Basic Clin Pharma* 2016; 7:27-31

A formula to calculate HED is shown as follows:

$$HED\ (\mathrm{mg}/kg) = \mathrm{Animal\ dose}\,(\mathrm{mg}/kg)\ \frac{\mathrm{Animal}\ Km}{\mathrm{Human}\ Km}$$

Mouse Km=3

Human Km=37

Using this formula, the maximum recommended starting dose of Mannan, BAM, Poly I:C, LTA, R-848, and Anti-CD40 antibody is shown in TABLE 3.

TABLE 3

Maximum Recommended Starting Dose (MRSD) based on Body Surface Area

| Component | Net Quantity of medication (mg) per mouse (~20 g) | Animal NOAEL (mg/kg) | HED (mg/kg) | HED/Safety Factor (10) (mg/kg) | Maximum Recommended Starting Dose (MRSD, assuming 60 kg adult) (mg/day) |
|---|---|---|---|---|---|
| Mannan | 0.95 | 47.5 | 3.85135135 | 0.385135135 | 23.10810811 |
| BAM | 0.098 | 4.9 | 0.3972973 | 0.03972973 | 2.383783784 |
| Poly I:C | 0.024 | 1.2 | 0.0972973 | 0.00972973 | 0.583783784 |
| LTA | 0.024 | 1.2 | 0.0972973 | 0.00972973 | 0.583783784 |
| R-848 | 0.024 | 1.2 | 0.0972973 | 0.00972973 | 0.583783784 |
| Anti-CD40 | 0.02 | 1 | 0.0778378 | 0.00778378 | 0.4670269 |

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

What is claimed is:

1. A personalized tumor vaccine comprising:

(a) a phagocytosis stimulating agent which comprises a mannan, wherein the phagocytosis stimulating agent is conjugated to a biocompatible anchor for cell membrane (BAM) wherein the BAM comprise a compound of formula I:

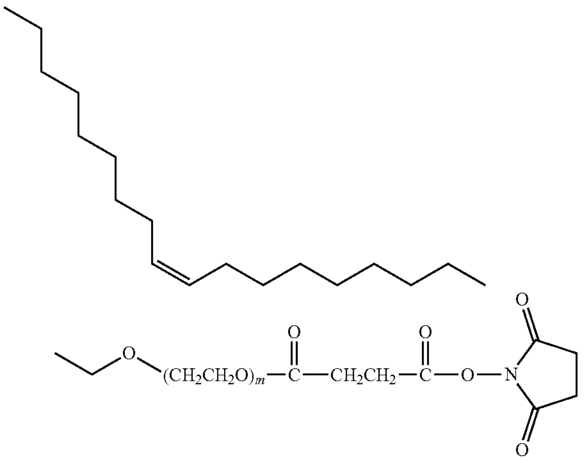

and wherein m is the number of ethylene oxide (EO) repeats in the PEG chain, (b) an immunostimulatory adjuvant, and (c) attenuated cancer cells, wherein the phagocytosis stimulating agent is integrated into a cell membrane of the attenuated cancer cells, wherein the personalized tumor vaccine, when administered to an individual in need thereof, is effective to activate an immune response.

2. The personalized tumor vaccine of claim 1, wherein the attenuated cancer cells are obtained from a tumor of the individual.

3. The personalized tumor vaccine of claim 2, wherein the tumor is selected from the group consist of a solid tumor and a liquid tumor.

4. The personalized tumor vaccine of claim 1, wherein the attenuated cancer cells are prepared by (a) harvesting cancer cells from a biopsy of a site of tumor from the individual, (b) culturing the harvested cancer cells to a therapeutically relevant amount, and (c) irradiating the cultured cancer cells.

5. The personalized tumor vaccine of claim 1, wherein the attenuated cancer cells are present in an amount from about 1.0×10ˆ3 to about 1.0×10ˆ7.

6. The personalized tumor vaccine of claim 1, wherein the immunostimulatory adjuvant comprises a Toll like receptor (TLR) agonist.

7. The personalized tumor vaccine of claim 6, wherein the TLR agonist comprises R-848, poly(I:C), lipoteichoic acid (LTA), or combinations thereof.

8. The personalized tumor vaccine of claim 1, wherein the immunostimulatory adjuvant comprises an anti-CD40 antibody.

9. A personalized tumor vaccine comprising:

(a) a mannan, wherein the mannan is conjugated to a BAM wherein the BAM comprise a compound of formula I:

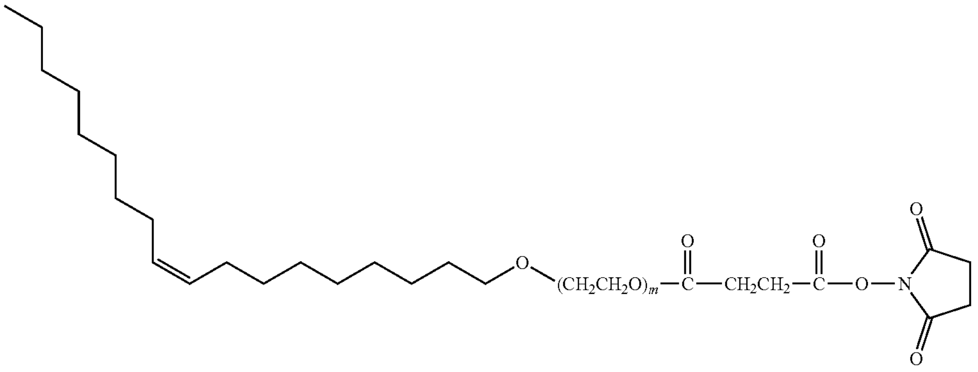

and wherein m is the number of ethylene oxide (EO) repeats in the PEG chain, (b) a R-848, a poly(I:C), and an LTA, (c) an anti-CD40 antibody, (d) irradiated cancer cells, wherein the mannan conjugated to the BAM is integrated into the cell membranes of the irradiated cancer cells, wherein the personalized tumor vaccine, when administered to an individual in need thereof, is effective to activate an immune response.

10. The personalized tumor vaccine of claim 9, wherein the personalized tumor vaccine is administered subcutaneously.

* * * * *